(12) United States Patent
Lau et al.

(10) Patent No.: US 10,683,389 B2
(45) Date of Patent: Jun. 16, 2020

(54) BEADS FOR NUCLEIC ACID SEQUENCING

(71) Applicant: GenapSys, Inc., Redwood City, CA (US)

(72) Inventors: Aldrich N. K. Lau, Palo Alto, CA (US); Paul M. Kenney, Sunnyvale, CA (US); Henrik Persson, Sunnyvale, CA (US)

(73) Assignee: GENAPSYS, INC., Redwood City, CA (US)

( * ) Notice: Subject to any disclaimer, the term of this patent is extended or adjusted under 35 U.S.C. 154(b) by 0 days.

(21) Appl. No.: 15/707,880

(22) Filed: Sep. 18, 2017

(65) Prior Publication Data

US 2018/0105638 A1   Apr. 19, 2018

Related U.S. Application Data

(63) Continuation of application No. PCT/US2016/023899, filed on Mar. 24, 2016.

(Continued)

(51) Int. Cl.
| | |
|---|---|
| C08G 61/12 | (2006.01) |
| C12Q 1/6806 | (2018.01) |
| C40B 50/18 | (2006.01) |
| B01J 19/00 | (2006.01) |
| C12Q 1/6834 | (2018.01) |
| C12Q 1/6874 | (2018.01) |

(52) U.S. Cl.
CPC .......... *C08G 61/12* (2013.01); *B01J 19/0046* (2013.01); *C12Q 1/6806* (2013.01); *C12Q 1/6834* (2013.01); *C12Q 1/6874* (2013.01); *C40B 50/18* (2013.01); *B01J 2219/005* (2013.01); *B01J 2219/00563* (2013.01); *B01J 2219/00648* (2013.01)

(58) Field of Classification Search
CPC . C08G 61/12; B01J 19/0046; B01J 2219/005; B01J 2219/00563; B01J 2219/00648; C40B 50/18; C12Q 1/6806; C12Q 1/6837; C12Q 1/6874
See application file for complete search history.

(56) References Cited

U.S. PATENT DOCUMENTS

| 5,512,439 A | 4/1996 | Hornes et al. |
| 9,399,217 B2 | 7/2016 | Oldham et al. |

(Continued)

FOREIGN PATENT DOCUMENTS

| WO | WO-2012047889 A2 | 4/2012 |
| WO | WO-2012166742 A2 | 12/2012 |

(Continued)

OTHER PUBLICATIONS

Betz et al. KlenTaq polymerase replicates unnatural base pairs by inducing a Watson-Crick geometry. Nat Chem Biol 8:612-614 (2012).

(Continued)

*Primary Examiner* — Shane Fang
(74) *Attorney, Agent, or Firm* — Wilson Sonsini Goodrich & Rosati

(57) ABSTRACT

Provided herein are methods that comprise providing polymer chains comprising a plurality of reactive groups onto the surface of beads and covalent attachment of functionalized biomolecules, such as primers.

26 Claims, 30 Drawing Sheets

Related U.S. Application Data

(60) Provisional application No. 62/241,954, filed on Oct. 15, 2015, provisional application No. 62/196,224, filed on Jul. 23, 2015, provisional application No. 62/172,647, filed on Jun. 8, 2015, provisional application No. 62/140,399, filed on Mar. 30, 2015.

(56) References Cited

U.S. PATENT DOCUMENTS

| | | |
|---|---|---|
| 2003/0108879 A1 | 6/2003 | Klaerner et al. |
| 2004/0146941 A1 | 7/2004 | Zhang et al. |
| 2006/0141464 A1* | 6/2006 | Chiari .................. C08F 220/56 435/6.19 |
| 2010/0179075 A1 | 7/2010 | Lau et al. |
| 2012/0138460 A1 | 6/2012 | Baghbani-Parizi et al. |
| 2014/0287945 A1 | 9/2014 | Lau et al. |
| 2017/0002410 A1 | 1/2017 | Fonnum et al. |

FOREIGN PATENT DOCUMENTS

| | | |
|---|---|---|
| WO | WO-2013082619 A1 | 6/2013 |
| WO | WO-2014152625 A1 | 9/2014 |
| WO | WO-2015089238 A1 | 6/2015 |
| WO | WO-2016160475 A1 | 10/2016 |

OTHER PUBLICATIONS

International Search Report and Written Opinion dated Aug. 12, 2016 for International PCT Patent Application No. PCT/US2016/023899.

Joullie, et al. Evolution of amide bond formation. ARKIVOC Archive for Organic Chemistry. Jun. 30, 2010. vol. 2010, Issue 8, pp. 189-250. DOI: http://dx.doi.org/10.3998/ark.5550190.0011.816.

Liu, et al. Immobilization of DNA onto poly(dimethylsiloxane) surfaces and application to a microelectrochemical enzyme-amplified DNA hybridization assay. Langmuir. Jul. 6, 2004;20(14):5905-10.

* cited by examiner

Where, T = —NH₂ ; —NH(CH₂OH) , —NMe₂ , —(CH₂CH₂O)ₙ—CH₃, —NH(CH₃), or —NH(CH₂CH₂OH)
y is less than or equal to about 60%, and z is greater than or equal to about 40%, and (y+z) = 100%
Initiator = Thermal initiators, e.g., 2,2'-azobis(2,4-dimethylvaleronitrile)

R =

Q = —NO₂ or –Fₓ ; where x = 1, 2, 3, 4 or 5

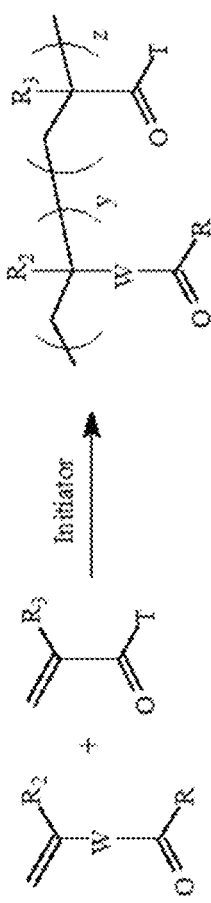
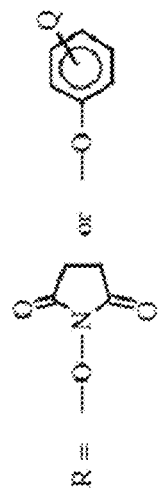

Where, T = —NH$_2$, —N(CH$_3$)$_2$, —NH(CH$_2$)$_t$—OH, —(OCH$_2$CH$_2$)$_v$—OH, —(OCH$_2$CH$_2$)$_v$—OCH$_3$, —NH(CH$_3$);
—OCH$_3$, or —(OCH$_2$CH$_2$)$_v$—CH$_3$;

(t = 1 to 4 ; v = 1 to 100 ; R$_2$ and R$_3$ independently H or CH$_3$ ;

y is less than or equal to about 60 mole%, and z is greater than or equal to about 40 mole%, and (y+z) = 100%

W is a single bond or [phenyl with D$_t$] and D = H or CH$_3$ ; and

Initiator = Thermal initiator, e.g., 2,2'-azobis(2,4-dimethylvaleronitrile)

Q = —NO$_2$ or —F$_x$ ; where x = 1, 2, 3, 4 or 5

R = [phenyl with Q] or [succinimidyl N—O]

Q = —NO$_2$ or —F$_x$ ; Where, x = 3, 4 or 5

FIG. 9A

BEADS FOR NUCLEIC ACID SEQUENCING

CROSS-REFERENCE

This application is a continuation of PCT Application Serial No. PCT/US2016/023899, filed on Mar. 24, 2016, which claims priority to U.S. Provisional Patent Application Ser. No. 62/241,954, filed on Oct. 15, 2015, U.S. Provisional Patent Application Ser. No. 62/196,224, filed on Jul. 23, 2015, U.S. Provisional Patent Application No. 62/172,647, filed on Jun. 8, 2015 and U.S. Provisional Patent Application Ser. No. 62/140,399, filed on Mar. 30, 2015, which applications are herein incorporated by reference in their entirety for all purposes.

BACKGROUND

The goal to elucidate the entire human genome has created interest in technologies for rapid nucleic acid (e.g., DNA) sequencing, both for small and large scale applications. Important parameters are sequencing speed, sequencing accuracy, length of sequence that can be read during a single sequencing run, and amount of nucleic acid template required to generate sequencing information. Large scale genome projects are currently too expensive to realistically be carried out for a large number of subjects (e.g., patients). Furthermore, as knowledge of the genetic basis for human diseases increases, there will be an ever-increasing need for accurate, high-throughput DNA sequencing that is affordable for clinical applications. Practical methods for determining the base pair sequences of single molecules of nucleic acids, preferably with high speed, high accuracy and long read lengths, may provide measurement capability.

Nucleic acid sequencing is a process that can be used to provide sequence information for a nucleic acid sample. Such sequence information may be helpful in diagnosing and/or treating a subject with a condition. For example, the nucleic acid sequence of a subject may be used to identify, diagnose and potentially develop treatments for genetic diseases. As another example, research into pathogens may lead to treatment for contagious diseases. Unfortunately, though, existing sequencing technology of the status quo is expensive and may not provide sequence information within a time period and/or at an accuracy that may be sufficient to diagnose and/or treat a subject with a condition.

SUMMARY

Recognized herein is the need for improved devices and methods for sequencing, amplifying, detecting, analyzing, and/or performing sample preparation procedures for nucleic acids and other biomolecules. The sensors described herein are able to detect nucleotide incorporation or other biological reactions with a high degree of accuracy.

An aspect of the present disclosure provides a method for the preparation of primer-conjugated magnetic beads, comprising: (a) grafting a plurality of polymer chains comprising a plurality of first reactive groups onto an aminated bead to provide a plurality of second reactive groups each coupled to the bead through a respective one of the polymer chains; and (b) covalently attaching amine- or hydroxy-terminated primers to the second reactive groups, where an individual polymer chain of the plurality of polymer chains comprises a repeat unit comprising a functional group that is different from functional groups of the first reactive groups and the second reactive groups, where the functional group is hydrophilic, and where the individual polymer chain comprises greater than or equal to 40 mole % (mol %) of the functional group. In some embodiments, (a) comprises covalently grafting the plurality of polymer chains comprising a plurality of first reactive groups onto the aminated bead to provide the plurality of second reactive groups each coupled to the bead through a respective one of the polymer chains.

In some embodiments of aspects provided herein, the first and second reactive groups are the same. In some embodiments of aspects provided herein, the bead is magnetic. In some embodiments of aspects provided herein, the polymer is pre-fabricated. In some embodiments of aspects provided herein, the method further comprises sequencing a plurality of clonal nucleic acid molecules that are coupled to the amine- or hydroxy-terminated primers. In some embodiments of aspects provided herein, prior to (a), the polymer chains include reactive ester repeat units having a concentration of less than or equal to about 60 mol %. In some embodiments of aspects provided herein, the method further comprises aminating a bead comprising carboxylic acid groups to provide the aminated bead. In some embodiments of aspects provided herein, the functional group is —NH$_2$; —NH(CH$_3$), —N(CH$_3$)$_2$; —NH(CH$_2$)t-OH with 't'=1 to 4; —(OCH$_2$CH$_2$)$_v$—OH, with 'v'=1 to 100; —(OCH$_2$CH$_2$)$_v$—CH3 with 'v'=1 to 100; —(OCH$_2$CH$_2$)$_v$—OCH$_3$ with 'v'=1 to 100 or —OCH$_3$.

Another aspect of the present disclosure provides a reagent comprising beads that are functionalized with polymer chains, where each of the polymer chains comprises a carbon backbone of the formula:

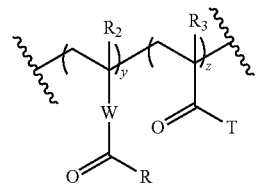

where 'R' is

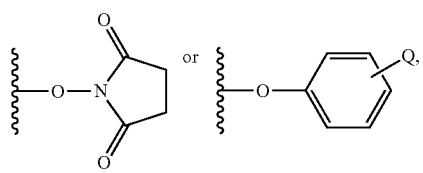

with 'Q'=NO$_2$ or F$_x$, with 'x'=1, 2, 3, 4 or 5;

where 'T' is selected from the group consisting of NH$_2$, NH(CH$_3$), N(CH$_3$)$_2$, NH(CH$_2$)$_t$OH, (OCH$_2$CH$_2$)$_v$CH$_3$, (OCH$_2$CH$_2$)$_v$OH, (OCH$_2$CH$_2$)$_v$OCH$_3$ and OCH$_3$, with 't'=1 to 4, 'v'=1 to 100;

where 'R$_2$' and 'R$_3$' are independently H or CH$_3$;

where 'y' and 'z' are mole percentages, where ('y'+'z')= 100 mole %, where 'y' is less than or equal to 60 mole %, 'z' is greater than or equal to 40 mole %; and where 'W' is a single bond or

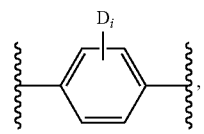

where '$D_i$'=H or $CH_3$, and where 'i'=1, 2, 3 or 4, independently.

In some embodiments of aspects provided herein, 'R' is

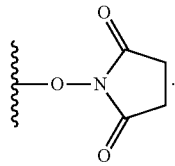 [SMILES: *ON1C(=O)CCC1=O]

In some embodiments of aspects provided herein, 'R' is

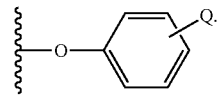

In some embodiments of aspects provided herein, 'Q' is $NO_2$. In some embodiments of aspects provided herein, 'Q' is $F_x$.

In some embodiments of aspects provided herein, 'W' is

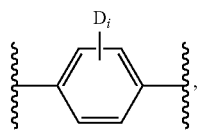

where '$D'_i$'=H or $CH_3$, and where 'i' is 1, 2, 3 or 4 independently.

In some embodiments of aspects provided herein, '$D_i$' is H. In some embodiments of aspects provided herein, '$D_i$' is $CH_3$. In some embodiments of aspects provided herein, 'T' is $NH_2$. In some embodiments of aspects provided herein, 'T' is $NH(CH_2)_tOH$. In some embodiments of aspects provided herein, 'T' is $(OCH_2CH_2)_vOH$. In some embodiments of aspects provided herein, 'T' is $(OCH_2CH_2)_vOCH_3$. In some embodiments of aspects provided herein, 'T' is $NH(CH_3)$. In some embodiments of aspects provided herein, 'T' is $NH(CH_3)_2$. In some embodiments of aspects provided herein, 'T' is $OCH_3$. In some embodiments, of aspects provided herein, 'T' is $(OCH_2CH_2)_vCH_3$.

In some embodiments of aspects provided herein, '$R_2$' is H. In some embodiments of aspects provided herein, '$R_2$' is $CH_3$. In some embodiments of aspects provided herein, '$R_3$' is H. In some embodiments of aspects provided herein, '$R_3$' is $CH_3$. In some embodiments of aspects provided herein, an individual polymer chain of the polymer chains comprises a molecular weight of about 50 kiloDalton (KDa) to about 2500 KDa. In some embodiments of aspects provided herein, the beads are magnetic beads. In some embodiments of aspects provided herein, a nucleic acid molecule is coupled to the beads through 'R'. In some embodiments of aspects provided herein, the nucleic acid molecule is a primer.

Another aspect of the present disclosure provides a method for coupling primers to a bead, comprising: (a) providing a bead comprising amine groups linked (e.g., covalently linked) to a surface of the bead; (b) reacting at least a portion of the amine groups with polymer chains comprising a carbon backbone of the formula:

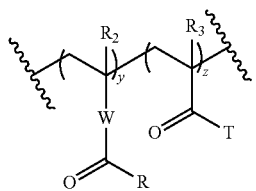

where 'R' is

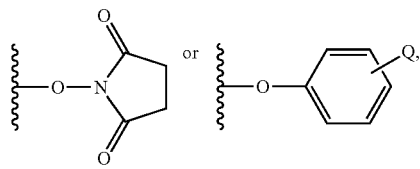

where 'Q'=$NO_2$ or $F_x$, with 'x'=1, 2, 3, 4 or 5;

where 'T' is selected from the group consisting of $NH_2$, $NH(CH_3)$, $N(CH_3)_2$, $NH(CH_2)_tOH$, $(OCH_2CH_2)_vCH_3$, $(OCH_2CH_2)_vOH$, $(OCH_2CH_2)_vOCH_3$ and $OCH_3$, where 't'=1 to 4, 'v'=1 to 100;

where '$R_2$' and '$R_3$' are independently H or $CH_3$;

where 'y' and 'z' are mole percentages, where ('y'+'z')=100 mole %, where 'y' is less than or equal to 60 mole %, 'z' is greater than or equal to 40 mole %; and where 'W' is a single bond or

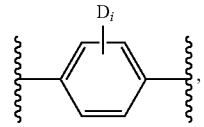

where '$D_i$'=H or $CH_3$, and where 'i'=1, 2, 3 or 4, independently, thereby providing immobilized polymer chains that are coupled to the bead; and (c) reacting the immobilized polymer chains with a primer comprising an amine group, providing immobilized primers coupled to at least a portion of the immobilized polymer chains.

In some embodiments of aspects provided herein, 'R' is

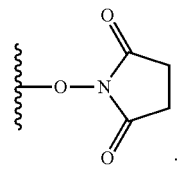 [SMILES: *ON1C(=O)CCC1=O]

In some embodiments of aspects provided herein, 'R' is

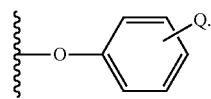

In some embodiments of aspects provided herein, 'Q' is $NO_2$.

In some embodiments of aspects provided herein, 'Q' is $F_x$.

In some embodiments of aspects provided herein, 'W' is

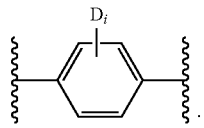

In some embodiments of aspects provided herein, '$D_i$' is H. In some embodiments of aspects provided herein, '$D_i$' is $CH_3$. In some embodiments of aspects provided herein, 'T' is $NH_2$. In some embodiments of aspects provided herein, 'T' is $NH(CH_2)_tOH$. In some embodiments of aspects provided herein, 'T' is $(OCH_2CH_2)_vOH$. In some embodiments of aspects provided herein, 'T' is $(OCH_2CH_2)_vOCH_3$. In some embodiments of aspects provided herein, 'T' is $NH(CH_3)$. In some embodiments of aspects provided herein, 'T' is $NH(CH_3)_2$. In some embodiments of aspects provided herein, 'T' is $OCH_3$. In some, of aspects provided herein, 'T' is $(OCH_2CH_2)_vCH_3$.

In some embodiments of aspects provided herein, '$R_2$' is H. In some embodiments of aspects provided herein, '$R_2$' is $CH_3$. In some embodiments of aspects provided herein, '$R_3$' is H. In some embodiments of aspects provided herein, '$R_3$' is $CH_3$. In some embodiments of aspects provided herein, an individual polymer chain of the polymer chains comprises a molecular weight of about 50 kiloDalton (KDa) to about 2500 KDa. In some embodiments of aspects provided herein, the bead is a magnetic bead. In some embodiments of aspects provided herein, the method further comprises, after (c), capping at least a portion of any free 'R' groups on the immobilized polymer chains. In some embodiments of aspects provided herein, the capping is achieved by reacting the at least a portion of any remaining 'R' groups with ammonium hydroxide in the presence of triethylamine. In some embodiments of aspects provided herein, the method further comprises repeating (a)-(c) for one or more additional beads.

Another aspect of the present disclosure provides a reagent comprising beads that are functionalized with polymer chains, where each of the polymer chains comprises a carbon backbone of the formula:

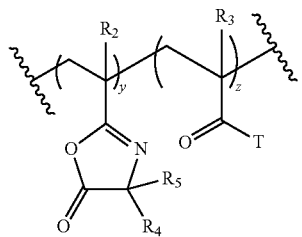

where 'T' is selected from the group consisting of $NH_2$, $NH(CH_3)$, $N(CH_3)_2$, $NH(CH_2)_tOH$, $(OCH_2CH_2)_vCH_3$, $(OCH_2CH_2)_vOH$, $(OCH_2CH_2)_vOCH_3$ and $OCH_3$, where 't' is 1 to 4, 'v' is 1 to 100;

where '$R_2$', '$R_3$', '$R_4$' and '$R_5$' are independently H or $CH_3$; and where 'y' and 'z' are mole percentages, where ('y'+'z')=100 mole %, where 'y' is less than or equal to 60 mole %, 'z' is greater than or equal to 40 mole %.

In some embodiments of aspects provided herein, 'T' is $NH_2$. In some embodiments of aspects provided herein, 'T' is $NH(CH_2)_tOH$. In some embodiments of aspects provided herein, 'T' is $(OCH_2CH_2)_vOH$. In some embodiments of aspects provided herein, 'T' is $(OCH_2CH_2)_vOCH_3$. In some embodiments of aspects provided herein, 'T' is $NH(CH_3)$. In some embodiments of aspects provided herein, 'T' is $NH(CH_3)_2$. In some embodiments of aspects provided herein, 'T' is $OCH_3$. In some embodiments, of aspects provided herein, 'T' is $(OCH_2CH_2)_vCH_3$. In some embodiments of aspects provided herein, an individual polymer chain of the polymer chains comprises a molecular weight of about 50 kiloDalton (KDa) to about 2500 KDa. In some embodiments of aspects provided herein, the beads are magnetic beads.

In some embodiments of aspects provided herein, a nucleic acid molecule is coupled to the beads through the

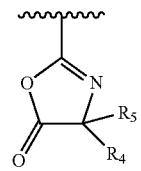

functional group.

In some embodiments of aspects provided herein, the nucleic acid molecule is a primer.

Another aspect of the present disclosure provides a method for coupling primers to a bead, comprising: (a) providing a bead comprising amine groups linked to a surface of the bead; (b) reacting at least a portion of the amine groups with polymer chains comprising a carbon backbone of the formula:

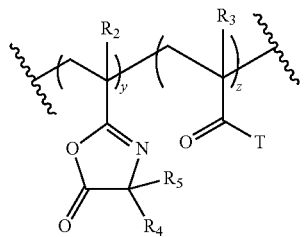

where 'T' is selected from the group consisting of $NH_2$, $NH(CH_3)$, $N(CH_3)_2$, $NH(CH_2)_tOH$, $(OCH_2CH_2)_vCH_3$, $(OCH_2CH_2)_vOH$, $(OCH_2CH_2)_vOCH_3$ and $OCH_3$, where 't'=1 to 4, 'v'=1 to 100;

where '$R_2$', '$R_3$', '$R_4$' and '$R_5$' are independently H or $CH_3$; and where 'y' and 'z' are mole percentages, where ('y'+'z')=100 mole %, where 'y' is less than or equal to 60 mole %, 'z' is greater than or equal to 40 mole %; and (c) reacting the immobilized polymer chains with a primer comprising an amine group, providing immobilized primers coupled to at least a portion of the immobilized polymer chains.

In some embodiments of aspects provided herein, 'T' is $NH_2$. In some embodiments of aspects provided herein, 'T' is $NH(CH_2)_tOH$. In some embodiments of aspects provided herein, 'T' is $(OCH_2CH_2)_vOH$. In some embodiments of aspects provided herein, 'T' is $(OCH_2CH_2)_vOCH_3$. In some embodiments of aspects provided herein, 'T' is $NH(CH_3)$. In some embodiments of aspects provided herein, 'T' is $NH(CH_3)_2$. In some embodiments of aspects provided herein, 'T' is OCH₃. In some embodiments, of aspects provided herein, 'T' is (OCH₂CH₂)ᵥCH₃.

In some embodiments of aspects provided herein, an individual polymer chain of the polymer chains comprises a molecular weight of about 50 kiloDalton (KDa) to about 2500 KDa. In some embodiments of aspects provided herein, the bead is a magnetic bead. In some embodiments of aspects provided herein, the method further comprises repeating (a)-(c) for one or more additional beads.

An additional aspect of the disclosure provides a primer-coated bead comprising a bead, a linker attached to the bead and a primer attached to the linker. The linker can comprise a polymer chain having a discrete number of repeat units. In some cases, the bead is magnetic. In some cases, the polymer chain comprises polyethylene glycol (PEG) repeat units. In some cases, the polymer chain comprises at least about 20 repeat units. In some cases, the primer is attached to the linker with an amide bond. In some cases, the bead comprises an equal number of primers and linkers.

An additional aspect of the disclosure provides a method for producing a primer-coated bead. The method can include providing a bead having a first carboxyl group; attaching a linker comprising a first amine group, a polymer chain comprising a discrete number of repeat units and a second carboxyl group to the bead by reacting the first amine group with the first carboxyl group; and attaching a primer comprising a second amine group to the linker by reacting the second amine group with the second carboxyl group.

An additional aspect of the disclosure provides a method for producing a primer-coated bead. The method can include providing a bead having a first amine group; attaching a linker comprising a first carboxyl group, a polymer chain comprising a discrete number of repeat units, and a second amine group to the bead by reacting the first carboxyl group with the first amine group; and attaching a primer comprising a second carboxyl group to the linker by reacting the second carboxyl group with the second amine group.

In some aspects, the bead is magnetic. In some aspects, the polymer chain comprises polyethylene glycol (PEG) repeat units. In some aspects, the polymer chain comprises at least about 20 repeat units. In some aspects, an equal number of primers and linkers are used.

An additional aspect of the disclosure provides a reagent comprising beads that are functionalized with polymer chains. Each of the polymer chains can comprise a carbon backbone of the formula:

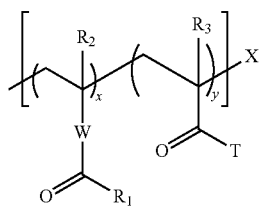

where 'X' is a halide;
where 'R₁' is OH; (OCH₂CH₂)ᵥOH with v=1 to 200; NH(CH₂)ₐOH, with 'a'=1 to 6; NH(CH₂CH₂O)ₜCH₂CH₂OH with 't'=0 to 200;

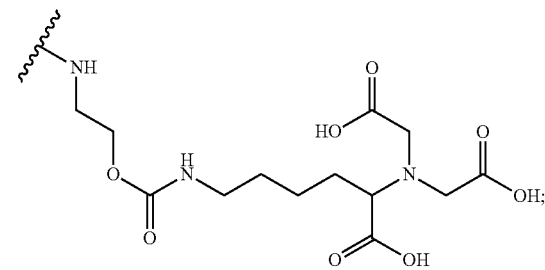

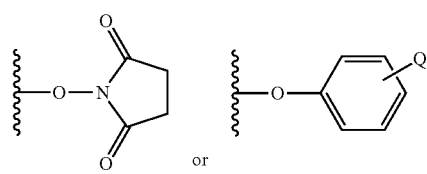

with 'Q'=NO₂ or F_z, with 'z'=1, 2, 3, 4 or 5;
where 'T' is selected from the group consisting of NH₂, NH(CH₃), N(CH₃)₂, N(CH₂CH₃)₂, NHCH₂CH₂(OCH₂CH₂)ᵦOCH₃ and (OCH₂CH₂)ₐOCH₃, where 'b'=0 to 200, 'd'=1 to 200;

where 'R₂' and 'R₃' are independently H or CH₃;

where 'x' and 'y' are mole percentages, where ('x'+'y')= 100 mol % and 'x' ranges from 0.01 to 100 mol %, and where 'W' is a single bond or

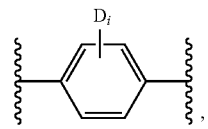

where 'Dᵢ'=H or CH₃, and where 'i' is 1, 2, 3 or 4, independently.

In some embodiments, 'X' is bromine. In some embodiments, 'R₁' is

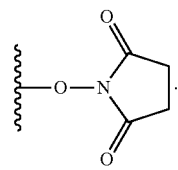 [SMILES: *ON1C(=O)CCC1=O]

In some embodiments, 'R₁' is

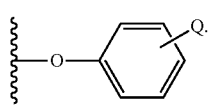

In some embodiments, 'R₁' is OH. In some embodiments, 'R₁' is

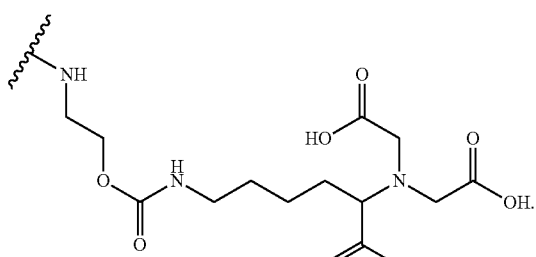

In some embodiments, '$R_1$' is $(OCH_2CH_2)_vOH$. In some embodiments, '$R_1$' is $NH(CH_2)_aOH$. In some embodiments, '$R_1$' is $NH(CH_2CH_2O)_tCH_2CH_2OH$. In some embodiments, 'W' is a single bond. In some embodiments, 'W' is

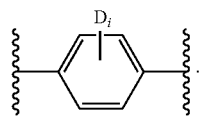

In some embodiments, an individual polymer chain of the polymer chains comprises a molecular weight of about 50 kiloDalton (KDa) to about 2500 KDa. In some embodiments, the beads are magnetic beads. In some embodiments, a nucleic acid molecule is coupled to the beads through '$R_1$'. In some embodiments, the nucleic acid molecule is a primer.

An additional aspect of the disclosure provides a reagent comprising beads that are functionalized with polymer chains. Each of the polymer chains can comprise a carbon backbone of the formula:

where 'X' is a halide;

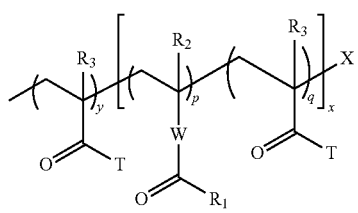

where '$R_1$' is OH; $(OCH_2CH_2)_vOH$ with v=1 to 200; $NH(CH_2)_aOH$, with 'a'=1 to 6; $NH(CH_2CH_2O)_t CH_2CH_2OH$ with 't'=0 to 200,

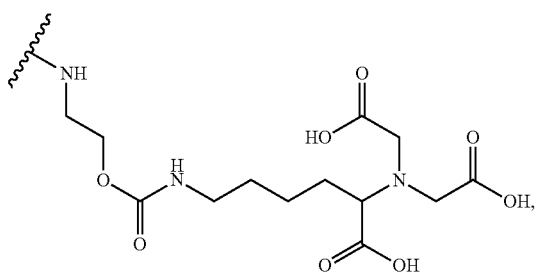 [SMILES: *NCCOC(=O)NCCCCC(C(=O)O)N(CC(=O)O)CC(=O)O]

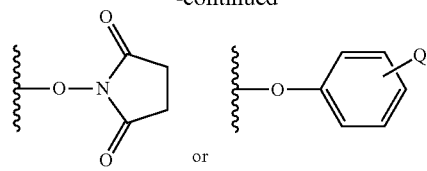

with 'Q'=$NO_2$ or $F_z$, where 'z' is 1, 2, 3, 4 or 5;

where 'T' is selected from the group consisting of $NH_2$, $NH(CH_3)$, $N(CH_3)_2$, $N(CH_2CH_3)_2$, $NHCH_2CH_2(OCH_2CH_2)_bOCH_3$ and $(OCH_2CH_2)_dOCH_3$, where 'b'=0 to 200, 'd'=1 to 200;

where '$R_2$' and '$R_3$' are independently H or $CH_3$;

where 'y', 'p', 'q' and 'x' are mole percentages, where ('x'+'y')=100 mol %, ('p'+'q')=x, x ranges from 0.01 to 100 mol % and 'p' ranges from 0.01 to 100 mol %, and where 'W' is a single bond or

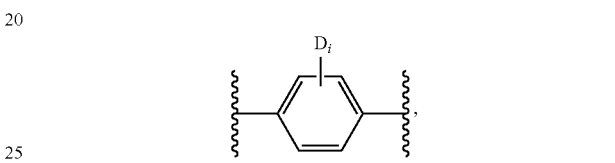

where '$D_i$' is H or $CH_3$, and where 'i' is 1, 2, 3 or 4, independently.

In some embodiments, 'X' is bromine. In some embodiments, '$R_1$' is

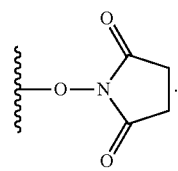

In some embodiments, '$R_1$' is

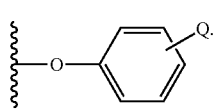

In some embodiments, '$R_1$' is OH. In some embodiments, '$R_1$' is $(OCH_2CH_2)_vOH$. In some embodiments, '$R_1$' is

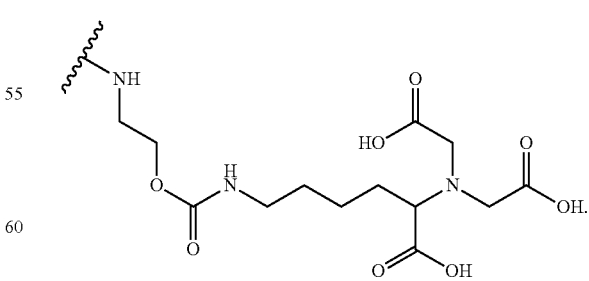

In some embodiments, $R_1$' is $NH(CH_2)_aOH$. In some embodiments, '$R_1$' is $NH(CH_2CH_2O)_tCH_2CH_2OH$. In some embodiments, 'W' is a single bond. In some embodiments, 'W' is

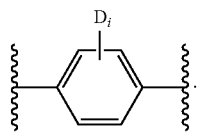

In some embodiments, an individual polymer chain of the polymer chains comprises a molecular weight of about 50 kiloDalton (KDa) to about 2500 KDa. In some embodiments, the beads are magnetic beads. In some embodiments, a nucleic acid molecule is coupled to the beads through '$R_1$'. In some embodiments, the nucleic acid molecule is a primer.

Another aspect of the disclosure provides a reagent comprising beads that are functionalized with polymer chains. Each of the polymer chains can comprise a carbon backbone of the formula:

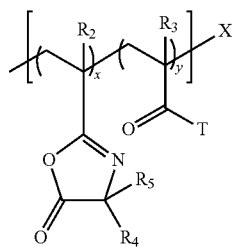

where 'X' is a halide;

where '$R_2$', '$R_3$', '$R_4$' and '$R_5$' are independently H or $CH_3$;

where 'T' is selected from the group consisting of $NH_2$, $NH(CH_3)$, $N(CH_3)_2$, $N(CH_2CH_3)_2$, $NHCH_2CH_2(OCH_2CH_2)_bOCH_3$ and $(OCH_2CH_2)_dOCH_3$, where 'b'=0 to 200, 'd'=1 to 200; and where 'x' and 'y' are mole percentages, where ('x'+'y')= 100 mol % and 'x' ranges from 0.01 to 100 mol %.

In some embodiments, 'X' is bromine. In some embodiments, 'T' is $NH_2$. In some embodiments, 'T' is $NH(CH_3)$. In some embodiments, 'T' is $N(CH_3)_2$. In some embodiments, 'T' is $N(CH_2CH_3)_2$. In some embodiments, 'T' is $NHCH_2CH_2(OCH_2CH_2)_bOCH_3$. In some embodiments, 'T' is $(OCH_2CH_2)_dOCH_3$.

In some embodiments, an individual polymer chain of the polymer chains comprises a molecular weight of about 50 kiloDalton (KDa) to about 2500 KDa. In some embodiments, the beads are magnetic beads. In some embodiments, a nucleic acid molecule is coupled to the beads through the

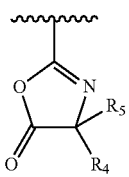

functional group. In some embodiments, the nucleic acid molecule is a primer.

An additional aspect of the disclosure provides a reagent comprising beads that are functionalized with polymer chains. Each of the polymer chains can comprise a carbon backbone of the formula:

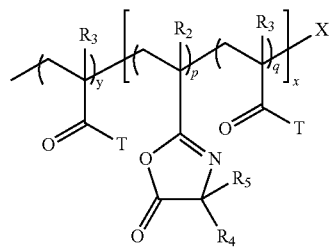

where 'X' is a halide;

where '$R_2$', '$R_3$', '$R_4$' and '$R_5$' are independently H or $CH_3$;

where 'T' is selected from the group consisting of $NH_2$, $NH(CH_3)$, $N(CH_3)_2$, $N(CH_2CH_3)_2$, $NHCH_2CH_2(OCH_2CH_2)_bOCH_3$ and $(OCH_2CH_2)_dOCH_3$, where 'b'=0 to 200, 'd'=1 to 200; and where 'y', 'p', 'q' and 'x' are mole percentages, where ('x'+'y')=100 mol %, ('p'+'q')='x', 'x' ranges from 0.01 to 100 mol % and 'p' ranges from 0.01 to 100 mol %.

In some embodiments, 'X' is bromine. In some embodiments, 'T' is $NH_2$. In some embodiments, 'T' is $NH(CH_3)$. In some embodiments, 'T' is $N(CH_3)_2$. In some embodiments, 'T' is $N(CH_2CH_3)_2$. In some embodiments, 'T' is $NHCH_2CH_2(OCH_2CH_2)_bOCH_3$. In some embodiments, 'T' is $(OCH_2CH_2)_dOCH_3$.

In some embodiments, an individual polymer chain of the polymer chains comprises a molecular weight of about 50 kiloDalton (KDa) to about 2500 KDa. In some embodiments, the beads are magnetic beads. In some embodiments, a nucleic acid molecule is coupled to the beads through the

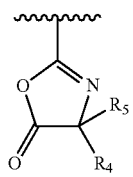

functional group. In some embodiments, the nucleic acid molecule is a primer.

An additional aspect of the disclosure provides a method for coupling oligonucleotides to a bead, comprising: (a) providing the bead comprising

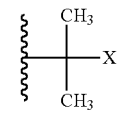

linked to a surface of the bead, where 'X' is a halide; (b) with the bead in a reaction mixture, reacting a first monomer and a second monomer with the bead to generate immobilized polymer chains comprising reactive '$R_1$' groups that are coupled to the bead, where: (i) the first monomer comprises:

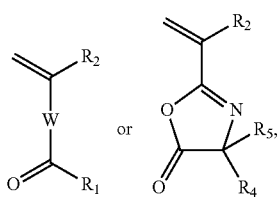

where '$R_1$' is OH; $(OCH_2CH_2)_vOH$ with v=1 to 200; $NH(CH_2)_aOH$, with 'a'=1 to 6; $NH(CH_2CH_2O)_tCH_2CH_2OH$ with 't'=0 to 200,

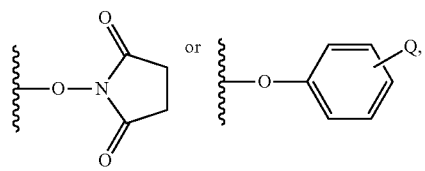

where '$Q$'=$NO_2$ or $F_z$, where 'z'=1, 2, 3, 4 or 5;

where 'T' is selected from the group consisting of $NH_2$, $NH(CH_3)$, $N(CH_3)_2$, $N(CH_2CH_3)_2$, $NHCH_2CH_2(OCH_2CH_2)_bOCH_3$ and $(OCH_2CH_2)_dOCH_3$, where 'b'=0 to 200, 'd'=1 to 200;

where '$R_2$', '$R_4$' and '$R_5$' are independently H or $CH_3$; and where 'W' is a single bond or

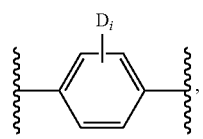

where '$D_i$' is H or $CH_3$, and where 'i' is 1, 2, 3 or 4, independently; and (ii) the second monomer comprises:

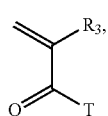

where 'T' is selected from the group consisting of $NH_2$, $NH(CH_3)$, $N(CH_3)_2$, $N(CH_2CH_3)_2$, $NHCH_2CH_2(OCH_2CH_2)_bOCH_3$ and $(OCH_2CH_2)_dOCH_3$, where 'b'=0 to 200, 'd'=1 to 200, where '$R_3$' is H or $CH_3$; and (iii) the polymer chains are generated via an atom transfer radical polymerization (ATRP) reaction of the first and/or second monomer with the

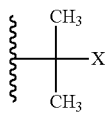

group of the bead; and (c) coupling one or more oligonucleotides to the polymer chains through '$R_1$'.

In some embodiments, the first monomer is

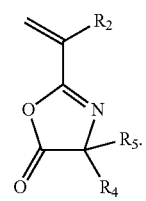

In some embodiments, the polymer chains comprise a carbon backbone of the formula:

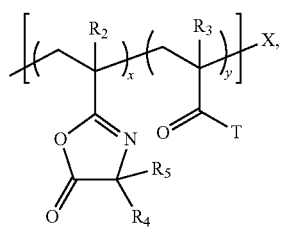

where 'x' and 'y' are mole percentages, where ('x'+'y')=100 mol % and 'x' ranges from 0.01 to 100 mol %.

In some embodiments, the polymer chains comprise a carbon backbone of the formula:

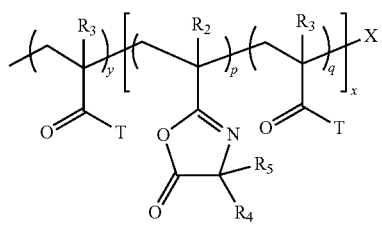

where 'y', 'p', 'q' and 'x' are mole percentages, where ('x'+'y')=100 mol %, ('p'+'q')='x', 'x' ranges from 0.01 to 100 mol % and 'p' ranges from 0.01 to 100 mol %.

In some embodiments, the polymer chains comprise a carbon backbone of the formula:

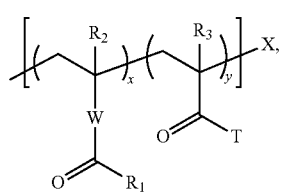

where 'x' and 'y' are mole percentages, where ('x'+'y')=100 mol % and 'x' ranges from 0.01 to 100 mol %.

In some embodiments, 'W' is a single bond and '$R_1$' is $NH(CH_2)_2OH$. In some embodiments, the method further comprises reacting the $NH(CH_2)_2OH$ with N-(5-Amino-1-carboxypentyl)iminodiacetic acid to generate polymer chains comprising:

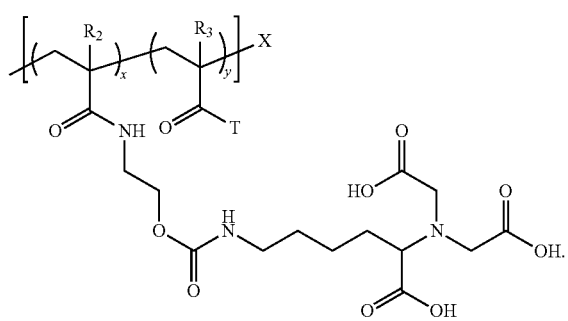

In some embodiments, the polymer chains comprise a backbone of the formula:

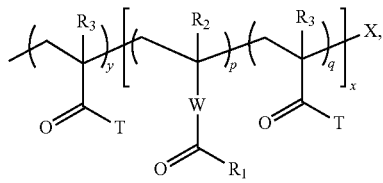

where 'y', 'p', 'q' and 'x' are mole percentages, where ('x'+'y')=100 mol %, ('p'+'q')='x', 'x' ranges from 0.01 to 100 mol % and 'p' ranges from 0.01 to 100 mol %.

In some embodiments, '$R_1$' is

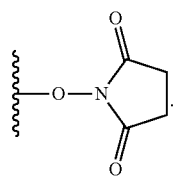 [SMILES: *ON1C(=O)CCC1=O]

In some embodiments, '$R_1$' is

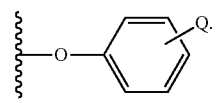

In some embodiments, 'Q' is $NO_2$. In some embodiments, 'Q' is $F_z$. In some embodiments, '$R_1$' is OH. In some embodiments, '$R_1$' is $(OCH_2CH_2)_vOH$. In some embodiments, '$R_1$' is $NH(CH_2)_aOH$. In some embodiments, '$R_1$' is $NH(CH_2CH_2O)_tCH_2CH_2OH$. In some embodiments, 'W' is

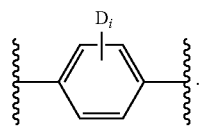

In some embodiments, '$R_2$' is H. In some embodiments, '$R_2$' is $CH_3$. In some embodiments, '$R_3$' is H. In some embodiments, '$R_3$' is $CH_3$. In some embodiments, 'X' is bromine.

In some embodiments, the one or more oligonucleotides are primers. In some embodiments, the one or more oligo- nucleotides comprise a free-amine group that covalently couples with '$R_1$'. In some embodiments, the

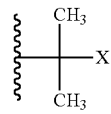

of the bead is generated in a reaction of an amine coupled to the surface of the bead and α-bromoisobutyryl bromide. In some embodiments, the amine is generated from a carbox- ylic acid group coupled to the surface of the bead. In some embodiments, an individual polymer chain of the polymer chains comprises a molecular weight of about 50 kiloDalton (KDa) to about 2500 KDa. In some embodiments, the bead is a magnetic bead. In some embodiments, the method further comprises repeating (a)-(c) for one or more addi- tional beads.

Additional aspects and advantages of the present disclo- sure will become readily apparent to those skilled in this art from the following detailed description, wherein only illus- trative embodiments of the present disclosure are shown and described. As will be realized, the present disclosure is capable of other and different embodiments, and its several details are capable of modifications in various obvious respects, all without departing from the disclosure. Accord- ingly, the drawings and description are to be regarded as illustrative in nature, and not as restrictive.

INCORPORATION BY REFERENCE

All publications, patents, and patent applications men- tioned in this specification are herein incorporated by ref- erence to the same extent as if each individual publication, patent, or patent application was specifically and individu- ally indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed descrip- tion that sets forth illustrative embodiments, in which the principles of the invention are utilized, and the accompany- ing drawings (also "figure" and "FIG." herein), of which:

FIG. 9A shows an example preparation of reactive grafting polymer.

DETAILED DESCRIPTION

Figure 1:
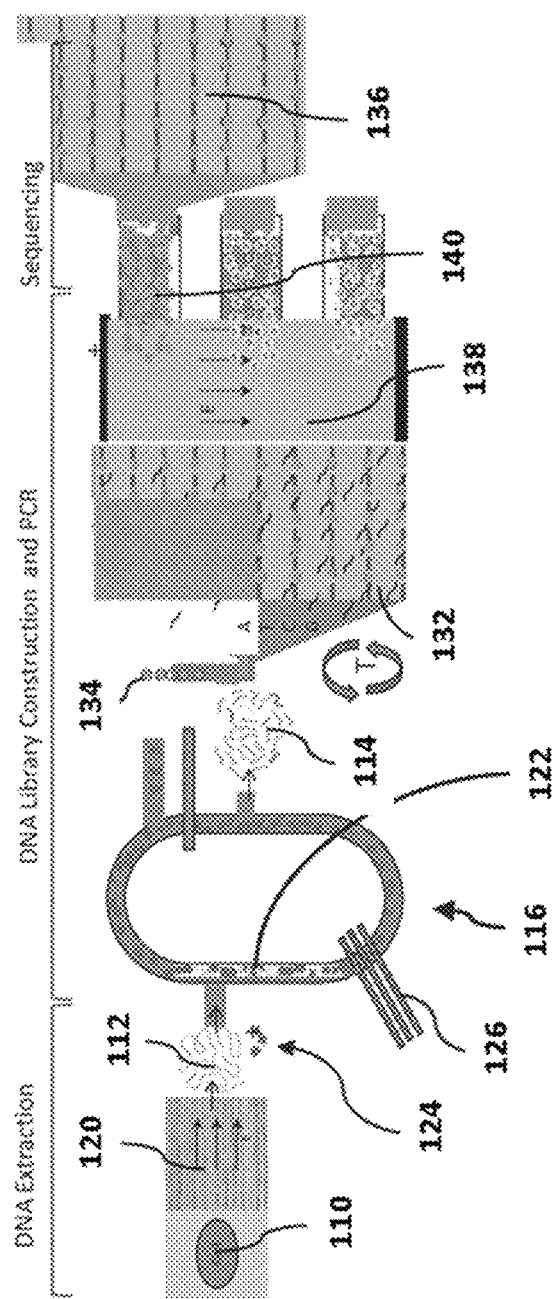
FIG. 1 is a schematic of an integrated sequencing plat- form.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "adjacent to," as used herein, generally refers to next to, in proximity to, or in sensing or electronic vicinity (or proximity) of. For example, a first object adjacent to a second object can be in contact with the second object, or may not be in contact with the second object but may be in proximity to the second object. In some examples, a first object adjacent to a second object is within about 0 micrometers ("microns"), 0.001 microns, 0.01 microns, 0.1 microns, 0.2 microns, 0.3 microns, 0.4 microns, 0.5 microns, 1 micron, 2 microns, 3 microns, 4 microns, 5 microns, 10 microns, or 100 microns of the second object.

The term "nucleic acid," or "polynucleotide," as used herein, generally refers to a molecule comprising one or more nucleic acid subunits, or nucleotides. A nucleic acid may include one or more nucleotides selected from adenosine (A), cytosine (C), guanine (G), thymine (T) and uracil (U), or variants thereof. A nucleotide generally includes a nucleoside and at least 1, 2, 3, 4, 5, 6, 7, 8, 9, 10, or more phosphate ($PO_3$) groups. A nucleotide can include a nucleobase, a five-carbon sugar (either ribose or deoxyribose), and one or more phosphate groups. Ribonucleotides are nucleotides in which the sugar is ribose. Deoxyribonucleotides are nucleotides in which the sugar is deoxyribose. A nucleotide can be a nucleoside monophosphate or a nucleoside polyphosphate. A nucleotide can be a deoxyribonucleoside polyphosphate, such as, e.g., a deoxyribonucleoside triphosphate (dNTP), which can be selected from deoxyadenosine triphosphate (dATP), deoxycytidine triphosphate (dCTP), deoxyguanosine triphosphate (dGTP), uridine triphosphate (dUTP) and deoxythymidine triphosphate (dTTP) dNTPs, that include detectable tags, such as luminescent tags or markers (e.g., fluorophores). A nucleotide can include any subunit that can be incorporated into a growing nucleic acid strand. Such subunit can be an A, C, G, T, or U, or any other subunit that is specific to one or more complementary A, C, G, T or U, or complementary to a purine (e.g., A or G, or variant thereof) or a pyrimidine (e.g., C, T or U, or variant thereof). In some examples, a nucleic acid is deoxyribonucleic acid (DNA), ribonucleic acid (RNA), or derivatives or variants thereof. A nucleic acid may be single-stranded or double stranded. In some cases, a nucleic acid molecule is circular.

The terms "nucleic acid molecule," "nucleic acid sequence," "nucleic acid fragment," "oligonucleotide" and "polynucleotide," as used herein, generally refer to a polynucleotide that may have various lengths, such as either deoxyribonucleotides or ribonucleotides (RNA), or analogs thereof. A nucleic acid molecule can have a length of at least about 100 bases, 200 bases, 300 bases, 400 bases, 500 bases, 1 kilobase (kb), 2 kb, 3, kb, 4 kb, 5 kb, 10 kb, or 50 kb. An oligonucleotide is typically composed of a specific sequence of four nucleotide bases: adenine (A); cytosine (C); guanine (G); and thymine (T) (uracil (U) for thymine (T) when the polynucleotide is RNA). Thus, the term "oligonucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Oligonucleotides may include one or more non-standard nucleotide(s), nucleotide analog(s) and/or modified nucleotides The term "nucleotide," as used herein, generally refers to an organic molecule that serves as the monomer, or subunit, of a nucleic acid molecule, such as a deoxyribonucleic (DNA) molecule or ribonucleic acid (RNA) molecule.

Examples of modified nucleotides include, but are not limited to diaminopurine, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxy succinimide esters (NHS). Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Such alternative base pairs compatible with natural and mutant polymerases for de novo and/or amplification synthesis are described in Betz K, Malyshev D A, Lavergne T, Welte W, Diederichs K, Dwyer T J, Ordoukhanian P, Romesberg F E, Marx A (2012).

The term "polymerase,' as used herein, generally refers to any enzyme capable of catalyzing a polymerization reaction. Examples of polymerases include, without limitation, a nucleic acid polymerase. The polymerase can be naturally occurring or synthesized. An example polymerase is a Φ29 polymerase or derivative thereof. A polymerase can be a polymerization enzyme. In some cases, a transcriptase or a ligase is used (e.g., enzymes which catalyze the formation of a bond). Examples of polymerases include a DNA polymerase, an RNA polymerase, a thermostable polymerase, a wild-type polymerase, a modified polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase, Pwo polymerase, VENT polymerase, DEEPVENT polymerase, EX-Taq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tea polymerase, Tih polymerase, Tfi polymerase, Platinum Taq polymerases, Tbr polymerase, Tfl polymerase, Tth polymerase, Pfutubo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof. In some embodiments, the polymerase is a single subunit polymerase. The polymerase can have high processivity, namely the capability of the polymerase to consecutively incorporate nucleotides into a nucleic acid template without releasing the nucleic acid template.

The term "primer," as used herein, generally refers to a strand of nucleic acid that serves as a starting point for nucleic acid synthesis, such as during a primer extension reaction which may be a component of a nucleic acid amplification reaction. In general, a primer hybridizes to a template strand and nucleotides are added to the end(s) of a primer, sometimes with the aid of a polymerizing enzyme such as a polymerase. In an example, during replication of a DNA sample, an enzyme that catalyzes replication starts replication at the 3'-end of a primer attached to the DNA sample and copies the opposite strand. A primer can have one or more functional groups that can be used to couple the primer to a support or carrier, such as a bead or particle.

The term "subject," as used herein, generally refers to an individual having a biological sample that is undergoing processing or analysis. A subject can be an animal or plant. The subject can be a mammal, such as a human. The subject can have or be suspected of having a disease, such as cancer (e.g., breast cancer, colorectal cancer, lung cancer, skin cancer or cervical cancer) or an infectious disease.

The terms "particle" and "bead" are used interchangeably, and as used herein generally refer to a solid support, which can be approximately spherical and/or small (e.g., less than about 1 mm, less than about 0.1 mm, less than about 0.01 mm, or less than about 0.005 mm in diameter).

The terms "linked to" generally refers to two species that are physically associated with each other. Two species may be linked to each other either directly or indirectly. For example, when a species A is linked to a species B, species A may be directly linked to species B or indirectly linked to species B. Species A may be directly linked to species B through a covalently linkage or a non-covalent linkage (e.g., charge interaction, van der Waals forces, etc.). In some cases, a species A may be indirectly linked to a species B through one or more intermediaries, such as a linker.

Integrated Sequencing Platforms

The present disclosure provides an integrated sequencing platform that can include various components. The integrated sequencing platform can be used in various applications, such as sequencing a nucleic acid sample from a subject.

An integrated sequencing platform may include a nucleic acid (e.g., DNA) extraction system, a library construction system, an amplification system, an enrichment system, and a sequencing system. In some embodiments the systems may be separate and/or in modular format. In some embodiments, the integrated sequencing platform can include one, two, three, four, or all five of these systems. In some cases, the systems can be integrated within a single microfluidic device and/or a single array (e.g., a re-usable array). An example of such an integrated platform is depicted in FIG. 1. Other examples of such integrated sequencing platforms can be found in PCT Patent Application No. PCT/US2011/054769, PCT Patent Application No. PCT/US2012/039880, PCT Patent Application No. PCT/US2012/067645, PCT Patent Application No. PCT/US2014/027544, and PCT Patent Application No. PCT/US2014/069624, each of which is incorporated herein by reference in its entirety.

An integrated system may comprise a library construction system (e.g., nucleic acid library construction system), which may include a fragmentation and/or size selection element. An example of a library construction system is shown in FIG. 1. As shown in FIG. 1, a library construction system may include a nucleic acid (e.g., DNA) fragmentation and size selection element 116. The fragmentation and size selection element 116 can be configured to produce double-stranded nucleic acid fragments, which may or may not have blunted ends, via the elements and methods described below. The fragmentation and size selection element 116 can include one or more microfluidic channels 122 within which nucleic acid may be disposed along with a set of fragmentation beads 124. Nucleic acid 112 collected in a nucleic acid (e.g., DNA) extraction system (shown for example in FIG. 1) can be conveyed or "injected" into the nucleic acid (e.g., DNA) fragmentation and size selection element 116 by any suitable method (e.g., pressurized injection, electrophoretic movement, gravity feed, heat-induced movement, ultrasonic movement and/or the like). Similarly, fragmentation beads 124 can be conveyed into the nucleic acid (e.g., DNA) fragmentation element and size selection element 116 by any suitable method.

The fragmentation element and/or size selection element 116 may include a pump 126 to produce movement of a fluid (e.g., a fluid comprising nucleic acid (e.g., DNA) and fragmentation beads 124) within a microfluidic channel 122. The pump 126 can be, for example, a peristaltic pump. In some embodiments, the pump 126 can include one or more microfluidic elements in fluid communication with the microfluidic channel 122, and may have a flexible side-wall that, when deformed, produces a flow within the microfluidic channel 122. In other embodiments, however, any other suitable mechanism can be used as an alternative or in addition to produce movement fluid within the microfluidic channel 122, with non-limiting examples, that include selective heating and cooling of the fluid, pneumatic pressurization of the microfluidic channel, electrophoretic motion, or the like.

The fragmentation beads 124 can be constructed from any material suitable for separating, cutting and/or otherwise dividing a nucleic acid (e.g., DNA) into nucleic acid fragments (e.g., DNA fragments). In some embodiments, the fragmentation beads 124 can be constructed from glass, polydimethylsiloxane (PDMS), ceramic or the like. Moreover, the fragmentation beads 124 can have any suitable size and/or geometry such that the fragmentation element produces fragments having the desired characteristics (e.g., length, strand characteristics, or the like). For example, in some embodiments, the fragmentation beads 124 can be substantially spherical and can have a diameter of 50 µm or less. In other embodiments, the fragmentation beads can have a diameter of 500 nm or less, or any diameter between 50 µm and 500 nm.

Moreover, the size and/or geometry of the microfluidic channel 122 (e.g., cross-sectional shape, aspect ratio or the like) can be selected such that the movement of the nucleic acid (e.g., DNA) within the microfluidic channel 122 and contact of the nucleic acid with the fragmentation beads 124 fragments (e.g., via shearing) the nucleic acid as desired. In some embodiments, the microfluidic channel 122 may be in the range of 1 to 500 am in hydraulic diameter (e.g., the cross-sectional area of the microfluidic channel 122 can be substantially rectangular, thus the size can be represented as a hydraulic diameter). In other embodiments, the hydraulic diameter of the microfluidic channel 122 can be in the range of 10 to 200 am. In yet other embodiments, the hydraulic diameter of the microfluidic channel 122 can be in the range of 500 nm or less. In other embodiments, the microfluidic channel 122 can have any suitable shape, such as semicircular, oval, tapered or the like. In some embodiments enzymatic polishing of sheared nucleic acid (e.g., DNA) ends can be done such that the ends are blunt ends.

In other embodiments, an enzymatic solution can be conveyed into the microfluidic channel 122 to, at least partially, produce enzymatic fragmentation of nucleic acid (e.g., DNA).

In some embodiments, nucleic acid (e.g., deoxyribonucleic acid (DNA)) amplification and sequencing may be performed sequentially within the same system. In such cases, sample nucleic acid may be associated with a plurality of carriers, such as, for example, beads or other types of particles. In some cases, the carriers may be magnetic carriers, such as, for example, magnetic beads or paramagnetic beads. In some cases, the magnetic carriers can be entered into an array (e.g., a substantially planar array comprising a substantially planar substrate) of magnetic features such that the magnetic carriers are held in place by a localized magnetic field at each position (e.g., pixel) of the array. In some embodiments, carriers (including magnetic carriers) can be held in place at each position of an array (e.g., a substantially planar array) by electrostatic force via one or more electrodes due to the charge of the carrier or the associated nucleic acid. In other embodiments, the carriers can be held in place at each position of the array by physical trenches or wells. In some embodiments, the carriers can be held in place at each position of the array by interaction of a species bound to the carrier with a species bound to the array (e.g., hybridization of oligonucleotides or via ligand-capture moiety pairs). Upon immobilization of the carriers to an array, amplification of the associated nucleic acid and sequencing of the amplified nucleic acid can be completed sequentially or simultaneously.

In some embodiments, carriers may be first entered into an array (e.g., via flow through microfluidic channels associated with the array) and captured by the array. After carrier capture, sample nucleic acid may be contacted with the array (e.g., via flow through microfluidic channels associated with the array) and subsequently captured by the carriers. Capture may occur, for example, via nucleic acids associated with the carriers and capable of hybridizing with the sample nucleic acid. Such nucleic acids may also be used as primers for amplification reactions described elsewhere herein. In some embodiments, nucleic acid to be amplified and/or sequenced is associated with carriers prior to their capture by an array.

Alternatively, a surface of the array (e.g., sensor surface, array substrate surface, etc.) may comprise elements suitable for capturing sample nucleic acid, including nucleic acids capable of hybridizing with the sample nucleic acid. Such nucleic acids may also be capable of serving as primers for amplification reactions described elsewhere herein. Such a configuration may be suitable for amplifying and sequencing a nucleic acid in the absence of a carrier.

In some embodiments, the sample nucleic acid may be provided to an array at extremely dilute concentrations in order to obtain a desired ratio of molecules of sample nucleic acid to carrier. For example, ratios of one molecule of nucleic acid for one carrier (e.g., bead), one molecule of nucleic acid for two carriers, one molecule of nucleic acid for three carriers, one molecule of nucleic acid for five beads, or less, etc may be desired.

During amplification reactions, one or more electrodes at a sensor position of the array may be used for concentration of reagents useful for nucleic acid amplification, forming a "virtual well" associated with a carrier, sensor, or substrate at the array position via an electric field. Virtual wells can permit amplification of nucleic acids at a sensor position without cross-contamination of reactants with those of other sensors of the array. In certain embodiments, amplification within a virtual well can generate a clonal population of nucleic acid associated with a carrier, sensor surface, or substrate associated with the virtual well.

Nucleic acid amplification may be performed in multiple cycles if desired. Once a first round of amplification is completed after contacting an array with sample nucleic acid, an array may be washed in order to remove any unbound amplicons and other reagents in solution. Following washing, a second round of amplification may be completed, by contacting the array with sample nucleic acid and subjecting captured sample nucleic acid to appropriate conditions. Where clonal populations are generated, the sample may bind only to sites (e.g., carriers, sensor surfaces, etc.) not already comprising amplicons, as sites with amplicons from first round of amplification may be fully loaded amplicons. The process may be repeated for any number of amplification cycles until capture sites are exhausted. Utilizing multiple rounds of amplification may help eliminate double Poisson distribution problems and help ensure that each sensor site is associated with only nucleic acid sequence, such as a clonal population of amplicons attached to a carrier (e.g., bead). Such attachment may be direct attachment of an amplicon to the carrier, or attachment of the amplicon of the carrier through a linker, such as a nucleic acid molecule directly bound to the carrier. Moreover, multiple rounds of amplification may also help maximize the use of an array, as each round of amplification can better ensure that all of the pixels of the array of occupied with amplicons for sequencing.

Moreover, during sequencing reactions, one or more of the same electrodes and/or different electrodes may be used to detect a reaction of interest, such as nucleotide incorporation. In some cases, sensing may be completed using a NanoNeedle and/or NanoBridge sensor, or other electrical or optical sensors suitable for detection. A NanoBridge sensor may function as a pH or charge sensor, as described in U.S. Published Patent Application No. US 2012/0138460, titled "BIOSENSOR DEVICES, SYSTEMS AND METHODS THEREFOR", which is incorporated herein by reference in its entirety. A sensor (e.g., NanoNeedle sensor) may function as a charge, conductivity and/or impedance sensor, as described in PCT Patent Application No. PCT/US2011/054769, PCT Patent Application No. PCT/US2012/039880, PCT Patent Application No. PCT/US2012/067645, PCT Patent Application No. PCT/US2014/027544, and PCT Patent Application No. PCT/US2014/069624, each of which is incorporated herein by reference in its entirety. In some embodiments, a sequencing reaction of interest may be DNA sequencing.

The detection may be based on at least one of local pH change, local impedance change, local heat detection, local capacitance change, local charge concentration (or change thereof), and local conductivity change. In some embodiments, detection may be based on a local conductivity change, local impedance change, local capacitance change, local charge concentration (or change thereof) of a carrier, a nucleic acid, or other analyte associated with the carrier and/or a sensor. Such measurements may be made by directly detecting (or detecting signals that are indicative of) a local pH change, local impedance change, local heat detection, local capacitance change, local charge concentration (or change thereof), and local conductivity change, such as local conductivity change of a carrier, a nucleic acid (or other analyte) associated with the carrier and/or a sensor. In some cases, detection occurs within the Debye length (e.g., Debye layer) of (i) a carrier, (ii) a nucleic acid associated with a carrier or sensor, and/or (iii) a sensor. The Debye length can characterize a thickness of a charge or conductivity boundary layer (e.g., Debye layer) around the carrier, nucleic acid associated with the carrier or sensor, and/or sensor. For example, the detection occurs within a Debye layer of the carrier. As another example, the detection occurs within the Debye layer of the sensor (e.g., one or more electrodes of the sensor). As another example, the detection occurs within the Debye layer spanning the sensor and the carrier. Such a sensor configuration is described, for example, in PCT Patent Application No. PCT/US2011/054769, PCT Patent Application No. PCT/US2012/039880, PCT Patent Application No. PCT/US2012/067645, PCT Patent Application No. PCT/US2014/027544, and PCT Patent Application No. PCT/US2014/069624, each of which is incorporated herein by reference in its entirety.

Following the completion of sequencing, carriers/nucleic acids may be dissociated from the array, the carriers and array optionally separated from bound species and washed, and either or both of the carriers and array subsequently re-used for another round of amplification and/or sequencing. Dissociation of a carrier from the array may be completed, for example, by removal/reversal of a magnetic and/or electric field used to hold the carrier in place. In addition or as an alternative, fluid flow and/or other type of field (e.g., external magnetic field, external electric field) capable of exerting forces sufficient for overcoming magnetic and/or electrostatic forces used to hold a carrier in place may also be used to dissociate the carrier from an array. Where nucleic acids are directly associated with the array, in the absence of a carrier, the array may be treated with appropriate reagents or energy (e.g., enzymatic reagents, chemical reagents, thermal energy, etc.) to remove bound nucleic acids from the array. In some cases, though, it may be desirable to remove a carrier or nucleic acid from an array prior to amplification and/or sequencing. Such removal can be achieved in analogous fashion as described herein.

In some embodiments, a combined amplification and sequencing system may comprise a magnetic array that can trap a magnetic bead or particle by magnetic force at a plurality of the array positions. In some cases, a magnetic bead may be a paramagnetic bead. Each of the array positions may also comprise electrodes capable of producing electric fields and/or functioning as sensors. Each magnetic bead or particle can comprise a nucleic acid (e.g., DNA) segment that may be clonally amplified, for example, with the aid of electric fields generated by one or more of the electrodes at each array position.

In some embodiments, a combined amplification and sequencing system may comprise an array of electrodes that can trap a magnetic bead or particle by electrostatic force at a plurality of the array positions. In some cases, a magnetic bead may be a paramagnetic bead. One or more of the same electrodes or different electrodes at each of the array positions may also be capable of producing electric fields and/or functioning as sensors. Each magnetic bead or particle can comprise a nucleic acid (e.g., DNA) segment that may be clonally amplified, for example, with the aid of electric fields generated by one or more of the electrodes at each array position.

An example of a combined amplification and sequencing system and use of the example system is depicted in FIG. 2. As shown in FIG. 2A, the system 200 may include an array on a substrate 201 that can comprise sensors (e.g., nanosensors) 205 sometimes in communication with microfluidic channels defined within the platform. Sensors 205 may be associated with substrate 201, and substrate 201 may also be associated with magnetic 210 and electrode 205 and 207 elements. Magnetic beads may be positioned over the sensors 205 by magnetic 210 or electrode 205 and 207 elements. The magnetic elements may form localized magnetic fields and the electrode elements may form localized electric fields in order to position a carrier at each sensor 205 of the array. Moreover, the magnetic and/or electric fields may create an area of confinement for carriers at each position of the array.

Figure 2A:
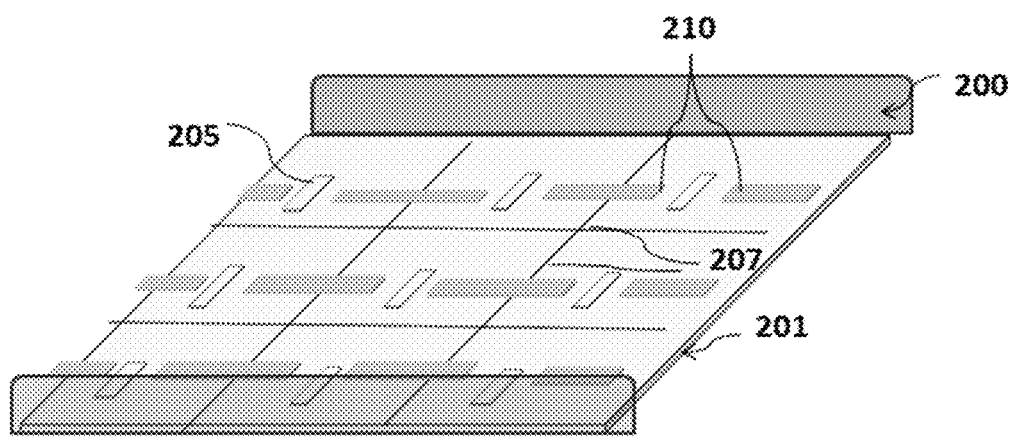
FIG. 2A shows a schematic of an example sensor array.
Figure 2B:
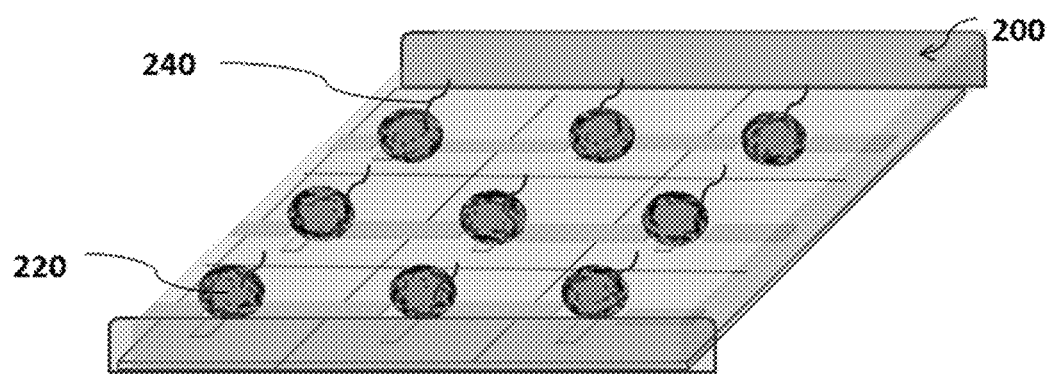
FIG. 2B shows a schematic of an example sensor array with carriers immobilized to the sensor array.

As shown in FIG. 2B, a sample comprising DNA 240 (e.g., DNA fragments) may be conveyed into the system 200. As can be appreciated, DNA 240 is shown as an example and may be any suitable type of nucleic acid, including types of nucleic acids described elsewhere herein. In some cases, introduction of the DNA 240 may be via microfluidic channels associated with the array. As shown, the array may be configured with pre-localized magnetic beads 220 and the magnetic beads may be associated with primers capable of hybridizing with DNA 240, such that DNA 240 is captured by and becomes associated with the beads 220. The magnetic beads 220 may be positioned on the array via the magnetic elements 210 and/or electrode 205 and 207 elements. Alternatively or in addition, primers may be attached, bound, or associated with a sensor at a position of the array and used to trap DNA 240 at the sensor.

Figure 2C:
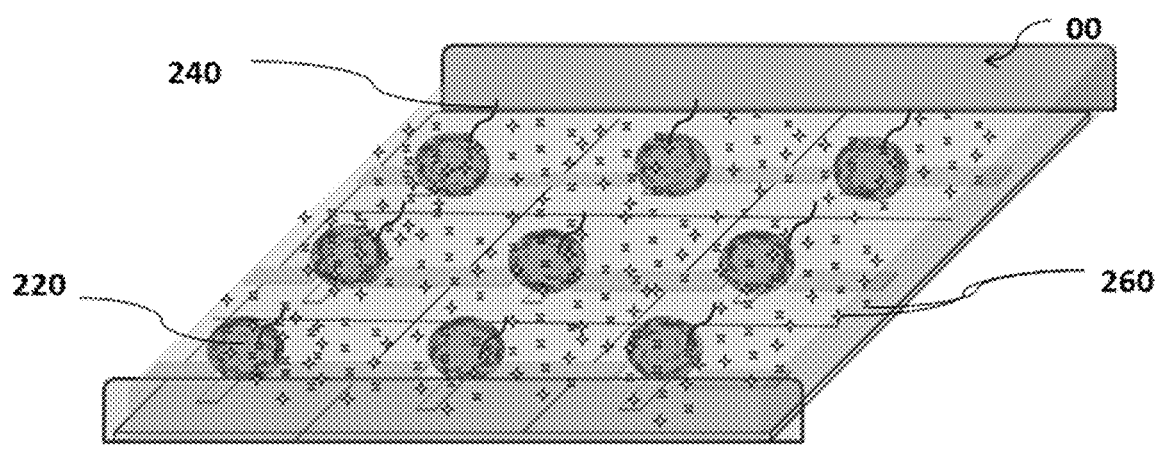
FIG. 2C shows a schematic of an example sensor array with carriers immobilized to the sensor array and in contact with reagents suitable for nucleic acid amplification.

As shown in FIG. 2C, reagents 260 (e.g., polymerase, deoxyribonucleotides (dNTPs), and additional primers) may be simultaneously, previously, or subsequently introduced to the array. In some cases, introduction of the reagents 260 may be via flow through microfluidic channels associated with the array, such that the reagents 260 are contacted with the magnetic beads 220 via flow. Via magnetic and/or electrostatic forces from the appropriate array elements, the magnetic beads 220 can be maintained in the desired position as reagents 260 make contact with the magnetic beads 220 via flow.

Figure 2D:
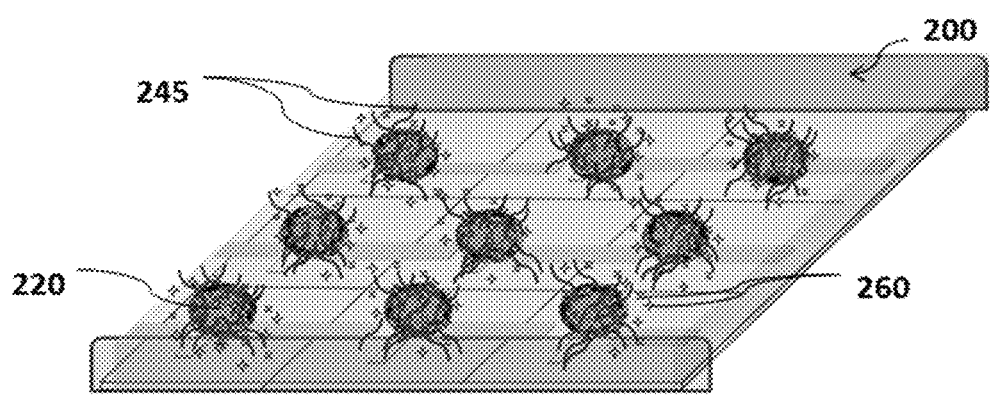
FIG. 2D shows a schematic of an example sensor array where nucleic acid amplification occurs at each array pixel of the sensor array.

As shown in FIG. 2D, the DNA 240 associated with magnetic beads 220 can be clonally amplified to produce amplified DNA 245 and 255 on the surface of the magnetic beads 220. Clonal amplification may be completed using any suitable method including a polymerase chain reaction (PCR), a primer extension reaction, isothermal amplification, or other techniques.

Figure 2E:
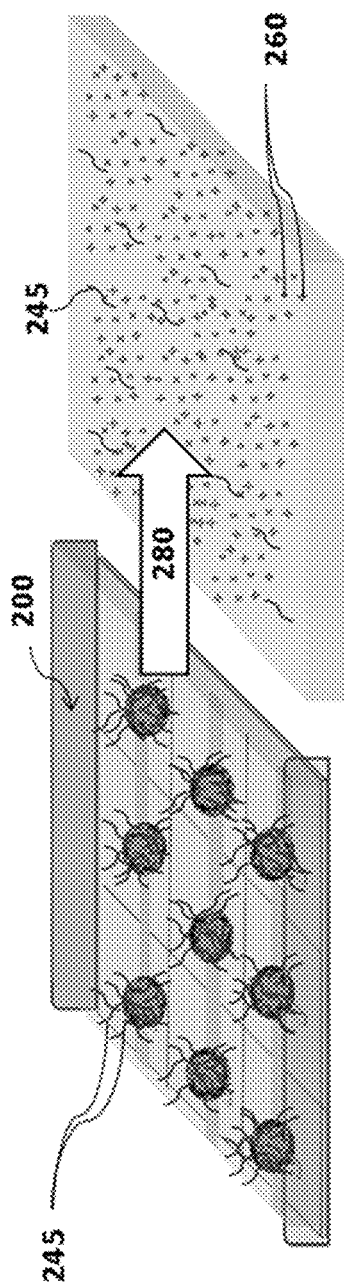
FIG. 2E shows a schematic example of removing reagents from an example sensor array.

As shown in FIG. 2E, the magnetic beads 220 in the array may be washed 280, removing unbound amplicons 245 and reagents 260 in solution following amplification of DNA 240. The result can be magnetic beads 220 comprising clonal sets of amplified DNA 255 associated with array positions. Washing 280 may be completed by any suitable method, such as, for example, washing with a buffer solution at a flow rate sufficient to remove the unbound amplicons 245 and reagents 260 in solution, but insufficient to detach the magnetic beads 220 from their respective positions on the array.

Figure 2F:
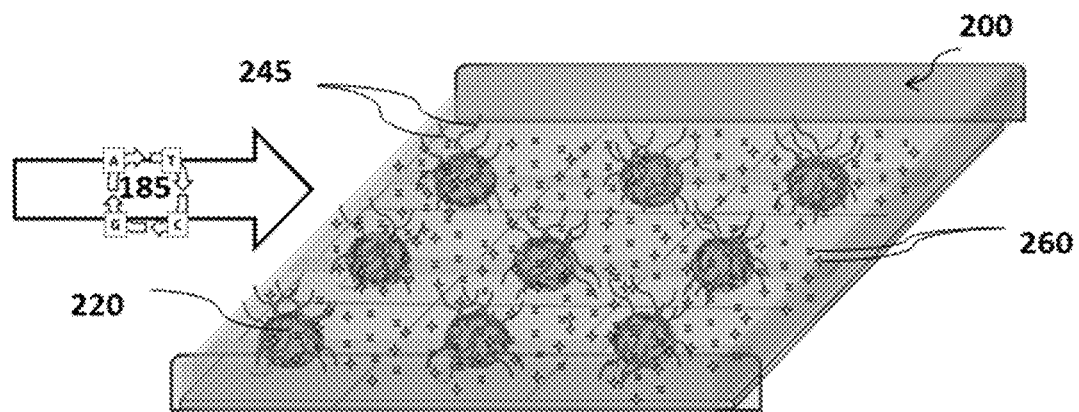
FIG. 2F shows a schematic of an example sensor array where nucleic acids are sequenced at each pixel of the sensor array.

As shown in FIG. 2F, another aliquot of reagents 260 (e.g., polymerase, primers, etc.) and sequential cycles of individual nucleotides 185 may then be contacted (e.g., via flow) with the sensor array, permitting incorporation of the nucleotides into the amplified DNA 255 of magnetic beads 220. nucleotides may be introduced in individual cycles, (e.g., cycle 1=A, cycle 2=T, etc). where there may be a wash step with buffer in between each cycle to help reduce the chance of contamination from unincorporated nucleotides. Polymerase used for the sequencing reaction, may be the same type of polymerase that is used for the amplification reaction, or may be a different type of polymerase, and can be introduced prior to or with introduction of the nucleotides. Detection of the incorporated nucleotides during each cycle can be used to sequence the amplified DNA 255, and, thus, the original sample DNA 240. Detection may occur, for example, via one or both of electrodes 205 and 207. In some cases, electrodes 205 and 207 can detect nucleotide incorporation events by measuring local impedance changes of the magnetic beads 220 and/or the amplified DNA (or other nucleic acid) 255 associated with the magnetic beads 220. Such measurement can be made, for example, by directly measuring local impedance change or measuring a signal that is indicative of local impedance change. In some cases, detection of impedance occurs within the Debye length (e.g., Debye layer) of the magnetic beads 220 and/or the amplified DNA 255 associated with the magnetic beads 220. Nucleotide incorporation events may also be measured by directly measuring a local charge change or local conductivity change or a signal that is indicative of one or more of these as described elsewhere herein. Detection of charge change or conductivity change can occur within the Debye length (e.g., Debye layer) of the magnetic beads 220 and/or amplified DNA 255 associated with the magnetic beads 220.

Additional examples of combined amplification and sequencing systems, for example, may be found in PCT Patent Application No. PCT/US2011/054769, PCT Patent Application No. PCT/US2012/039880, PCT Patent Application No. PCT/US2012/067645, PCT Patent Application No. PCT/US2014/027544, and PCT Patent Application No. PCT/US2014/069624, which are incorporated herein by reference in their entireties.

In some embodiments, after amplification of sample nucleic acid onto carriers, but before sequencing, the carriers subjected to amplification conditions may be sorted in an enrichment system, such as, for example, an electrophoretic sorter, where sorting is achieved via electrophoretic force applied to carriers. The electrophoretic sorter may be part of a system used to conduct amplification and sequencing, or it may be part of a different system. In the electrophoretic sorter, null carriers (e.g., carriers without amplicons), as well as carriers subject to incomplete amplification or those comprising overly short amplicons, can be sorted from carriers comprising the desired amplicons. Additional examples of enrichment systems and electrophoretic sorters are described in PCT Patent Application No. PCT/US2011/054769, PCT Patent Application No. PCT/US2012/039880, PCT Patent Application No. PCT/US2012/067645, PCT Patent Application No. PCT/US2014/027544, and PCT Patent Application No. PCT/US2014/069624, which are incorporated herein by reference in their entireties.

An electrophoretic sorter may comprise channels capable of accepting sorted carriers. Carriers (e.g., beads) with appropriate amounts of amplified product and with amplicons of adequate length may have sufficient charge to be pulled off to an outlet channel. Where the electrophoretic sorter is a separate system, such carriers can be collected from the outlet channel and provided back into the amplification/sequencing system for sequencing, where the steps of introducing reagents and detecting nucleotide incorporation events may occur as described above.

Carriers (e.g., beads) without appropriate amounts of amplified product and/or without amplicons of adequate length may flow through the electrophoretic sorter and, instead, be directed into a waste channel. The carriers may be collected from the waste channel and may be reused for another cycle of amplification or other purpose upon appropriate cleaning to remove any undesirable species. For example, carriers may be washed with a bleaching agent, such as hydrogen peroxide, to help ensure that no contaminants remain on the carriers so that they may be reused.

The arrays and methods described herein can be used for a variety of applications and detection of different biological or biochemical moieties in addition to nucleic acids, such as antibody-antigen detection, protein detection, cell analysis, drug-discovery or screening, ligand, small molecules or other types of analysis. Moreover, the devices and methods described herein are not limited to DNA applications, and may be used for reactions and analysis of interest for RNA, protein detection, small molecules, etc. or other biomolecules.

In addition to sequencing reactions and/or nucleotide incorporation events, arrays and associated sensors may also be useful in sensing other biomolecules (e.g., oligonucleotides, proteins, small molecules, peptides, etc.) and/or reactions of interest using any of the methods and devices described herein, including directly measuring local impedance change, local charge change or local change in conductivity or measuring a signal that is indicative of local impedance change, local charge change or local change in conductivity.

In some embodiments, a sensor may detect a nucleic acid hybridization reaction. For example, a carrier (e.g., a bead) may be linked to a nucleic acid and hybridization of the nucleic acid with another nucleic acid (e.g., a primer or oligonucleotide probe) may be detected. In some embodiments, a sensor may detect a protein-protein interaction. For example, a carrier (e.g., a bead) may be coupled to a protein species (e.g., antibody, antibody fragment, peptide, etc.) capable of binding with an additional protein (e.g., a ligand). Binding of the additional protein to the protein species coupled to the carrier may be detected. Binding of small molecules to species linked to carriers may also be detected. In some cases, a plurality of detection methods may be employed to detect a biomolecule or a biological reaction of interest. Non-limiting examples of additional detection methods include an enzyme-linked immunosorbent assay (ELISA), detection of a tag (e.g., optical dyes, fluorescent dyes), detection of a released or generated species during a biological reaction of interest, etc.

A sensor (e.g., an individual sensor) described herein may be independently addressable. An independently addressable sensor as used herein, can refer to an individual sensor in an array whose response can be independently detected from the responses of other sensors in the array. An independently addressable sensor can also refer to an individual sensor in an array that can be controlled independently from other sensors in the array.

In some embodiments, the nucleic acids are not on carriers (e.g., beads). The nucleic acid can be immobilized directly onto a surface, such as a chip and/or sensor surface. For example, in order to integrate detection on-chip, various types of biomolecules may be patterned on-chip. Methods described herein may be used to covalently immobilize nucleic acids (e.g., DNA) directly onto a microchannel surface, a configuration which may be useful, for example, for an enzyme-linked DNA hybridization assay. In some embodiments, DNA or other nucleic acids can be directly attached to PDMS (polydimethylsiloxane) microfluidic channels, and the use of these PDMS-immobilized capture probes can be used for further immobilization of proteins. Such an approach may be used with other approaches for controlling surface properties of PDMS and the use of surface modifications for immobilization of DNA, RNA, and proteins, such as those described in D. Liu, R. K. Perdue, L. Sun, R. M. Crooks, Langmuir 20, 5905, which is entirely incorporated herein by reference.

In some embodiments, the immobilization of nucleic acid (e.g., DNA) onto a PDMS surface may involve a plurality of steps which can include: plasma-induced oxidation of the PDMS surface, functionalization of the oxidized surface with a silane coupling agent bearing a distal thiol group (mercaptopropylsilane, MPS), and subsequent reaction of the thiol groups with acrylamide-modified DNA. The silanization step can be carried out using a vapor-phase reaction method. The plasma-treated PDMS may be exposed to acid (e.g., HCl) vapor before the MPS vapor, as the acid can act as a catalyst that increases the rate of MPS immobilization on the PDMS surface. Subsequent exposure of the PDMS-linked DNA to its biotinylated complement can provide a platform for immobilization of a protein (e.g., alkaline phosphatase (AP)). PDMS immobilization of species can be compatible with a variety of species, including those described herein. In some cases, PDMS immobilization can provide for immobilizing any suitable oligonucleotide or streptavidin-modified protein onto a PDMS surface.

Devices for Biological Detection

The methods and systems described herein can be performed in a device. The device can perform any one or more of the operations of a method, including but not limited to nucleic acid extraction, fragmentation, library preparation, immobilization (e.g., on a carrier), amplification, confinement, bead enrichment, sequencing, or data analysis and communication.

Figure 3:
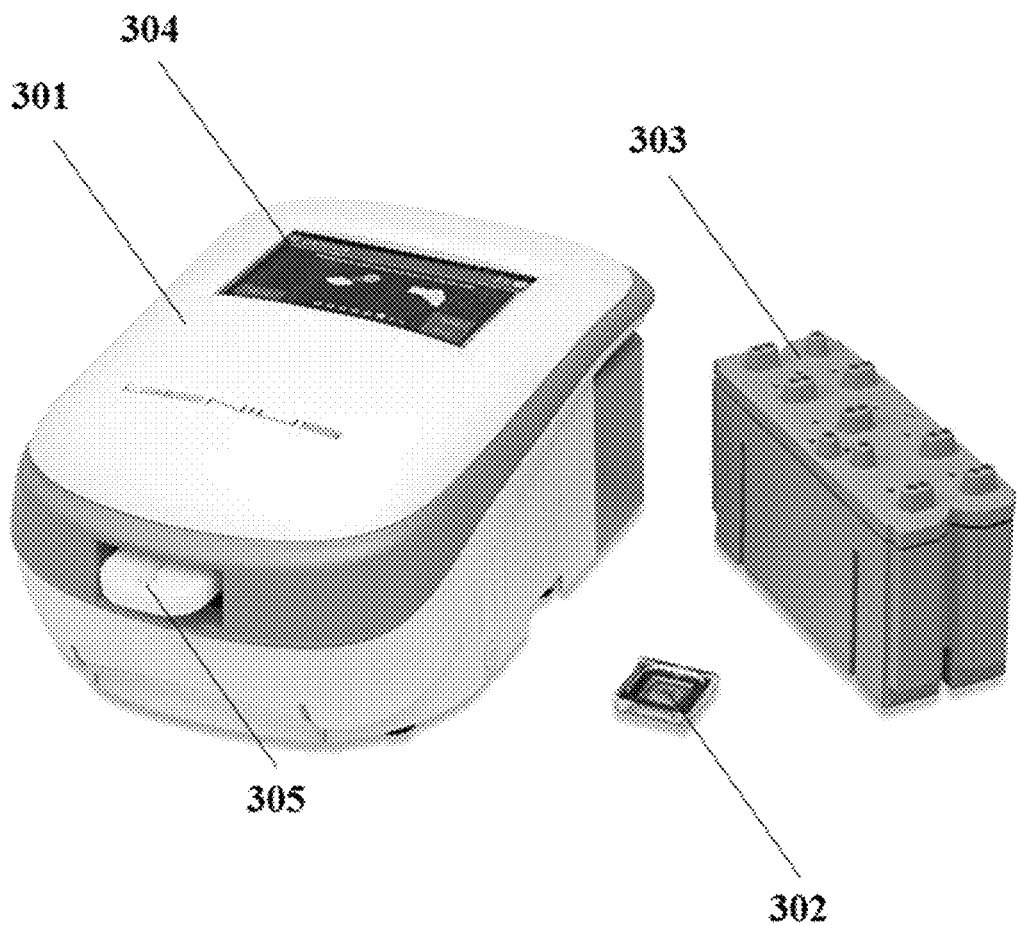
FIG. 3 shows an example biological detection device comprising a housing, a removable chip and a removable reagent reservoir.

FIG. 3 shows a biological detection device 301, a removable chip 302 with an array of sensors, and a reagent reservoir 303 that can be inserted into and removed from the biological detection device 301. In some examples, the reagent reservoir 303 includes primers, nucleotides and polymerase enzymes for nucleic acid sequencing.

The biological detection device 301 can include a screen 304 that can include a user interface, such as a graphical user interface. The screen 304 can enable a user to operate the device 301, such as for nucleic acid sequencing.

The biological detection device 301 can include a port 305 that is configured to accept the removable chip 302. In some examples, upon insertion of the removable chip 302 into the device 301, nucleic acid sequencing can be performed using the array of sensors of the chip 302 and the reagents in the reagent reservoir 303.

An aspect of the present disclosure provides a sensing device comprising a sensing array with a plurality of sensors in a housing, where at least a subset of the plurality of sensors is individually addressable, where each sensor of the plurality is adapted to directly measure an electronic signature associated with a biological species in solution, where the housing has a footprint that is less than or equal to about 250,000 $mm^2$, and where the device has a weight that is less than or equal to about 200 pounds, 175 pounds, 150 pounds, 125 pounds, 100 pounds, 75 pounds, 50 pounds, 25 pounds, 10 pounds or less. In some embodiments, the sensing device does not include wells. As an alternative, the sensing device can include wells. The sensing array can be removable from the housing.

In an embodiment, the device further can comprise a fluid flow path in fluid communication with the sensing array. The fluid flow path can be in communication with a repository comprising one or more reagents for nucleic acid sequencing. In some cases, the fluid flow path can provide beads to the sensing array in an emulsion or, alternatively, without an emulsion.

In some situations, at least some, all or substantially all of the plurality of sensors can be individually addressable. For instance, each sensor of the array can be addressed (e.g., read) separately from other sensors in the array. Each sensor can have one or more electrodes for measuring the electronic signature. Examples of electrodes and electrode configurations that may be employed for use with sensors of the present disclosure are provided in PCT Patent Application No. PCT/US2011/054769, PCT Patent Application No. PCT/US2012/039880, PCT Patent Application No. PCT/US2012/067645, PCT Patent Application No. PCT/US2014/027544, and PCT Patent Application No. PCT/US2014/069624, each of which applications is entirely incorporated herein by reference for all purposes.

In some embodiments, the biological species can be molecular species such as biomolecule, with non-limiting examples that include polynucleotides, polypeptides, proteins, carbohydrates and fatty acids. In some examples, the biological species is a nucleic acid, including any type of nucleic acid described elsewhere herein. In some embodiments, the nucleic acid can be single stranded or double stranded. In some examples, the nucleic acid is circular.

In some embodiments, the sensing array can provide a single-pass bead loading fill factor of at least about 50%, 60%, 70%, 80%, 90%, 95%, 96%, 97%, 98%, 99%, or 99.9%. The fill factor is the percentage of the array having a bead. In some embodiments, the sensing array can provide a nucleic acid sequencing read length of at least about 20 base pairs (bp), 25 bp, 30 bp, 31 bp, 32 bp, 33 bp, 34 bp, 35 bp, 40 bp, 50 bp, 100 bp, 500 bp, 1000 bp, 5000 bp, 10,000 bp, or 100,000 bp with a non-linearity of less than or equal to about 10 bases, 5 bases, 4 bases, 3 bases, 2 bases, 1 base, or 0.5 bases. The read length can be for a nucleic acid homopolymer (e.g., all A, C, T or G).

The sensing array can be part of a chip that is removable from the housing. The chip can be a single-use chip or multi-use chip. The chip can be disposable (e.g., formed of an environmentally friendly material) and/or can be reusable. The sensing array can be substantially planar.

The sensing array can provide a nucleic acid sequencing throughput of at least about 100 base pairs (bp), 500 bp, 1000 bp, 20,000 bp, or 100,000 bp, in a time period that is less than or equal to about 2 days, 1 day, 12 hours, 6 hours, 3 hours, 2 hours, 1 hour, 45 minutes, 30 minutes, 15 minutes, 10 minutes, or 5 minutes. In some cases, a sensing array can be used to perform targeted sequencing and/or whole genome sequencing.

In some situations, the device further comprises a computer processor (or other electronic logic) coupled to the sensing array. The computer processor can be programmed to receive signals from the sensing array that are indicative of a direct electrical signature of the species.

In some cases, the sensing array is adapted for nucleic acid sequencing, proton detection, protein detection, or pathogen detection. The sensing array can be adapted for nucleic acid amplification and/or fluid enrichment.

The device can be portable such that it can be readily transported by a user or a machine. For example, the machine may be transportable on a vehicle. In some examples, the vehicle is an automobile, motorcycle, scooter, helicopter, airplane, truck, military vehicle, spacecraft, or robot.

The measured electronic signature can be an impedance or a change in impedance associated with (i) a bead adjacent to the sensor, (ii) an electrode of the sensor or (iii) a species in a fluid adjacent to the sensor. As an alternative or in addition to, the electronic signature can be a charge or a change in charge associated with (i) a bead or other type of particle adjacent to the sensor, (ii) an electrode of the sensor or (iii) a species in a fluid adjacent to the sensor. As an alternative or in addition to, the electronic signature can be a conductivity or a change in conductivity associated with (i) a bead or other type of particle adjacent to the sensor, (ii) an electrode of the sensor or (iii) a species in a fluid adjacent to the sensor. Various details for measuring an electronic signature can be as described in PCT Patent Application No. PCT/US2011/054769, PCT Patent Application No. PCT/US2012/039880, PCT Patent Application No. PCT/US2012/067645, PCT Patent Application No. PCT/US2014/027544, and PCT Patent Application No. PCT/US2014/069624, each of which applications is entirely incorporated herein by reference for all purposes.

In some cases, the device is part of a system for biological detection. The system can include a single device of multiple devices. Each device can be for the same biological detection or different biological detection. The devices can be in communication with each other through any suitable type of connectivity, including, for example, wireless connectivity.

Another aspect of the present disclosure provides a method for biological detection, comprising providing a sensing device comprising a sensing array with a plurality of sensors in a housing, where at least a subset of the plurality of sensors is individually addressable, where each sensor of the plurality is adapted to directly measure an electronic signature associated with a biological species in solution, where the housing has a footprint that is less than or equal to about 250,000 $mm^2$, 200,000 $mm^2$, 150,000 $mm^2$, 100,000 $mm^2$, 50,000 $mm^2$, 10,000 $mm^2$, 5,000 $mm^2$, or 1,000 $mm^2$ and where the device has a weight that is less than or equal to about 200 pounds, 175 pounds, 150 pounds, 125 pounds, 100 pounds, 75 pounds, 50 pounds, 25 pounds or 10 pounds. Next, a solution comprising the biological species can be directed to the sensing array. The solution can be directed using a fluid flow system comprising, for example, one or more pumps and/or flow actuators. In some embodiments, an electronic signature associated with the biological species can be directly measured using the sensor, as described elsewhere herein. The sensing device can be as described above or elsewhere herein.

In some cases, the sensing device can be provided on a vehicle. The vehicle can be an automobile, motorcycle, scooter, helicopter, airplane, truck, military vehicle, spacecraft, or robot. The vehicle can be moved from a first location to a second location that can be different than the first location. In some situations, while the vehicle is moving from the first location to the second location, (i) the solution is directed to the sensing array and (ii) an electronic signature associated with the biological species is directly measured using the sensor.

The device can be transportable by a user. In some situations, while the user is moving from a first location to a second location, (i) the solution is directed to the sensing array and (ii) an electronic signature associated with the biological species is directly measured using the sensor.

Control Systems

Figure 4:
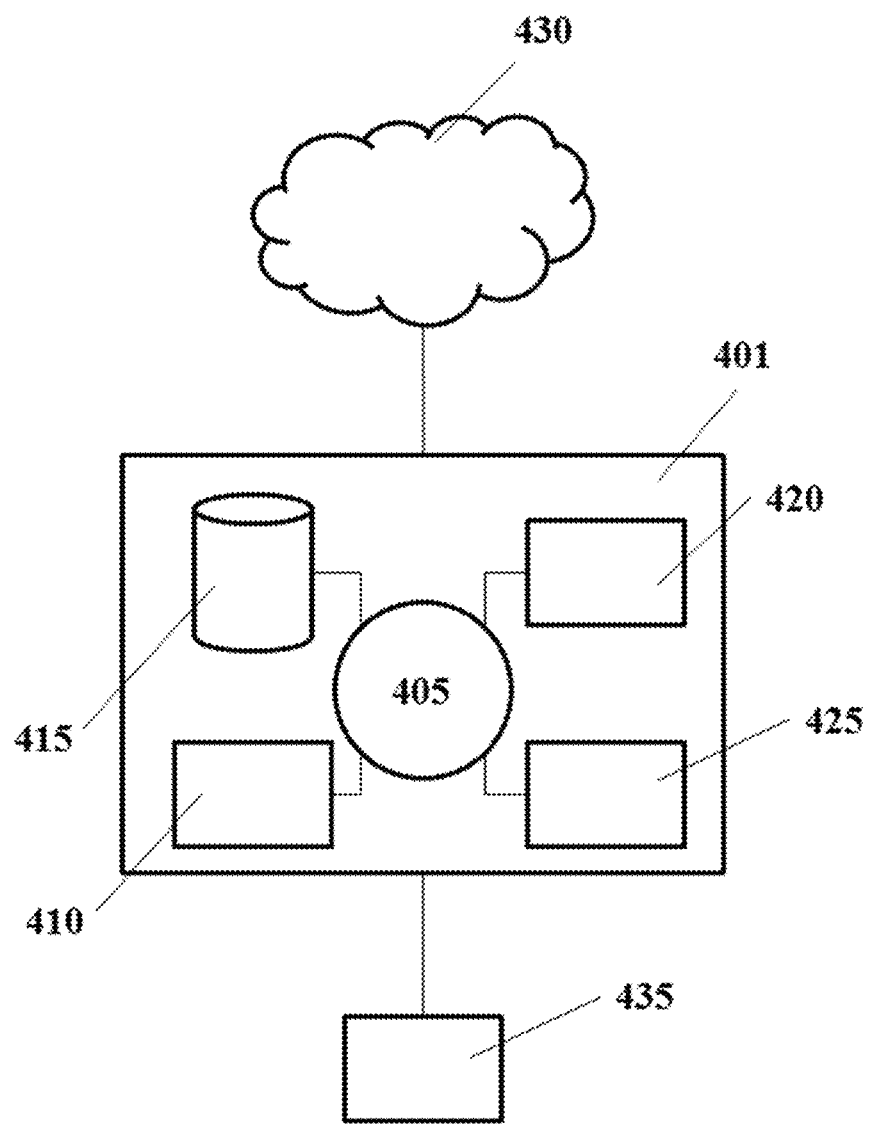
FIG. 4 shows an example computer system that is programmed or otherwise configured to control, regulate or implement devices, systems and methods of the present disclosure.

The present disclosure provides computer control systems that are programmed to implement methods of the disclosure. FIG. 4 shows a computer system 401 that is programmed or otherwise configured for biological detection. The computer system 401 can regulate various aspects of sensing devices, systems and methods of the present disclosure, such as, for example, methods for biological detection. In some embodiments, the computer system 401 can receive signals from a sensor and determine a change in local impedance, local charge and/or local conductivity as described elsewhere herein.

For example, FIG. 4 is an example plot of change in signal (mV, y-axis) versus nucleic acid bases added (x-axis) during a nucleic acid sequencing reaction. The data shows a homopolymer read length of about 33 base pairs.

The computer system 401 can be part of or separate from a device or system for biological detection. In some examples, the system 401 is integrated with a device or system for biological detection, such as a nucleic acid sequencing device. For example, the system 401 can be included in a housing that also contains a sensing array, which can be provided via a removable chip.

The computer system 401 includes a central processing unit (CPU, also "processor" and "computer processor" herein) 405, which can be a single core or multi core processor, or a plurality of processors for parallel processing. The computer system 401 also includes memory or memory location 410 (e.g., random-access memory, read-only memory, flash memory), electronic storage unit 415 (e.g., hard disk), communication interface 420 (e.g., network adapter) for communicating with one or more other systems, and peripheral devices 425, such as cache, other memory, data storage and/or electronic display adapters. The memory 410, storage unit 415, interface 420 and peripheral devices 425 are in communication with the CPU 405 through a communication bus (solid lines), such as a motherboard. The storage unit 415 can be a data storage unit (or data repository) for storing data. The computer system 401 can be operatively coupled to a computer network ("network") 430 with the aid of the communication interface 420. The network 430 can be the Internet, an internet and/or extranet, or an intranet and/or extranet that is in communication with the Internet. The network 430 in some cases is a telecommunication and/or data network. The network 430 can include one or more computer servers, which can enable distributed computing, such as cloud computing. The network 430, in some cases with the aid of the computer system 401, can implement a peer-to-peer network, which may enable devices coupled to the computer system 401 to behave as a client or a server.

The CPU 405 can execute a sequence of machine-readable instructions, which can be embodied in a program or software. The instructions may be stored in a memory location, such as the memory 410. Examples of operations performed by the CPU 405 can include fetch, decode, execute, and writeback.

The storage unit 415 can store files, such as drivers, libraries and saved programs. The storage unit 415 can store user data, e.g., user preferences and user programs. The computer system 401 in some cases can include one or more additional data storage units that are external to the computer system 401, such as located on a remote server that is in communication with the computer system 401 through an intranet or the Internet.

The computer system 401 can communicate with one or more remote computer systems through the network 430. For instance, the computer system 401 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 401 via the network 430.

Methods as described herein can be implemented by way of machine (e.g., computer processor) executable code stored on an electronic storage location of the computer system 401, such as, for example, on the memory 410 or electronic storage unit 415. The machine executable or machine readable code can be provided in the form of software. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

The code can be pre-compiled and configured for use with a machine have a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 401 can include or be in communication with an electronic display 435 that comprises a user interface (UI) for providing, for example, an output or readout of a sensing device of system coupled to the computer system 401. Such readout can include a nucleic acid sequencing readout, such as a sequence of nucleic acid bases that comprise a given nucleic acid sample. Examples of UI's include, without limitation, a graphical user interface (GUI) and web-based user interface. The electronic display 435 can be a computer monitor, or a capacitive or resistive touchscreen.

Devices, methods and systems of the present disclosure can be combined with or modified by other devices, systems and/or methods, such as, for example, those described in PCT Patent Application No. PCT/US2011/054769, PCT Patent Application No. PCT/US2012/039880, PCT Patent Application No. PCT/US2012/067645, PCT Patent Application No. PCT/US2014/027544, and U.S. patent application Ser. No. 13/481,858, each of which applications is entirely incorporated herein by reference for all purposes. These applications provide example devices and methods for directly measuring an electronic signature associated with a biological species in solution, such as impedance or charge measurement, and for making biological measurements for use in, for example, nucleic acid sequencing, including targeted sequencing and whole genome sequencing.

Devices, systems and methods of the present disclosure may be used for various types of measurements, such as pathogen detection, protein detection and nucleic acid sequencing, including measuring a nucleic acid sequence and single-nucleotide polymorphism (SNP) detection. Such methods may be used by a subject, a healthcare provide to diagnose and/or treat the subject, or in forensics analysis.

Beads, Synthesis Thereof and Uses Thereof

Microarrays prepared by direct attachment of biomolecules such as DNA and proteins passively or covalently onto the planar surface of a substrate can have limited use because of the low effective surface density of the attached biomolecules, e.g., oligonucleotide. In addition, the attached biomolecules are typically not utilized efficiently, especially in enzymatic reactions in which the relatively large incoming enzyme molecules can shield off the under laying biomolecules from the outside environments. One solution for this shortcoming, as described herein, is to tether the attached biomolecules away from the surface.

Terpolymers comprising (1) hydrophilic repeat units, (2) thermochemically reactive repeat units, and (3) photochemically reactive repeat units can be used as linkers to conjugate biomolecules onto a planar surface. Under UV radiation the portion of excited photochemically active repeat units abstracts hydrogen from the aliphatic surface of a substrate, resulting in coupling reactions to bind the terpolymer covalently. The thermochemically reactive repeat units can be reactive esters that are capable of forming amide or ester bonds with any biomolecules containing amino or hydroxy groups, respectively. In order to be compatible with aqueous phase reactions, the hydrophilic repeat units are typically greater than about 40 molar % and the photochemically reactive repeat units are typically less than about 4 molar percent. One disadvantage of this system is that the thermochemically reactive repeat units are reactive ester of N-hydroxysuccinimide that is hydrolytically instable.

Copolymer comprising (1) hydrophilic repeat units, and (2) reactive repeat units (e.g., thermochemically reactive repeat units) can be used as linkers to conjugate biomolecules onto a surface (e.g., planar surface). In some cases, the reactive repeat units are reactive esters of fluorinated phenol that are hydrolytically stable. A portion of the reactive ester can react with surface amino groups or hydroxy groups of the substrate attaching the polymer thereon covalently. The remaining reactive ester groups can bind any additional amino- or hydroxy-containing biomolecules. In some cases, the hydrophilic repeating units are greater than about 40 mol %.

Similar copolymers can be used to conjugate glycoconjugates onto magnetic beads containing surface amino groups. The attached glycoconjugates work as capturing probes that bind onto pathogen cells passively. In some instances, the disclosure uses spacing of the attached biomolecules (e.g., nucleic acid, such as single-stranded DNA) to optimize the efficiency of amplification and sequencing on the surface of a magnetic bead.

In some embodiments, homopolymer and copolymers of pentafluorophenyl acrylate are used as linkers to conjugate ssDNA onto magnetic beads. Thermal stability of poly (pentafluorophenyl acrylate) was first report by Yu. P. Gorelov in 1979 ("Thermal decomposition of poly(phenyl acrylate) and poly(pentafluorophenyl acrylates)," Yu. P. Gorelov, et al., Vysokomolekulyarnye Soedineniya, Seriya B: Kratkie Soobshcheniya, Volume: 21, Issue: 6, Pages: 410-13, Journal, 1979), which is herein incorporated by reference in its entirety. Copolymers of pentafluorophenyl methacrylate were reported by Tsutsumi, et al., in 1986 (Halogen-containing polyacrylate derivative," Tsutsumi, et al., EP0230656A, 1986) which is herein incorporated by reference in its entirety.

Figure 6:
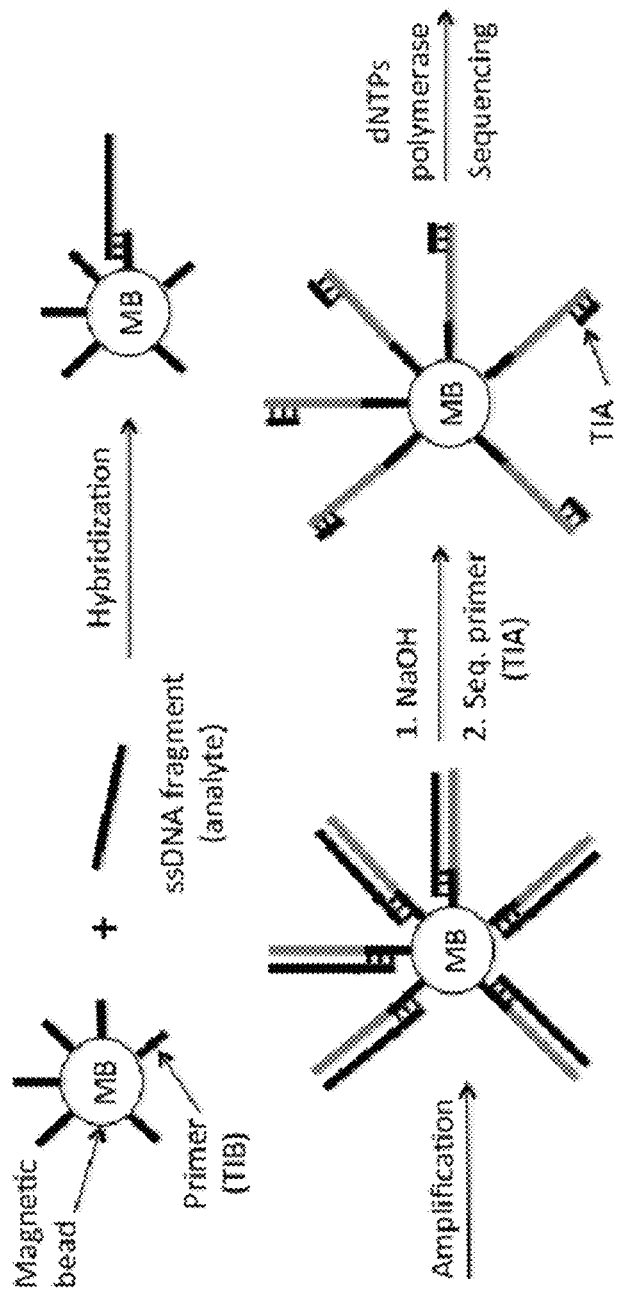
FIG. 6 shows example primer-conjugated magnetic beads for sequencing on surfaces.

FIG. 6 shows example magnetic beads "MB" having primer-conjugated surfaces that can be used for nucleic acid sequencing. The primer-conjugated beads can be annealed with a template (e.g., an analyte from a nucleic acid sample) and the template amplified (e.g., via primer extension reactions in the presence of a polymerase) to give a plurality of amplified templates on the bead surfaces. The amplified templates can then be sequenced by annealing sequencing primers onto the amplified templates and conducting primer extension reactions in the presence of polymerase and dNTPs (FIG. 6). Incorporation of nucleotides to the amplified templates during the primer extension reactions can be measured or detected using a sensor/sensor array and sensing method as described elsewhere herein.

Described herein are methods for the preparation of primer-conjugated beads (e.g., magnetic beads), and their use in nucleic acid sequencing. The methods can comprise (a) aminating carboxyl-bearing beads (e.g., magnetic beads), (b) grafting (e.g., covalently grafting) a pre-fabricated polymer (e.g., copolymer) comprising a plurality of reactive groups to the aminated beads, and (c) covalent attachment of amino- or hydroxy-terminated primers to the pre-fabricated polymer via one or more of the remaining reactive groups. The primer-coupled beads that are generated can then participate in a nucleic acid amplification reaction, whereby a template nucleic acid hybridizes with a primer and amplification proceeds to generate a clonal population of nucleic acid as described elsewhere herein. The clonal nucleic acid population can then be sequenced by serving as templates in a sequencing-by-synthesis reaction as is described elsewhere herein.

In some embodiments, the pre-fabricated polymer can include a repeat unit having a hydrophilic functional group that is different from the reactive groups. In some embodiments, the pre-fabricated polymer may comprise greater than or equal to about 40 mol %, greater than or equal to about 45 mol % greater than or equal to about 50 mol %, greater than or equal to about 55 mol %, greater than or equal to about 60 mol %, greater than or equal to about 65 mol %, greater than or equal to about 70 mol %, greater than or equal to about 75 mol %, greater than or equal to about 80 mol %, greater than or equal to about 85 mol %, greater than or equal to about 90 mol % or greater than or equal to about 95 mol % of the hydrophilic functional group.

Figure 5:
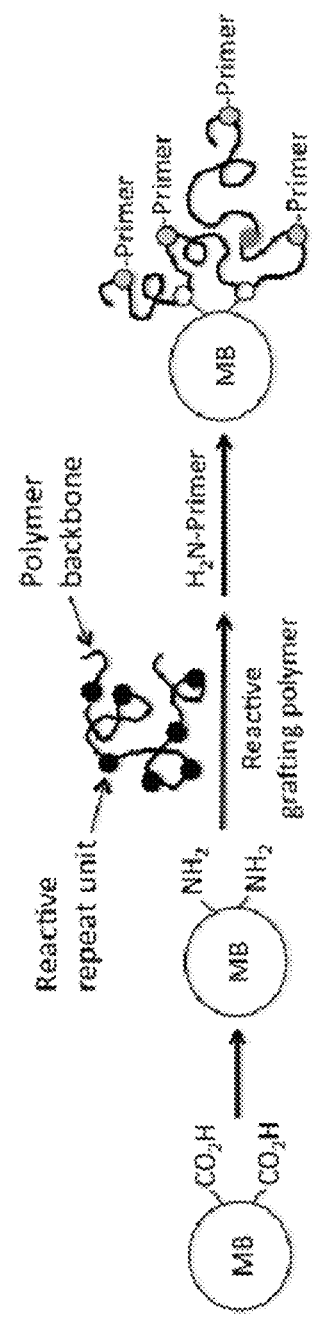
FIG. 5 shows example preparation of primer-conjugated beads.

FIG. 5 shows an example of preparing primer-conjugated magnetic beads. As shown in FIG. 5, magnetic beads "MB" comprise carboxylic acid groups. The carboxylic acid groups can be converted to amino groups as described elsewhere herein (e.g., the scheme shown in FIG. 7). Magnetic beads with surface amino groups are commercially available. However, magnetic beads with surface amino groups can have a relatively short shelf life. For example, surface amino groups can be susceptible to oxidation, which can result in undesirable characteristics leading to non-reproducibility in functionalization.

Primers having free amino or hydroxyl groups (e.g., primers having terminal amino or hydroxyl groups) can then be reacted with additional reactive repeat units on the bead-coupled grafting polymer (via a free amino group or a free hydroxyl group) such that the primers couple to the grafting polymer. As can be appreciated, the example methods shown in FIG. 5 and others described herein may be used to couple primers or any other type of nucleic acids having free amino or hydroxy groups to a surface (including non-magnetic beads) initially having carboxylic acid groups. In some embodiments, the reactive repeat units can comprise one or more reactive functional groups.

Figure 7:
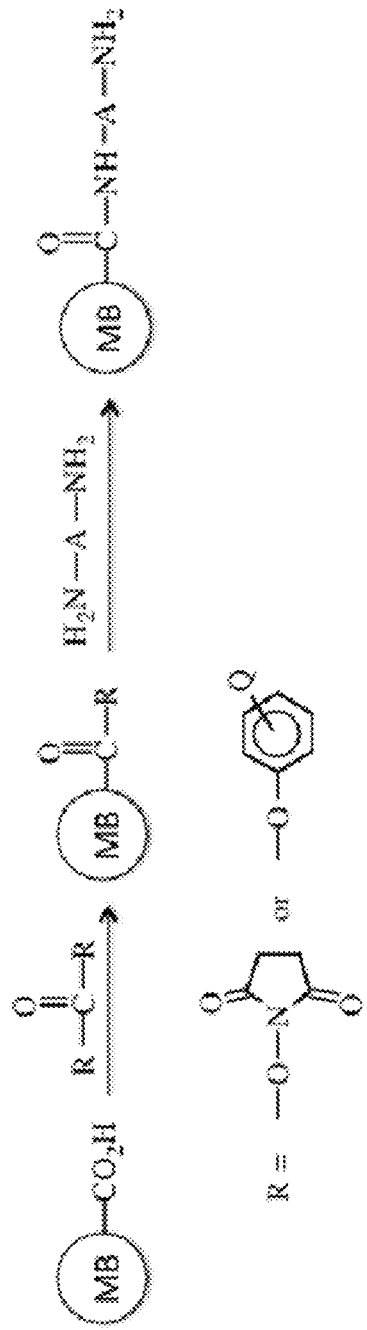
FIG. 7 shows example amination of carboxylic magnetic beads.

As shown in FIG. 7, surface carboxylic acid groups on beads (e.g., magnetic beads, "MB" in FIG. 7) can, in some cases, be activated by N,N-disuccinimidyl carbonate to form reactive esters. In some cases, as shown in FIG. 7, carboxylic acid groups of beads (e.g., magnetic beads) may be activated with bis(4-nitrophenyl), bis(trifluorophenyl), bis (tetrafluorophenyl) and/or bis(pentafluorophenyl) carbonates that form hydrolytically stable, reactive ester groups. Moreover, reactive ester groups can undergo amination via reaction with an excess of a diamine containing a linker "A" (as shown in FIG. 7). Linker A can be, for example, a linear aliphatic linker, or a hydrophilic poly(ethylene oxide) linker. Non-limiting examples of linker species are shown in FIG. 7. The advantages of having a linker can include (a) extending the terminal amino groups further away from the bead surface to be accessible for the incoming pre-fabricated active polymer to be grafted as described below, and (b) in the case of a hydrophilic poly(ethylene oxide) linker, reducing or eliminating non-specific adsorption of other hydrophobic entities.

A reactive grafting polymer, having a polymer backbone and reactive repeat units can be coupled to beads (e.g., magnetic beads) via amino groups thereby coupling the grafting polymer to the surfaces of the beads. In some cases, the grafting polymer is covalently coupled to the surfaces of the beads via an amide bond. In some cases, a pre-fabricated grafting polymer can be prepared by copolymerizing a water-soluble co-monomer with another co-monomer comprising a reactive ester in the presence of an initiator (e.g., a thermal initiator, such as, for example, 2,2'-azobis(2,4-dimethylvaleronitrile), Azobisisobutyronitrile (AIBN) or benzophenone) to generate a reactive grafting polymer (e.g., see examples of FIGS. 8A, 9A and 9C described below). Grafting of the reactive grafting polymer to beads and subsequent primer conjugation to the coupled reactive grafting polymer can be performed by coupling surface amino groups of the beads (e.g., as generated using a method described elsewhere herein) and the reactive grafting polymer in a grafting reaction. During the grafting reaction, a portion of the reactive ester groups of the reactive grafting polymer can react with the surface amino groups of the beads to form multi-point covalent attachment of the grafting polymer to the surface of the beads (e.g., see examples of FIGS. 8B and 9B). The physical entanglement of polymer chains can form 3-dimensional (3D) scaffolds encasing the beads. Primer conjugation can be achieved by reacting remaining reactive ester groups with amino-terminated or hydroxyl-terminated primers to form amide bonds or ester bonds, respectively, between the grafted polymer and the primers. In some cases, residual reactive ester groups remaining after primer coupling can be converted ("Capping" as shown in FIG. 8B) to a hydrophilic amide moiety, such as, for example with ammonium hydroxide in the presence of triethylamine (TEA, $Et_3N$)

In some cases, the composition of a reactive grafting polymer, its molecular weight, and/or the ratio of one repeating subunit to another repeating subunit of the reactive grafting polymer can be controlled. Control of the reactive grafting polymer composition, its molecular weight and/or ratio of its repeating subunits can control the thickness of the polymer when coupled to the surface of a bead (e.g., magnetic bead), can control the spacing of reactive ester groups along the polymer backbone. Such control can later be used in the controlled spacing and amount of conjugated primer. Ample spacing of primers can improve accessibility of the primer to an enzyme (e.g., a polymerase) used in nucleic acid amplification and/or a subsequent sequencing reaction. Improved accessibility can improve both a nucleic acid amplification reaction and a nucleic acid sequencing reaction.

In some cases, the molecular weight of a reactive grafting polymer, including those shown in the examples of FIGS. 8A, 8B, 9A, 9B and 9C can range from 10 kiloDalton (KDa) to 3000 KDa, 50 KDa to 2500 KDa, 100 KDa to 1,500 KDa, or 500 KDa to 1,000 KDa. In some embodiments, the molecular weight of the grafting polymer can be about 10 KDa, 25 KDa, 50 KDa, 100 KDa, 150 KDa, 200 KDa, 250 KDa, 300 KDa, 350 KDa, 400 KDa, 450 KDa, 500 KDa, 550 KDa, 600 KDa, 650 KDa, 700 KDa, 750 KDa, 800 KDa, 850 KDa, 900 KDa, 950 KDa, 1000 KDa, 1050 KDa, 1100 KDa, 1150 KDa, 1200 KDa, 1250 KDa, 1300 KDa, 1350 KDa, 1400 KDa, 1450 KDa, 1500 KDa, 1550 KDa, 1600 KDa, 1650 KDa, 1700 KDa, 1750 KDa, 1800 KDa, 1850 KDa, 1900 KDa, 1950 KDa, 2000 KDa, 2050 KDa, 2100 KDa, 2150 KDa, 2200 KDa, 2250 KDa, 2300 KDa, 2350 KDa, 2400 KDa, 2450 KDa, 2500 KDa, 2550 KDa, 2600 KDa, 2650 KDa, 2700 KDa, 2750 KDa, 2800 KDa, 2850 KDa, 2900 KDa, 2950 KDa or 3000 KDa.

A reactive grafting polymer can comprise a plurality of reactive ester groups randomly distributed along its polymer chain is capable of forming a three dimensional physically entangled polymer scaffold encasing beads (e.g., magnetic beads) having surface amino groups. The polymer scaffold can accommodate relatively high loading of primer. The methods described herein permit tailoring of primer loading by controlling the composition of a reactive grafting copolymer, comprising reactive ester repeat units less than about 60 mol %, less than about 50 mol %, less than about 40 mol %, less than about 30 mol %, less than about 20 mol %, or less than about 10 mol %. The primer loading can also be controlled by the adjusting the amount of reactive grafting copolymer to be grafted onto beads and/or the amount of primer used in a conjugation reaction.

Figure 8A:
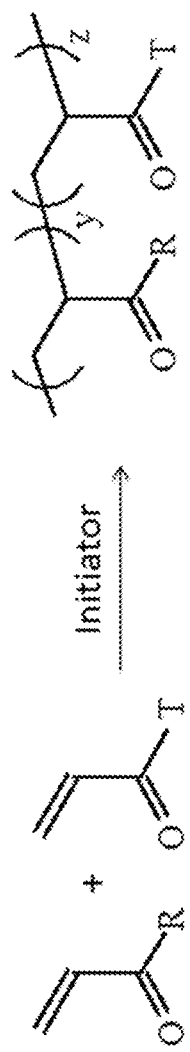
FIG. 8A shows an example preparation of reactive grafting polymer.
Figure 8A:
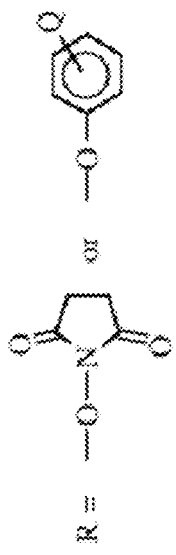
Figure 8B:
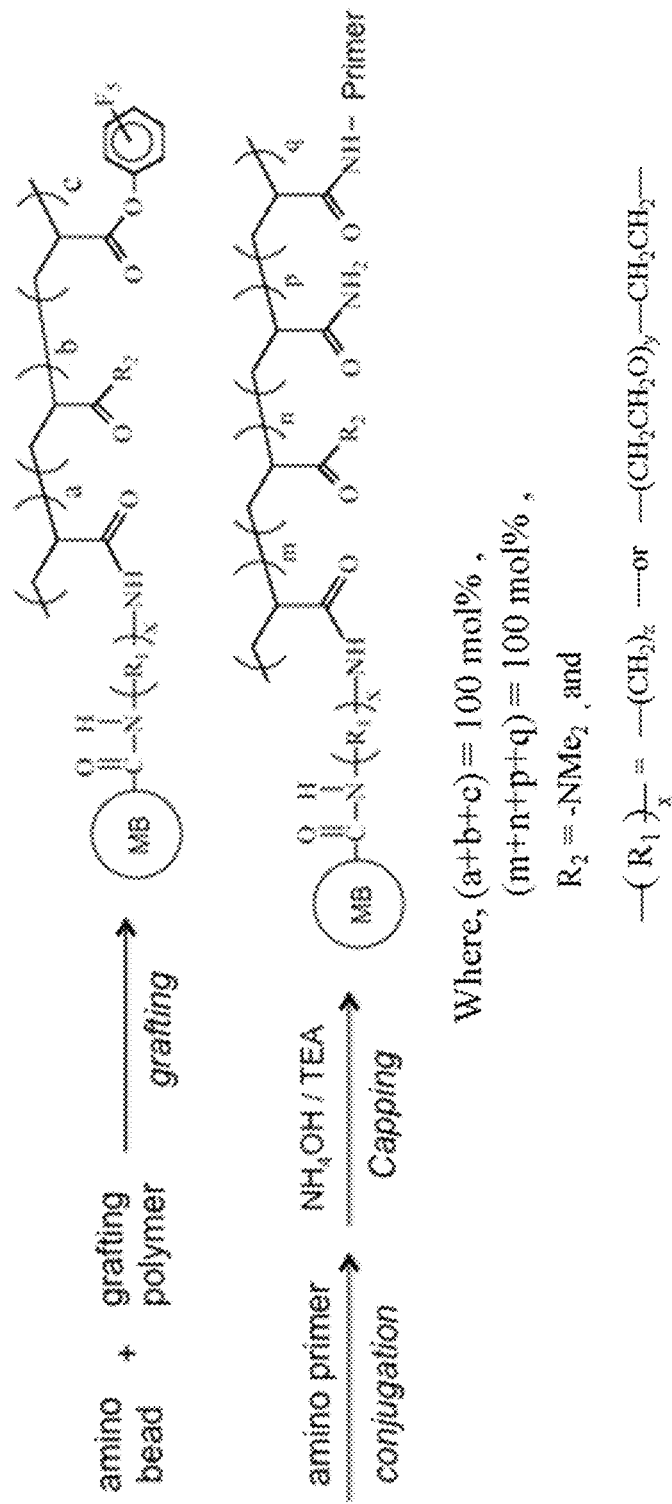
FIG. 8B shows an example grafting of reactive polymer and primer conjugation.

In one example, as illustrated in FIG. 8A, a reactive ester having a reactive "R" group (e.g., N-succinimidyl, 4-nitrophenyl, fluorophenyl, difluorophenyl, trifluorophenyl, tetrafluorophenyl or pentafluorophenyl) can be co-polymerized with a water soluble co-monomer that comprises a "T" group (e.g., —$NH_2$, —$NH(CH_3)$, —$NH(CH_2OH)$, —$NH(CH_2OH)$, —$NH(CH_2CH_2OH)$, —$NMe_2$, —$(CH_2CH_2O)_n$—$CH_3$) in the presence of an initiator (e.g., a thermal initiator, such as, for example, 2,2'-azobis(2,4-dimethylvaleronitrile) to generate a reactive grafting polymer. As shown in FIG. 8A, (y+z)=100 mol %, where y corresponds to the mole percentage of the reactive repeating subunit shown in FIG. 8A and "z" corresponds to the mole percentage of the water-soluble repeating subunit shown in FIG. 8A. In some cases, the y mole percent can range from about 0.1 mol % to about 80 mol %, 0.1 mol % to about 60 mol %, about 1 mol % to about 60 mol %, or about 10 mol % to about 60 mol % with the remaining fraction comprising "z". In some cases, the y mole percent can be less than or equal to about 80 mol %, 75 mol %, 70 mol %, 65 mol %, 60 mol %, 55 mol %, 50 mol %, 45 mol %, 40 mol %, 35 mol %, 30 mol %, 25 mol %, 20 mol % or less with the remaining fraction comprising z. In some cases, the y mole percent is less than or equal to about 60% and the z mole percent is greater than or equal to about 40% as is shown in the example of FIG. 8A.

An example of grafting a reactive grafting polymer, as generated by the example method shown in FIG. 8A, to a bead is schematically depicted in FIG. 8B. As shown in FIG. 8B, a bead (e.g., magnetic bead "MB") comprising surface bound amino groups (e.g., via a linker comprising —$(R_1)_x$, where —$(R_1)_x$ may be, for example, —$(CH_2)_m$ (m=2 to 10) or —$(CH_2CH_2O)_n$—$CH_2CH_2$— (n=1 to 100)) is reacted with a reactive grafting polymer. The reactive grafting polymer can include a reactive ester having a reactive pentafluorophenyl "R" group and a —$NMe_2$ "T" group (shown as "$R_2$") in FIG. 8B. A portion of the reactive pentafluorophenyl groups of the reactive grafting polymer can react with the amino groups of the bead such that the reactive grafting polymer is attached (e.g., covalently attached) to the beads. In a second step, all or a portion of the remaining reactive pentafluorophenyl groups of the reactive grafting polymer can react with amino-bearing or hydroxy-bearing primers such that the primers are attached to the reactive grafting polymer and, thus, the bead. In some cases, remaining reactive pentafluorophenyl groups of the reactive grafting polymer can be "capped" in the presence of ammonium hydroxide and TEA as described elsewhere herein. Moreover, as can be appreciated, the example method shown in FIG. 8B may be used to couple any other type of nucleic acid or other species having free amino or hydroxy groups to a surface (including non-magnetic beads) also having free amino groups and/or hydroxy groups.

In another example, as illustrated in FIG. 9A, a reactive ester having a reactive "R" group (e.g., N-succinimidyl, 4-nitrophenyl, fluorophenyl, difluorophenyl, trifluorophenyl, tetrafluorophenyl or pentafluorophenyl), an "$R_2$" group (e.g., H or $CH_3$) and a "W" group (e.g., a single bond or a phenyl group having a "$D_i$" substituent (e.g., H or $CH_3$)) can be co-polymerized with a water soluble co-monomer that includes a "T" group (e.g., —$NH_2$, —$N(CH_3)_2$, —$NH(CH_3)$, —$NH(CH_2)_t$—OH (t=1 to 4), —$(OCH_2CH_2)_v$—OH (v=1 to 100), —$(OCH_2CH_2)_v$—$CH_3$ (v=1 to 100), —$(OCH_2CH_2)_v$—$OCH_3$ (v=1 to 100) and —$OCH_3$) and an "$R_3$" group (e.g., H or $CH_3$) in the presence of an initiator (e.g., a thermal initiator, such as, for example, 2,2'-azobis(2,4-dimethylvaleronitrile) to generate a reactive grafting polymer. As shown in FIG. 9A, (y+z)=100 mol %, where y corresponds to the mole percentage of the reactive repeating subunit shown in FIG. 9A and "z" corresponds to the mole percentage of the water-soluble repeating subunit shown in FIG. 9A. In some cases, the y mole percent can range from about 0.1 mol % to about 80 mol %, 0.1 mol % to about 60 mol %, about 1 mol % to about 60 mol %, or about 10 mol % to about 60 mol % with the remaining fraction comprising "z". In some cases, the y mole percent can be less than or equal to about 80 mol %, 75 mol %, 70 mol %, 65 mol %, 60 mol %, 55 mol %, 50 mol %, 45 mol %, 40 mol %, 35 mol %, 30 mol %, 25 mol %, 20 mol % or less with the remaining fraction comprising z. In some cases, the y mole percent is less than or equal to about 60% and the z mole percent is greater than or equal to about 40% as is shown in the example of FIG. 9A.

Figure 9B:
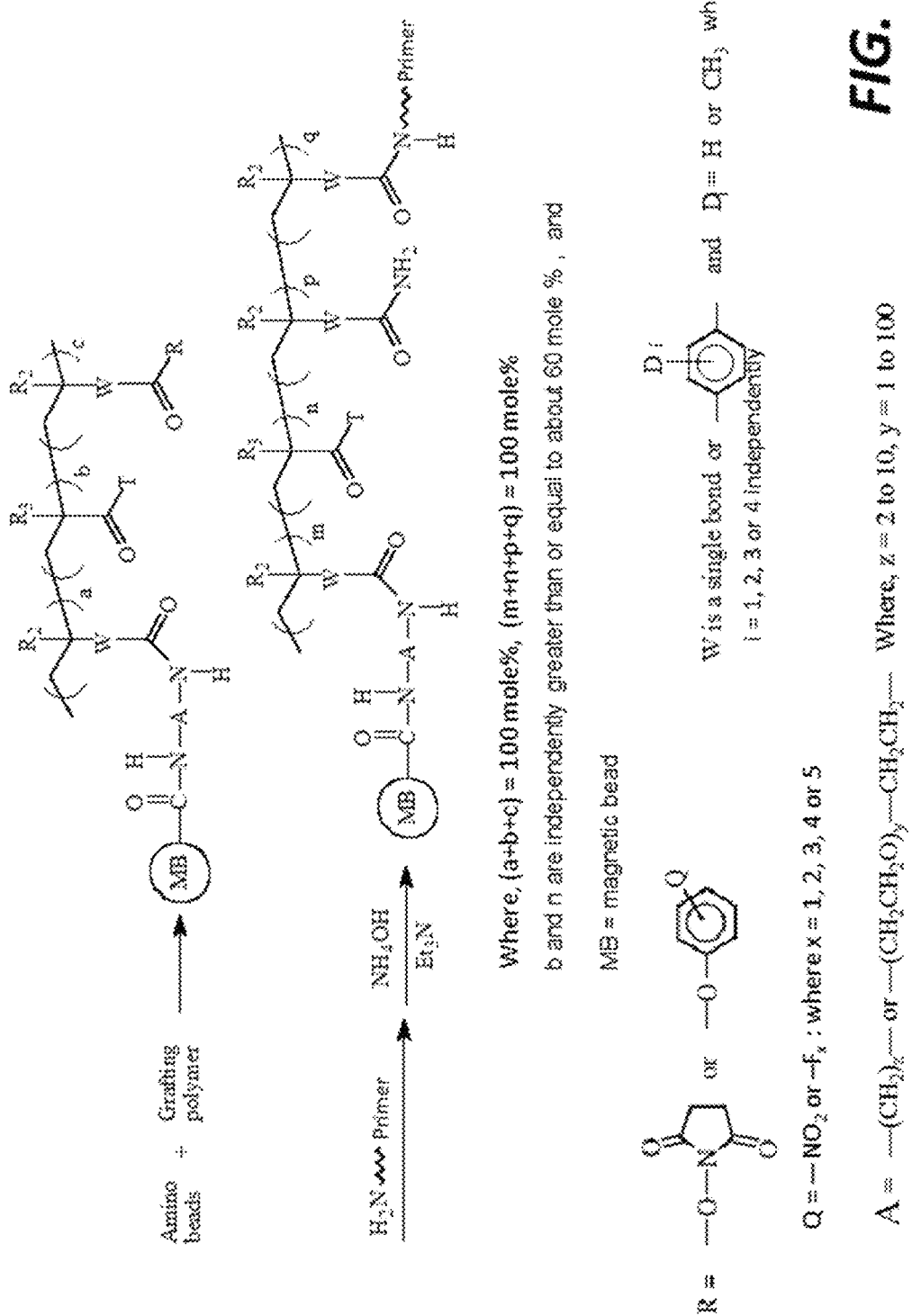
FIG. 9B shows an example grafting of reactive polymer and primer conjugation.

An example of grafting a reactive grafting polymer, as generated by the example method shown in FIG. 9A, to a bead is schematically depicted in FIG. 9B. As shown in FIG. 9B, a bead (e.g., magnetic bead "MB") comprising surface bound amino groups (e.g., via an "A" linker comprising, for example, —$(CH_2)_m$ (m=2 to 10) or —$(CH_2CH_2O)_n$—$CH_2CH_2$— (n=1 to 100) is reacted with a reactive grafting polymer. The reactive grafting polymer can include a reactive ester having a reactive "R" group and "T" group in FIG. 9B. A portion of the reactive R groups of the reactive grafting polymer can react with the amino groups of the bead such that the reactive grafting polymer is attached to the beads. In a second step, all or a portion of the remaining reactive R groups of the reactive grafting polymer can react with amino-bearing or hydroxy-bearing primers such that the primers are attached to the reactive grafting polymer and, thus, the bead. In some cases, remaining reactive R groups of the reactive grafting polymer can be "capped" in the presence of ammonium hydroxide and TEA as described elsewhere herein. Moreover, as can be appreciated, the example method shown in FIG. 9B may be used to couple any other type of nucleic acid or other species having free amino or hydroxy groups to a surface (including non-magnetic beads) also having free amino groups and/or hydroxy groups.

Figure 9C:
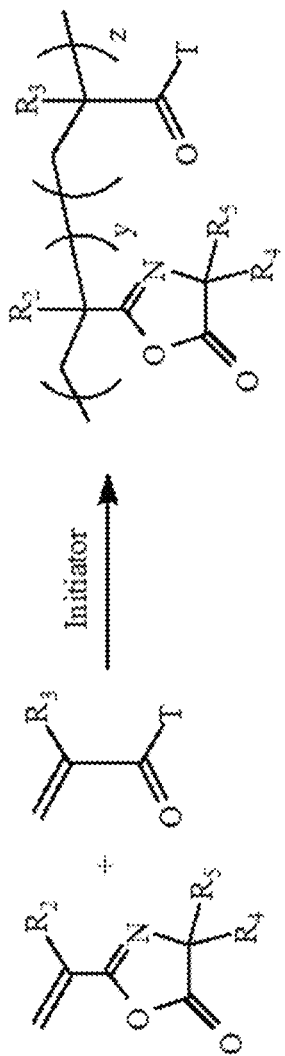
FIG. 9C shows an example preparation of a grafting polymer.

In another example, as illustrated in FIG. 9C, a reactive repeat unit having a reactive azlactone group (comprising "$R_4$" and "$R_5$" groups, which can independently be, for example, H or $CH_3$) and "$R_2$" group (e.g., H or $CH_3$) can be co-polymerized with a water-soluble co-monomer that includes a "T" group (e.g., —$NH_2$, —$NH(CH_3)$, —$N(CH_3)_2$, —$NH(CH_2)_t$—OH (t=1 to 4), —$(OCH_2CH_2)_v$—OH (v=1 to 100), —$(OCH_2CH_2)_v$—$OCH_3$ (v=1 to 100), —$(OCH_2CH_2)_v$—$CH_3$ (v=1 to 100) and —$OCH_3$)) and an "$R_3$" group (e.g., H or $CH_3$) in the presence of an initiator (e.g., a thermal initiator, such as, for example, Azobisisobutyronitrile (AIBN) or benzophenone) to generate a reactive grafting polymer. As shown in FIG. 9C, (y+z)=100 mol %, where y corresponds to the mole percentage of the reactive repeating subunit shown in FIG. 9C and "z" corresponds to the mole percentage of the water-soluble repeating subunit shown in FIG. 9C. In some cases, the y mole percent can range from about 0.1 mol % to about 80 mol %, 0.1 mol % to about 60 mol %, about 1 mol % to about 60 mol %, or about 10 mol % to about 60 mol % with the remaining fraction comprising "z". In some cases, the y mole percent can be less than or equal to about 80 mol %, 75 mol %, 70 mol %, 65 mol %, 60 mol %, 55 mol %, 50 mol %, 45 mol %, 40 mol %, 35 mol %, 30 mol %, 25 mol %, 20 mol % or less with the remaining fraction comprising z. In some cases, the y mole percent is less than or equal to about 60% and the z mole percent is greater than or equal to about 40% as shown in the example of FIG. 9C.

The grafting polymer shown in FIG. 9C can be coupled to an amino-bearing particle via reaction of one or more bead amino groups with a portion of the reactive azlactone group of the grafting polymer. All or a portion of the remaining reactive azlactone groups of the reactive grafting polymer can react with amino-bearing or hydroxy-bearing primers such that the primers are attached to the reactive grafting polymer and, thus, the bead. In some cases, remaining reactive azlactone groups of the reactive grafting polymer can be "capped" in the presence of ammonium hydroxide and TEA as described elsewhere herein. Moreover, as can be appreciated, the grafting polymer shown in FIG. 9C may be used to couple any other type of nucleic acid or other species having free amino or hydroxy groups to a surface (including non-magnetic beads) also having free amino groups and/or hydroxy groups.

Figure 10:
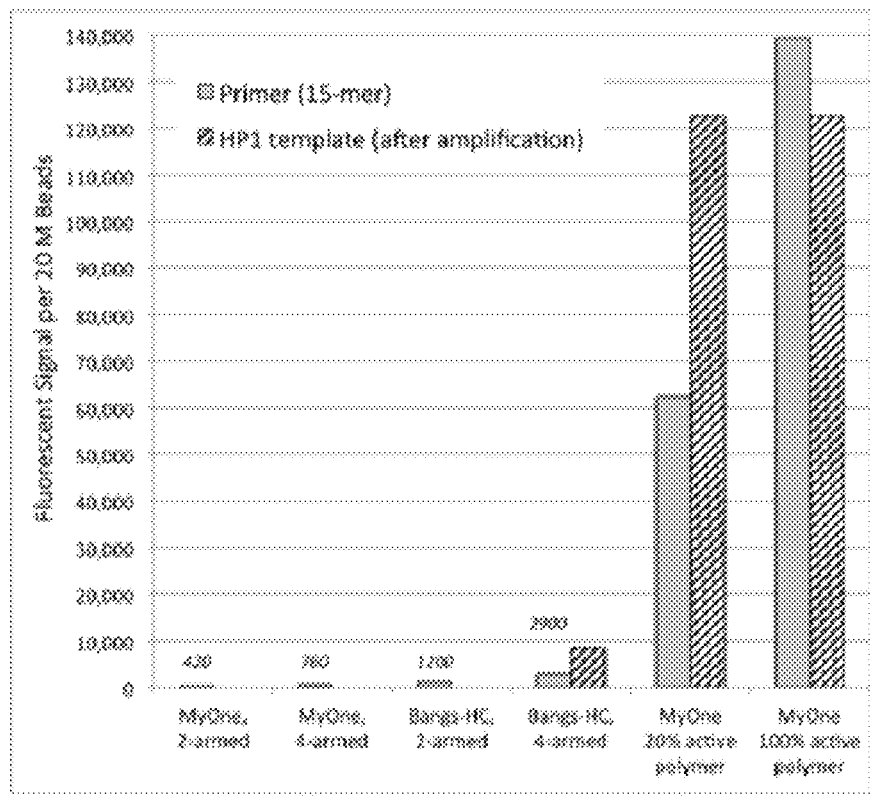
FIG. 10 shows data depicting example primer loading on polymer-grafted magnetic beads.

FIG. 10 compares an example of the primer loading described herein with those prepared by conjugating the same primer via 2-armed and 4-armed poly(ethylene oxide) amine, PEG-NH$_2$, linkers having molecular weight of 2,000 Da onto carboxylic magnetic beads, obtained from Life Technologies (MyOne) and Bangs (Pro-Mag). The 2-armed and 4-armed PEG linkers attach themselves to the amino beads through mono-valent attachment (single-point), resulting in subsequent conjugation of primer in a close-to 2D fashion. This type of conjugation gives primer loading ranging from 400 to 3000 fluorescent signals per 200 million of conjugated beads. The methods described herein conjugate primers onto a 3D scaffold, resulting in fluorescent signals 150× to 350× higher.

FIG. 10 also shows an example of primer loading on polymer-grafted magnetic beads. In addition, as illustrated in FIG. 10, high spatially spaced primer conjugation prepared with 20% active polymer (e.g., y=20 mol % in FIG. 8A) can be result in high HP1 (template) to primer ratio of 1.96 (FIG. 10). On the contrary, high loading of primer conjugation prepared with 100% active polymer (e.g., z=100 mol % in FIG. 8A) can give low HP1 to primer ratio of 0.88 or lower (FIG. 10). In some cases, the former are beneficial for sequencing.

Figure 11:
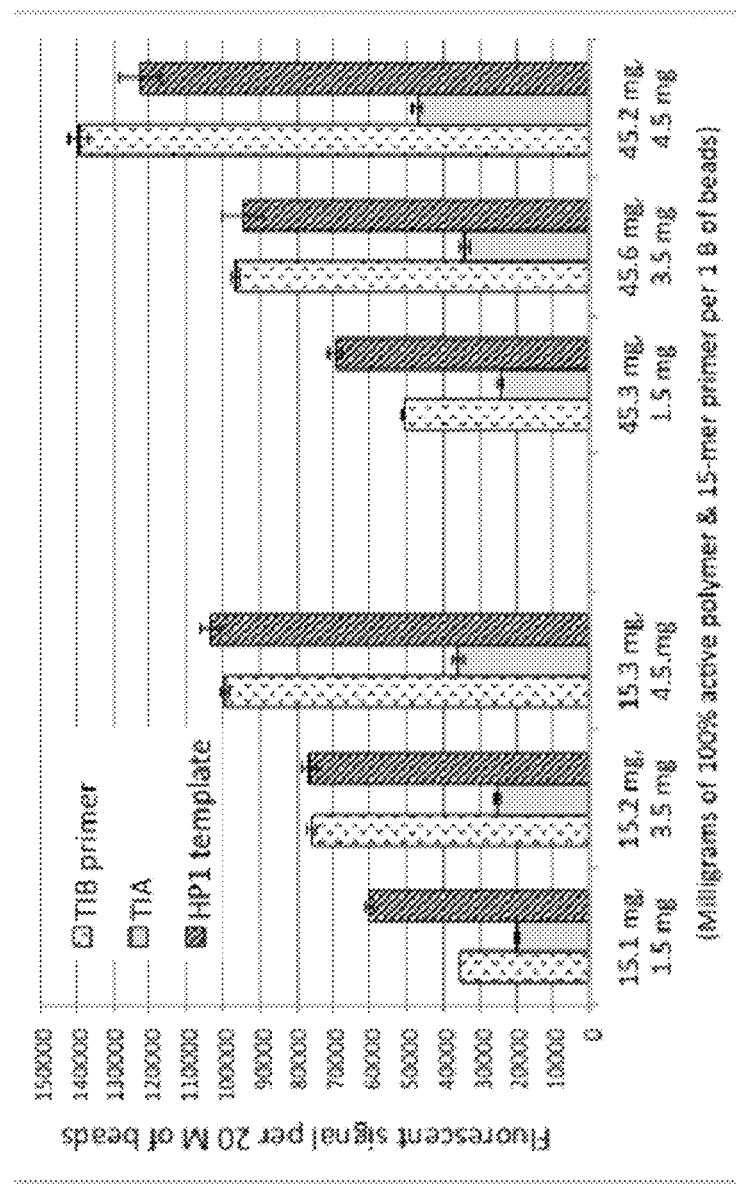
FIG. 11 shows example loading effects of 100% active polymer and 15-mer primer on amplification.

FIG. 11 depicts an example of the loading effects of 100% reactive graft polymer and 15-mer primer on the preparation of primer-conjugated magnetic beads generated with aminated MyOne beads, previously prepared as illustrated in FIG. 7. The increases of 100% active graft polymer and 15-mer primer are followed by the increases of conjugated primer (TIB) of the bead surface and the HP1/TIB ratio (FIG. 11). After passing a threshold, the increases of 100% active graft polymer and primer can be followed by lowering of the HP1/TIB ratio. Without being bound by any particular theory, this effect can be explained by the overcrowding of the primers and templates prohibiting the incoming enzyme from utilizing the buried TIB for amplification.

Figure 12:
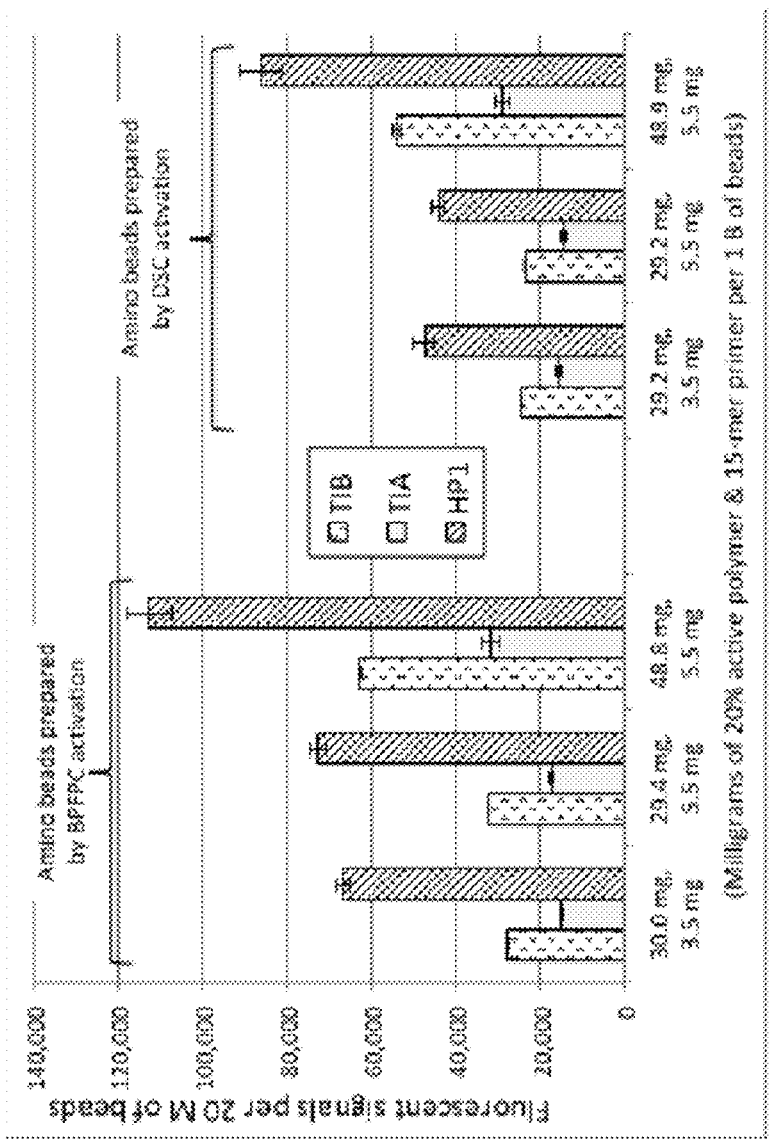
FIG. 12 shows example loading effects of 20% active polymer and 15-mer primer on amplification.

FIG. 11 shows example loading effects of 100% active polymer and 15-mer primer on amplification. The same trend is observed as illustrated in the example of FIG. 12 when 20% active graft polymer and 15-mer primer are used for the preparation of primer-conjugated magnetic beads generated with aminated MyOne beads, previously prepared by using bis(pentafluorophenyl) carbonate (BPFPC) and disuccinimidyl carbonate, DSC (FIG. 7) as activation agents. Since the primers are spatially separated along the polymer chain of the 20% active polymer, the conjugated primers can be efficiently utilized in amplification and thus can result in favorable ratios of HP1/TIB.

FIG. 12 shows example loading effects of 20% active polymer and 15-mer primer on amplification. In short, described herein are techniques to increase and control the degree of primer conjugation with a 3D polymer scaffold covalently attached on the surface of a magnetic bead. By spacing the primers spatially, high ratio of template (e.g., HP1) to primer (e.g., TIB primer) can be obtained after amplification.

The loading of sequencing templates via an amplification reaction can be measured as a ratio of signal obtained from label (e.g., a fluorescent dye) used to detect template and signal obtained from label (e.g., a fluorescent dye) used to detect primer after an amplification reaction. In some cases, the ratio of detected signal for template (e.g., via a label associated with HP1 template) to detected signal for primer (e.g., via a label associated with TIB primer) after bead amplification is at least about 1.1, at least about 1.2, at least about 1.3, at least about 1.4, at least about 1.5, at least about 1.6, at least about 1.7, at least about 1.8, at least about 1.9, at least about 2.0, at least about 2.1, at least about 2.2, at least about 2.3, at least about 2.4, at least about 2.5, at least about 2.6, at least about 2.7, at least about 2.8, at least about 3.0, at least about 4.0, at least about 5.0 or at least about 6.0. In some cases, over-loaded primers on magnetic beads are not generally accessible during amplification, resulting in a detected signal for template to detected signal to primer ratio of less than 1.

Polyethylene Glycol (PEG) Beads

Coated magnetic particles can be useful carriers of molecules, as they can be spatially manipulated by magnetic fields. This property can enable their rapid separation from reaction mixtures and their dispersal over magnetic arrays. Coated magnetic particles are commercially available, and the methods described herein for changing the type of coating can be used to manipulate the properties of the particles in useful ways. In some cases, particles are coated with hydrophobic coatings or hydrophilic coatings.

Hydrophilic coatings containing hydroxyl, carboxyl, and/or amine functional groups can impart hydrophilicity and can be used as handles (reactive groups) for attaching other useful functionality. Less hydrophilic handles including vinyl, acetylenic and/or azido groups can also be used in coating, as described herein.

Magnetic particles with amine, hydroxyl, and carboxyl functional coatings are commercially available. These coating can take different forms that can be characterized by their size and valency. In some embodiments, the methods of the present disclosure use beads (e.g., with a diameter of about 1 micron) coated with poly acrylic acid. Examples of these beads are available from Life Technologies™ (MyOne carboxy beads) and Bangs Laboratories (PMC1HC beads). The particular way in which primer is attached to these beads can be important for nucleic acid sequencing, as described herein.

Single stranded oligonucleotides, such as a primer, can be attached to the beads via an amino-PEG-carboxy linker (e.g., see examples in FIGS. 13 and 14 and described below). In some cases, the PEG portion of the linker is of a discrete length (e.g., a single molecular weight). Such linkers are commercially available from Quanta BioDesign and are referred to as "dPEG™" or "discrete PEG" linkers (e.g., amino-dPEG24-carboxy). The number of repeat units of a PEG (including a dPEG) can be any suitable number including about 5, about 10, about 12, about 15, about 20, about 24, about 30, about 40, about 50, about 60, about 70, about 80, about 90, about 100, about 120, about 140, about 160, about 180, about 200, or more. In some cases, the number of repeat units of a PEG (including a dPEG) is at least about 5, at least about 10, at least about 12, at least about 15, at least about 20, at least about 24, at least about 30, at least about 40, at least about 50, at least about 60, at least about 70, at least about 80, at least about 90, at least about 100, at least about 120, at least about 140, at least about 160, at least about 180, at least about 200, or more. In some cases, the number of repeat units of a PEG (including a dPEG) is at most about 5, at most about 10, at most about 12, at most about 15, at most about 20, at most about 24, at most about 30, at most about 40, at most about 50, at most about 60, at most about 70, at most about 80, at most about 90, at most about 100, at most about 120, at most about 140, at most about 160, at most about 180, or at most about 200.

The amino-PEG-carboxylate linker can be attached to the bead by converting the carboxylates of the bead to NHS esters with disuccinimidyl carbonate in anhydrous NMP with tributylamine as the base. The beads can be washed (e.g., one time with DI water) (e.g., at a concentration of 1-10 mgs beads per ml). In some cases, the beads are washed (e.g., four times) with anhydrous NMP (e.g., at a concentration of 1-10 mg of beads per ml). This reaction can be performed at about 5% weight per volume DSC and 5% v/v tributylamine for two hours at 20 C (e.g., with 1-10 mgs of beads per ml of 5% DSC/NMP solution). The beads can then be washed (e.g., four times) with anhydrous DMSO (e.g., 1-10 mg of beads per ml of DMSO). The bead can then be treated with a large molar excess (e.g., 1-3 mgs per mg of beads) of amino-PEG-carboxylate (e.g., as a 10% w/v solution) in anhydrous DMSO with (e.g., 10% w/V) tributylamine as the base (e.g., at room temperature for 16 hours (hrs.)). The dPEG/DMSO solution can then be removed and the beads can be treated with a (e.g., IM) sodium hydroxide (NaOH) solution (e.g., for 20 to 60 minutes at 20 degrees). The beads can then be washed (e.g., 4 times) with water (e.g., 1-10 mg of beads per ml), and stored in water (e.g., at a concentration of 1-10 mg of beads per ml).

The primer can then be conjugated to the amino-PEG-carboxylate linker. The beads with linker can be washed with anhydrous NMP (e.g., 4 times at a concentration of 1-10 mg per ml). They can then be converted to the NHS ester form (e.g., by treatment with a 5% w/v solution of DSC in anhydrous NMP, 5% w/v tributylamine, 20 C, for 2 hrs). The beads can then be washed (e.g., 4 times with anhydrous DMSO, 1-10 mg of beads per ml of anhydrous DMSO). The beads can then be treated with a (e.g., 10% w/v) solution of tetrabutylammonium exchanged primer in anhydrous DMSO (e.g., 10% w/v tributylamine, at 20 C for 16 hrs, at a concentration of 1 mg of beads per 30 ul of primer/DMSO solution). After the reaction, the primer/DMSO solution is removed, and the beads are treated with concentrated ammonia (e.g., concentration 1-10 mg of beads per ml, for 20 min to 2 hrs at 20 to 35 C). The beads are then washed (e.g., 3 times) with water, (e.g., 2 times) with TET buffer, (e.g., two times) and with TE buffer (e.g., all at concentrations of 1-10 mg of beds per ml). The beads can then be stored in bead storage buffer (e.g., TE Buffer, pH 8.0 containing 0.05% Triton X-100 and 0.01% sodium azide at a concentration of 1 mg of beads per mL). In some cases, the reactions are performed in non-aqueous solvent (e.g., to reduce the amount of the hydrolysis side reaction).

The primer solution can be prepared by dissolving the sodium salt of the primer in tetrabutylammonium solution (e.g., 5 mM, adjusted to pH 7.0, chloride, bromide or acetate counter ions), then dialyzing against the same buffer until the cation exchange is complete. The primer can then be dialyzed against water to remove the excess buffer salts and can be lyophilized to a dry powder. This material can then be dissolved in anhydrous DMSO or NMP and used for primer functionalization. Typical concentrations are about 10% w/v. More or less primer can be used at higher or lower temps for shorter or longer periods of time, altering the amount of primer conjugated.

Figure 13:
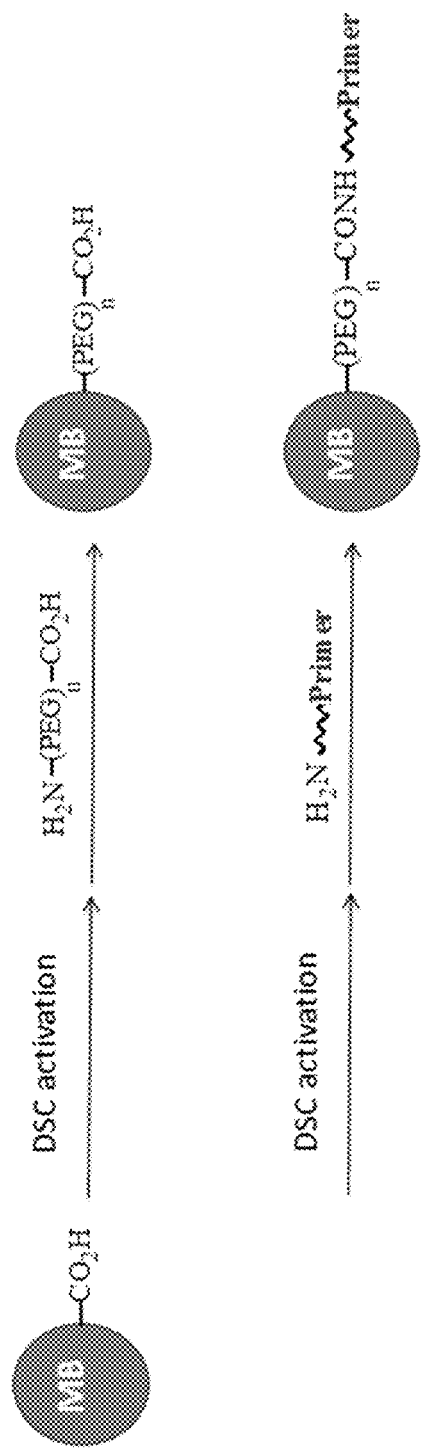
FIG. 13 shows an example of preparation of primer coated beads with PEG linkers.

FIG. 13 shows an example of preparation of primer coated beads with polyethylene glycol (PEG) (e.g., dPEG) linkers. In this example, one or more carboxylic acid groups on beads (e.g., magnetic beads "MB", such as, for example MyOne™ magnetic beads) are activated with N,N-disuccinimidyl carbonate (DSC), converting the one or more carboxylic acid groups into a reactive ester, such as, for example N-hydroxysuccinimide (NHS ester). The reactive ester can react with a heterobifunctional dPEG species that can include terminal amine and carboxylic acid functionalities. In cases where the reactive ester is NHS ester, NHS ester can react with $H_2N-(PEG)_n-CO_2H$ via its terminal amine group resulting in covalent linkage of the PEG species to the bead surface via the formation of an amide bond. The terminal carboxylic acid of the PEG species can then be activated (e.g., via DSC) and its resulting reactive ester (e.g., NHS ester) subsequently reacted with an amino-terminated primer, covalently coupling the primer to the PEG species (and, thus, the bead surface) via an amide bond.

Figure 14:
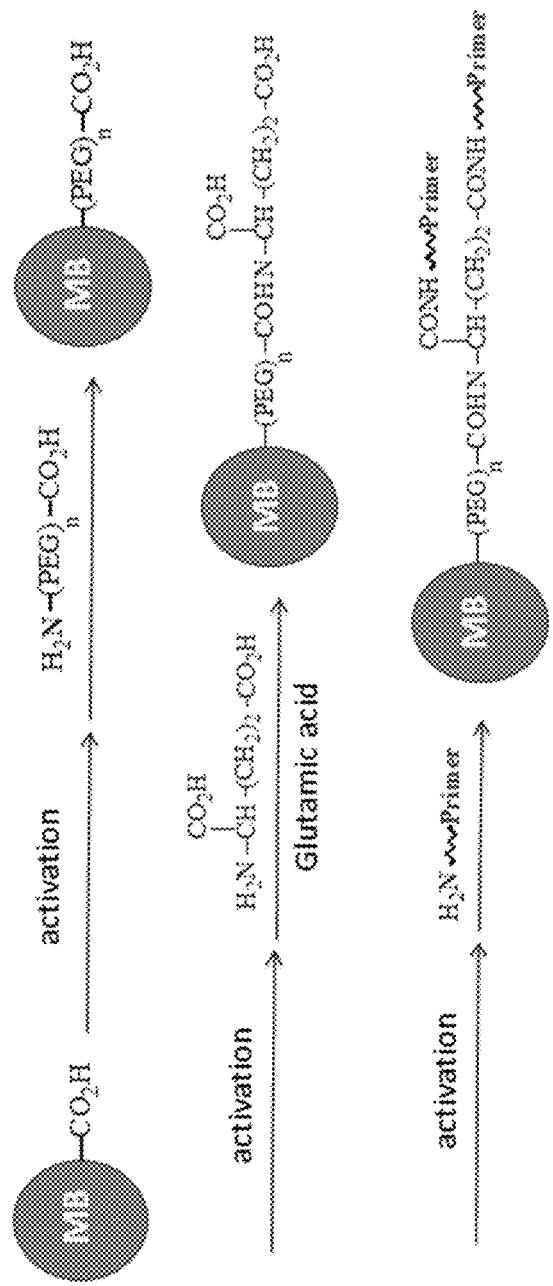
FIG. 14 shows an example of using glutamic acid to increase the active sites for primer loading on primer coated beads with PEG linkers.

FIG. 14 shows another example of preparing primer coated beads similar to that of FIG. 13, where glutamic acid is reacted with DSC activated carboxylic acid groups of a bead-bound PEG species and covalently coupled to the PEG species (and, thus, the bead surface) via an amide bond. The addition of glutamic adds two carboxylic acid groups to the bead surface for every activated PEG carboxylic acid that it reacts with, doubling the number of carboxylic acid groups available for subsequent DSC activation and reaction with an amino-terminated primer. Such a strategy can increase the number of primer molecules bound to the bead.

The loading of beads using a dPEG strategy as described herein can vary depending, for example, the number of dPEG molecules coupled to a bead and the number of functional groups of attached dPEG available for primer attachment. In some cases, the number of primers attached to a PEGylated bead may be at least about 2, at least about 5, at least about 10, at least about 50, at least about 100, at least about 500, at least about 1000, at least about 5000, at least about 10,000, at least about 25,000, at least about 50,000, at least about 60,000, at least about 70,000, at least about 80,000, at least about 90,000, at least about 100,000, at least about 125,000, at least about 150,000, at least about 200,000, at least about 250,000, at least about 300,000, at least about 350,000, at least about 400,000, at least about 450,000, at least about 500,000 at least about 1,000,000 or more.

In some cases, the number of primers attached to a PEGylated bead may be at least about 2, at least about 5, at least about 10, at least about 50, at least about 100, at least about 500, at least about 1000, at least about 5000, at least about 10,000, at least about 25,000, at least about 50,000, at least about 60,000, at least about 70,000, at least about 80,000, at least about 90,000, at least about 100,000, at least about 125,000, at least about 150,000, at least about 200,000, at least about 250,000, at least about 300,000, at least about 350,000, at least about 400,000, at least about 450,000, at least about 500,000 at least about 1,000,000 or more.

In some cases, the number of primers attached to a PEGylated bead may be at most about 1,000,000, at most about 500,000, at most about 450,000, at most about 400,000, at most about 350,000, at most about 300,000, at most about 250,000, at most about 200,000, at most about 150,000, at most about 125,000, at most about 100,000, at most about 90,000, at most about 80,000, at most about 70,000, at most about 60,000, at most about 50,000, at most about 25,000, at most about 10,000, at most about 5,000, at most about 1,000, at most about 500, at most about 100, at most about 50, at most about 10, at most about 5, or less.

While the examples shown in FIGS. 13 and 14 are shown with respect to the attachment of primer molecules to beads, any suitable oligonucleotide comprising amine functionality may be coupled to a bead using the methods and in the numbers described above and shown in FIGS. 13 and 14.

Atom-Transfer Radical Polymerization (ATRP) Beads

Atom-Transfer Radical Polymerization (ATRP) is a controlled method of reversible-deactivation radical polymerization. In ATRP, deactivation of radicals includes reversible atom or group transfer that can be catalyzed by transition-metal complexes (e.g., transition metal complexes of Cu, Fe, Ru, Ni, Os, etc.). An initiator (e.g., aklyl halide, such as an alkyl bromide) can be activated by a transition metal complex to generate a radical species. Monomer can then be reacted with the radical species to attach monomer to the species. The attached monomer can then be activated to form another radical and the process repeated for additional monomers, resulting in the generation of polymerized species.

In some cases, an initiator is activated by a transition metal complex to generate a radical species that subsequently initiates the polymerization of a first monomer added to the initiator. After depletion of the first monomer, a second monomer can be added to continue the polymerization, resulting in a block copolymer. The first monomer that forms a spacer block can be water-soluble and the second monomer can be a reactive monomer that is capable of performing chemical reactions after polymerization. In some cases the first and the second monomers are the same and, in other cases, the first and the second monomers are different. In some cases, the first and the second monomers are added to the initiator at the same time.

Figure 15:
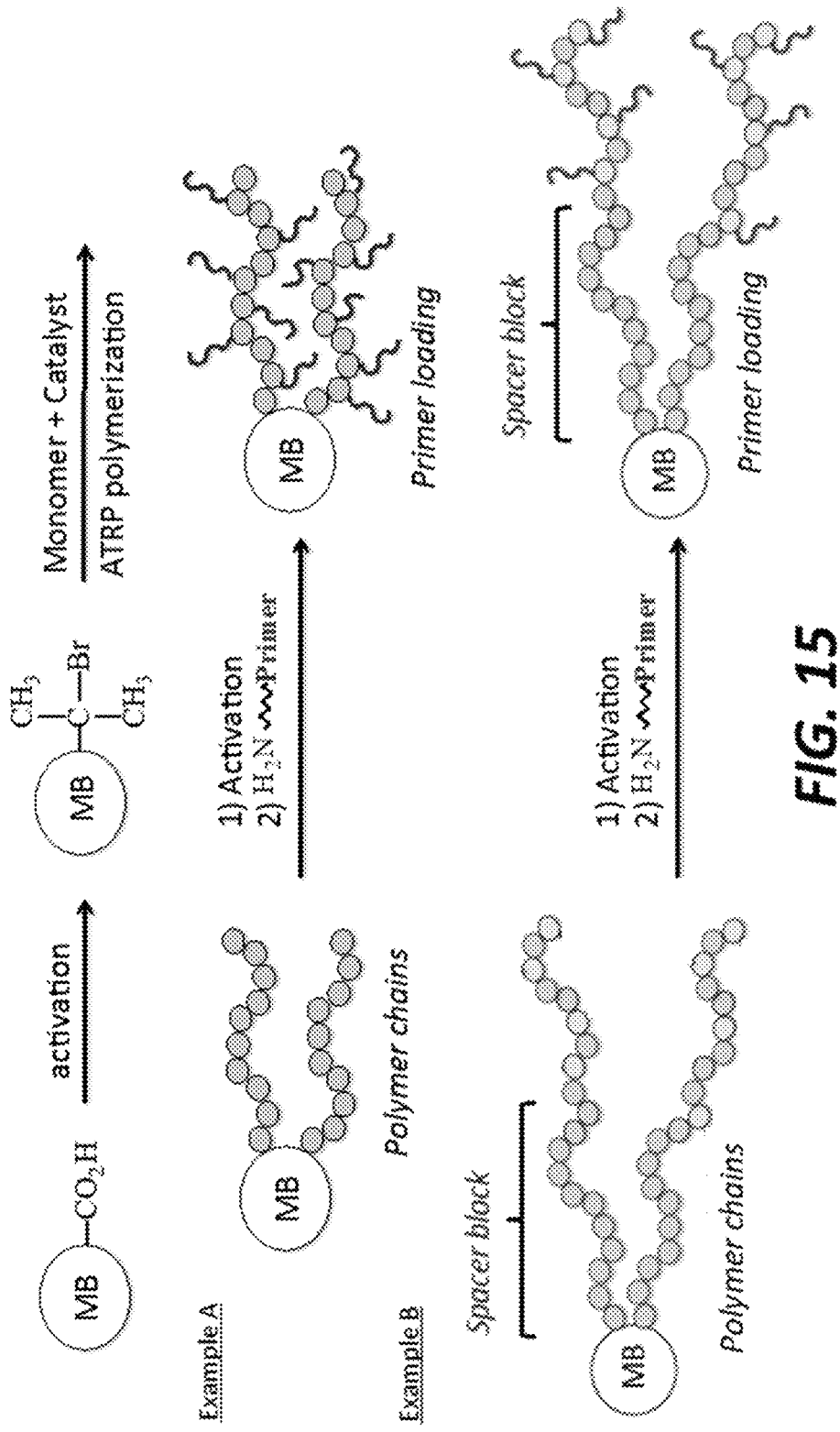
FIG. 15 shows an example of primer-coated magnetic particles created using atom-transfer radical polymerization (ATRP).

In some cases, primer-functionalized particles (e.g., primer-functionalized magnetic beads) can be generated using ATRP. Two examples (Example A and Example B) of an ATRP processes are schematically shown in FIG. 15. In both examples, carboxylic acid bearing beads (e.g., magnetic beads such as, for example MyOne beads) go through an activation process that produces 2-bromoisoproyl groups (—C(CH$_3$)$_2$Br) on the surface of the beads. In some cases, the activation process is a 3-step process that comprises (1) activating the carboxylic acid groups to a reactive ester group (e.g., NHS ester) with DSC, (2) reacting the reactive ester with an excess of 1,3-diaminopropane to introduce primary amine groups on the surface of the beads, and (3) reacting the primary amine groups with α-bromoisobutyryl bromide, resulting in an activated bead comprising an initiator (e.g., 2-bromoisoproyl groups (—C(CH$_3$)$_2$Br) shown in FIG. 15) on its surface that is capable of participating in an Atom Transfer Radical Polymerization (ATRP) reaction.

In both examples shown in FIG. 15, the activated bead is exposed in a solution (e.g., a solution comprising methanol) comprising monomers (e.g., N,N-dimethyl acrylamide (DMA), 2-hydroxyethyl acrylamide (HEAA)), ascorbic acid, a catalyst (e.g., copper bromide), and tris(2-pyridymethylamine (TPMA), resulting in a plurality of polymer chains (e.g., linear polymer chains, poly(DMA-co-HEAA)) grafted onto the surface. Where the polymer chains comprise reactive HEAA monomers, the hydroxyl groups of the HEAA repeat units can be activated with DSC and subsequently reacted with amine-terminated primer (e.g., a primer having at least 2-mers, 5-mers, 10-mers, 15-mers, 20-mers, 25-mers, 30-mers, 35-mers, 40-mers, 45-mers, 50-mers, 55-mers, 60-mers or larger) to give primer-conjugated beads.

In Example A shown in FIG. 15, monomers comprising amine-reactive groups can be randomly added to the growing polymer chains during polymerization resulting in polymer chains that comprise reactive groups randomly distributed throughout the length of the chains. These reactive groups can then be activated (e.g., via DSC) and reacted with amine-bearing primers to couple the primers to the beads, such that primers are coupled to the beads throughout the length of the polymer chains. Examples of this type of strategy are described elsewhere herein and include Example A of FIG. 16, Example V shown in FIG. 17, the example shown in FIG. 18 and the example shown in FIG. 19.

In Example B shown in FIG. 15, first monomers not comprising reactive groups are first added to the beads to form "spacer block" chains that extend out from the surface of the beads. Polymerization proceeds with the addition of second monomers comprising amine-reactive groups to yield larger polymer chains with reactive moieties further down the polymer chains from the spacer block. The reactive groups can then be activated and reacted with amine-bearing primers to couple the primers to the beads. In this strategy, because the amine-reactive groups of the polymer chains are spaced away from the surface of the beads, so too are primers that are coupled to the beads via the polymer chains. Spacing of the reactive groups away from the surface of the beads can reduce steric effects associated with close proximity of conjugated primers to beads and, thus, improve primer loading. Examples of this type of strategy are described elsewhere herein and include Example B of FIG. 16 and one of the examples shown in FIG. 17. The chain lengths of the polymer chains and the degrees of primer conjugation can be controlled by controlling the ratio of the two monomers, the timing for the addition of the second monomer, and the concentration of the amino primer.

While the examples shown in FIG. 15 are with specific reference to amine-terminated primers, amine reactive groups of polymer chains generated via either example of FIG. 15 can be used to couple any suitable type of amine-bearing oligonucleotide to a bead. Polymer chains comprising amine-reactive groups can be generated as described in each example of FIG. 15. The amine reactive groups can then be activated and reacted with amine-bearing oligonucleotides to couple the oligonucleotides to the beads. Amine-bearing peptides, proteins and other species can also be coupled to beads in analogous fashion.

The surface chemistry of high-density primer coatings can be a critical component in the performance of nucleic acid biosensors, and in particular for sensors relying on an enzyme-catalyzed reaction like nucleic acid synthesis. If the primer surface density is too low the resulting signal may fall below the detection limit of the sensor. Therefore, a higher primer surface density can allow more target nucleic acid to be captured resulting in increased detection of nucleic acid synthesis. However too high of a primer density can lead to steric hindrance, electrostatic repulsive forces or primer-primer interactions which can limit the amount of target nucleic acid that can be captured. For a detection system that relies on the amount of captured target nucleic acid it can be important to capture an amount of target nucleic acid that is favorable for the sensor performance and this may not be the highest possible primer density. In an enzyme-catalyzed reaction like nucleic acid synthesis, the generated signal can be determined by the enzyme and its ability to access and incorporate nucleotides to primer-target complexes. In this case, the optimal output signal of the biosensor can depend on a combination of the density of the primer coating, its ability to attract target nucleic acid and the enzymes ability to perform catalytic reaction on primer-target complexes.

The performance of a biosensor with a two-dimensional (2D) surface coating can depend on several factors including the density of the primer coating. A three-dimensional surface (3D) coating on the other hand can allow for either a similar primer density as the 2D surface with increased spacing between primers or a higher primer density altogether, both which may improve the biosensor performance.

In an aspect, described herein is the synthesis of a surface-tethered 3D structure with tailored primer densities. This allows for a higher flexibility of the amount of primers that can be immobilized onto a surface and can be tailored for either target capture (hybridization), amplification of a nucleic acid target sequence and subsequent synthesis of a complementary nucleic acid strand (e.g., as in nucleic acid sequencing). By extending the 2D surface into a 3D volume, more surface area is created for target nucleic acid immobilization. In some embodiments, the increased surface area of the 3D structure is utilized to increase the space between neighboring primers thereby increasing the efficiency for target hybridization and enzymatic nucleic acid amplification. In some cases, the increased surface area of the 3D structure is utilized to increase the amount of nucleic acid that can be immobilized to the footprint area of a biosensor surface, resulting in a stronger biosensor output signals.

The methods described herein use polymer brushes that are extended away from a surface and are accomplished by "grafting-from" procedures like Surface-Initiated Controlled Radical Polymerization (SI-CRP). This allows for precise control of the amount of primers that can be immobilized in a unit volume by enabling three levels of control. The first level of control can be accomplished by tailoring the amount of initiator molecules that are immobilized on the underlying 2D surface. Inert or functional surfaces or mixtures thereof can be constructed and used for conversion into pure or fractional initiator surfaces. Initiator molecules present on these surfaces can be subsequently used in SI-CRP reactions to synthesize polymer brushes that are extending away from the 2D initiator surface. Monomers used for polymerization can include either inert monomers (e.g., N,N-dimethyl acrylamide, inert water-soluble monomers) functional monomers or combinations of inert and functional monomers. The type of monomers used and the ratios in which they are employed can be used as a second level of control where the density of functional groups can be customized. The resulting polymer brushes can be subsequently used for primer immobilization where the functional monomers are activated, followed by primer immobilization. This can provide a third level of control where the density of primers on the polymer brush can be regulated. Primer immobilization can be accomplished by tethering modified functional primers (e.g., amine-modified primers) to the polymer brushes via covalent linkages. In some embodiments, the density of primers on the polymer brush is controlled by the addition of an aminated diluent (e.g., 2-methoxyethylamine). In these cases, active functional monomers can be exposed to a mixture of primers and diluents where the ratio of primers and diluents can be tailored to achieve an appropriate primer density and spacing. In some embodiments, functional co-monomers can be used directly for primer immobilization without the need for activation (e.g. pentafluorophenyl acrylate).

Figure 16:
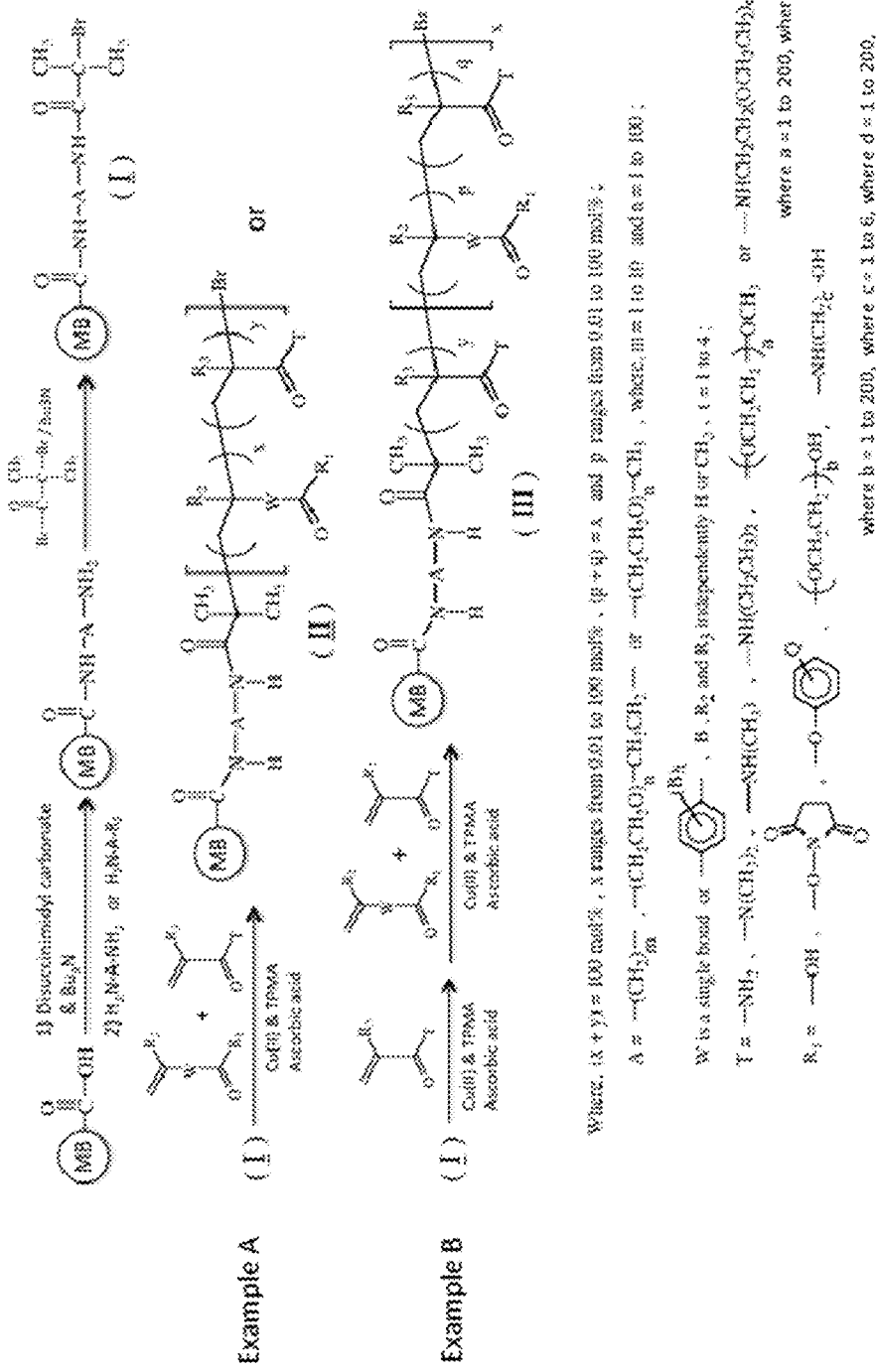
FIG. 16 shows an example preparation of beads comprising ATRP generated polymers.

Additional examples of ATRP-produced beads can be found with reference to FIGS. 16-19. FIG. 16 shows example preparations of ATRP-grafted beads (II and III) starting from a bead (e.g., magnetic bead "MB") bearing carboxylic acid functional groups (e.g., Dynal MyOne carboxylic beads (Life Technologies)). In both examples shown in FIG. 16, the carboxylic acid functional groups are activated with disuccinimidyl carbonate (DSC) in the presence of tributylamine ($Bu_3N$). The activated carboxylic acid groups are then reacted with an amine bearing species (e.g., a diamine species (e.g., $H_2N$-A-$NH_2$) or single amine species (e.g., $H_2N$-A-$NH_2$), where A is —$(CH_2)_m$ (m=1 to 10), —$(CH_2\ CH_2O)_n$—$CH_2CH_2$— (n=1 to 100), —$(CH_2\ CH_2O)_n$—$CH_3$ (n=1 to 100)) to provide a bead bearing amine functional groups. The amine groups are then reacted with a species (e.g., α-bromoisobutyryl bromide ($BrCOC(CH_3)_2Br$) in the presence of $Bu_3N$ to give a radical-activated bead (I) comprising an initiator species comprising a halide (e.g., bromine atom shown in FIG. 16). Other species comprising halides (e.g., 2-chloroisobutryl chloride) can also be used to generate an initiator on the surface of the bead.

In the examples shown in FIG. 16, (I) is reacted with monomeric species to generate polymeric chains on the surface of the bead via ATRP. In one example (Example A) shown in FIG. 16, (I) is reacted with a first monomer (e.g., a monomer comprising "W", "$R_1$" and "$R_2$" groups, with examples for each of W, $R_1$ and $R_2$ shown in FIG. 16) and a second monomer (e.g., a monomer comprising "$R_3$" and "T" groups, with examples for each of $R_3$ and T shown in FIG. 16) in the presence of a catalyst (e.g., copper (II) bromide "Cu(II)", tris(2-pyridylmethyl)amine and ascorbic acid. The resulting bead (II) comprises a random copolymer comprising an "x" mole percent of the first monomer and a "y" mole percent of the second monomer, where (x+y)=100 mol %. The x mole percent, representing the second monomer, can have any suitable value with the remaining percentage attributed to the y mole percent. For example, the x mole percent may be within the range from 0.01 to 100 mol %. In some cases, the x mole percent may be at least 0.01 mol %, at least about 0.1 mol %, at least about 0.5 mol %, at least about 1 mol %, at least about 5 mol %, at least about 10 mol %, at least about 25 mol %, at least about 50 mol %, at least about 75 mol %, at least about 90 mol % or at least about 95 mol %. In some cases, the x mole percent may be at most about 95 mol %, at most about 90 mol %, at most about 75 mol %, at most about 50 mol %, at most about 25 mol %, at most about 10 mol %, at most about 5 mol %, at most about 1 mol %, at most about 0.5 mol %, at most about 0.1 mol %, at most about 0.01 mol %, or less.

In another example (Example B) shown in FIG. 16, (I) is reacted with a first monomer (e.g., a monomer comprising "$R_3$" and "T" groups, with examples for each of $R_3$ and T shown in FIG. 16) in the presence of a catalyst (e.g., copper (II) bromide "Cu(II)", tris(2-pyridylmethyl)amine and ascorbic acid, wherein a homopolymer chain comprising first monomers is generated. The beads are then reacted with a mixture of the first monomer and a second monomer (e.g., a monomer comprising "W", "$R_1$" and "$R_2$" groups, with examples for each of W, $R_1$ and $R_2$ shown in FIG. 16) to copolymer blocks, comprising the first and second monomers, to the homopolymer. The resulting bead (III) comprises a random copolymer comprising a "y" mole percent of the first monomer in the homopolymer segment and a "x" mole percent of the copolymer block comprising the first and second monomer, where (x+y)=100 mol %. In this example, the homopolymer chain can function as a "spacer block" between the surface of the bead and the reactive groups of the monomers that are subsequently added. Such a spacer block can be useful, for example, in minimizing steric effects associated with a relatively close proximity of the polymer chains (and any conjugated oligonucleotides) and improve subsequent oligonucleotide loading.

The x mole percent, can have any suitable value with the remaining percentage attributed to the y mole percent. For example, the x mole percent may be within the range from 0.01 to 100 mol %. In some cases, the x mole percent may be at least 0.01 mol %, at least about 0.1 mol %, at least about 0.5 mol %, at least about 1 mol %, at least about 5 mol %, at least about 10 mol %, at least about 25 mol %, at least about 50 mol %, at least about 75 mol %, at least about 90 mol % at least about 95 mol % or more. In some cases, the x mole percent may be at most about 95 mol %, at most about 90 mol %, at most about 75 mol %, at most about 50 mol %, at most about 25 mol %, at most about 10 mol %, at most about 5 mol %, at most about 1 mol %, at most about 0.5 mol %, at most about 0.1 mol %, at most about 0.01 mol %, or less. Moreover, in this example, the x mole percent is the sum of the mole percent ("q") of the first monomer and the mole percent ("p") of the second monomer making up the copolymer block (e.g., x=(p+q)). For example, the p mole percent may be within the range from 0.01 to 100 mol %. In some cases, the p mole percent may be at least 0.01 mol %, at least about 0.1 mol %, at least about 0.5 mol %, at least about 1 mol %, at least about 5 mol %, at least about 10 mol %, at least about 25 mol %, at least about 50 mol %, at least about 75 mol %, at least about 90 mol %, at least about 95 mol % or more. In some cases, the p mole percent may be at most about 95 mol %, at most about 90 mol %, at most about 75 mol %, at most about 50 mol %, at most about 25 mol %, at most about 10 mol %, at most about 5 mol %, at most about 1 mol %, at most about 0.5 mol %, at most about 0.1 mol %, at most about 0.01 mol %, or less.

In the examples shown in FIG. 16, the $R_1$ groups of the grafted polymers of (II) and (III) are amine-reactive and can be subsequently reacted with amine-bearing primers or other amine-bearing oligonucleotides to couple the primers or oligonucleotides to (II) and (III). As described elsewhere herein, the ratio of loading can be controlled, for example, by the number of primer or oligonucleotide molecules reacted with the $R_1$ groups and/or by the availability of $R_1$ groups for reaction. The availability of $R_1$ groups can be controlled by the number of monomer molecules comprising $R_1$ groups that are added during polymerization. In some cases, varied amounts of monomer and/or other components can result in varied numbers of $R_1$ groups that are added during polymerization.

Figure 17:
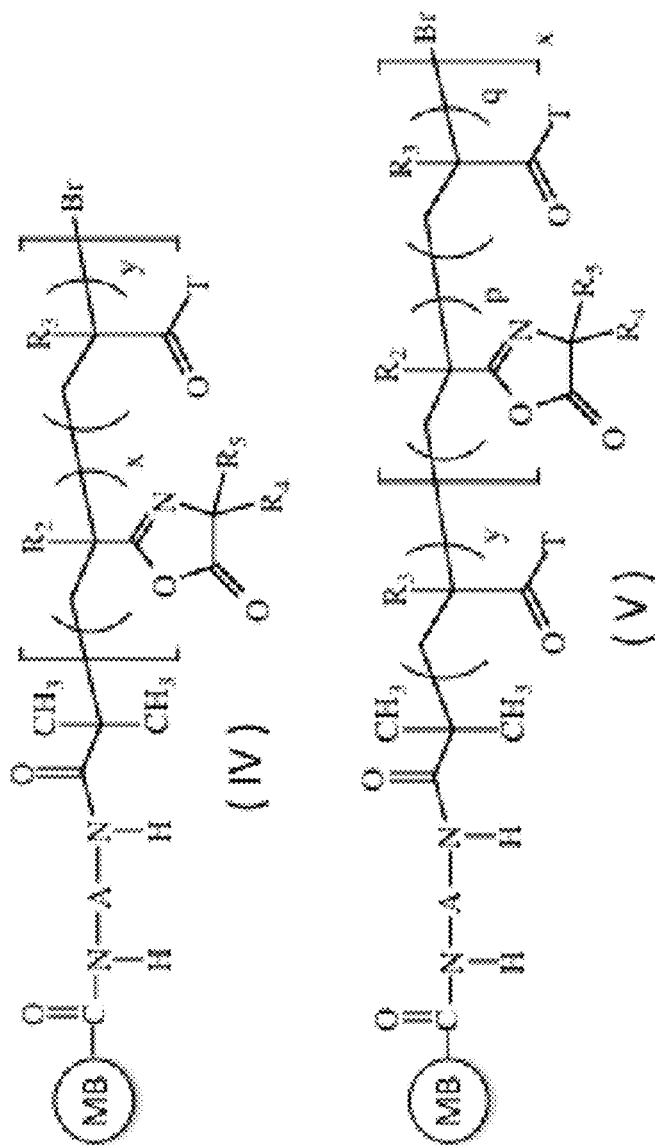
FIG. 17 shows an example of beads comprising ATRP generated polymers.

FIG. 17 shows additional examples of ATRP-grafted beads (e.g., magnetic beads "MB")) (IV and V) comprising vinyl azlactone reactive groups that can react with amine-bearing primers, other amine-bearing oligonucleotides or other amine-bearing biomolecules. (IV) can be prepared from (I) shown in FIG. 16 via the method shown in Example A as described above, except that the first monomer comprises an amine-reactive vinyl azlactone group that comprises $R_4$ and $R_5$ groups (e.g., the vinyl azlactone containing monomer in FIG. 9C). Moreover, (V) can be prepared from (I) shown in FIG. 16 via the method shown in Example B as described above, where the second monomer comprises an amine-reactive vinyl azlactone group that comprises $R_4$ and $R_5$ groups e.g., the vinyl azlactone containing monomer in FIG. 9C). In both (IV) and (V), the $R_4$ and $R_5$ groups can be independently H or $CH_3$. The mole percentages described with respect to Example A and Example B in FIG. 16 are also applicable to (IV) and (V), respectively, shown in FIG. 17.

Figure 18:
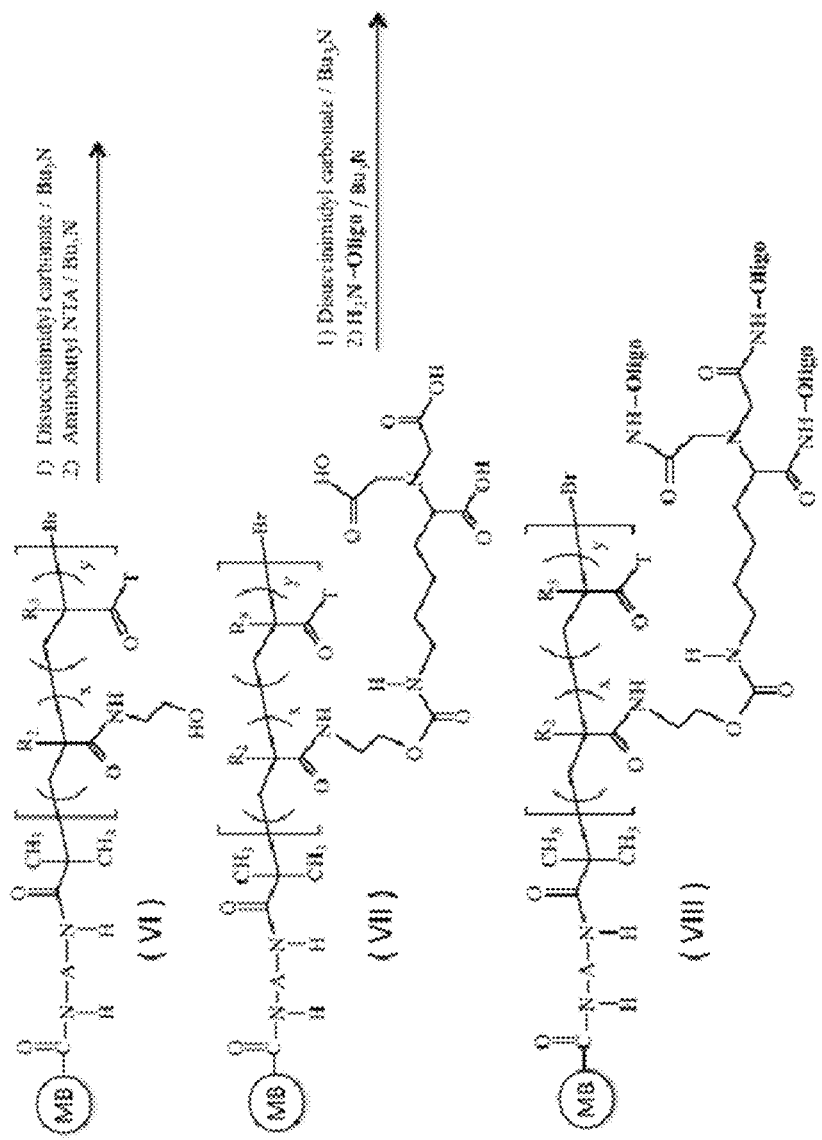
FIG. 18 shows an example preparation of beads comprising ATRP generated polymers attached to oligonucleotides.

FIG. 18 shows an example of hyper-branched ATRP-grafted beads (e.g., magnetic beads "MB") (VI) comprising 2-hydroxyethyl acrylamide reactive groups that can react with additional species to provide more than one amine-reactive group per monomer. (VI) can be prepared from (I) shown in FIG. 16 via the method shown in Example A as described above, where the W group of the first monomer is a single bond and the $R_1$ group is a 2-hydroxyethyl acrylamide group that comprises a terminal hydroxyl group. The x and y mole percentages described with respect to Example A in FIG. 16 are also applicable to (VI) (and, thus, (VII) and (VIII) described below) shown in FIG. 18.

The terminal hydroxyl groups of (VI) can be activated with DSC in the presence of $Bu_3N$ and the activated species then reacted with N-(5-Amino-1-carboxypentyl)iminodiacetic acid (Aminobutyl NTA in FIG. 18) in the presence of $Bu_3N$ to yield (VII) shown in FIG. 18. As shown in FIG. 18, (VII) comprises a plurality of carboxylic acid groups (e.g., three shown in FIG. 18) for every monomer unit originally comprising a single 2-hydroxyethyl acrylamide reactive group. The carboxylic acid groups can then be subject to another round of DSC activation in the presence of $Bu_3N$, followed by reaction of the activated carboxylic acid groups with amine-bearing primers, other amine-bearing oligonucleotides (e.g., "oligo") or other amine-bearing biomolecules (e.g., amine-bearing proteins, amine-bearing peptides and amine-containing carbohydrates) that yields (VIII)— beads coupled to primer or other type of oligonucleotide.

Figure 19:
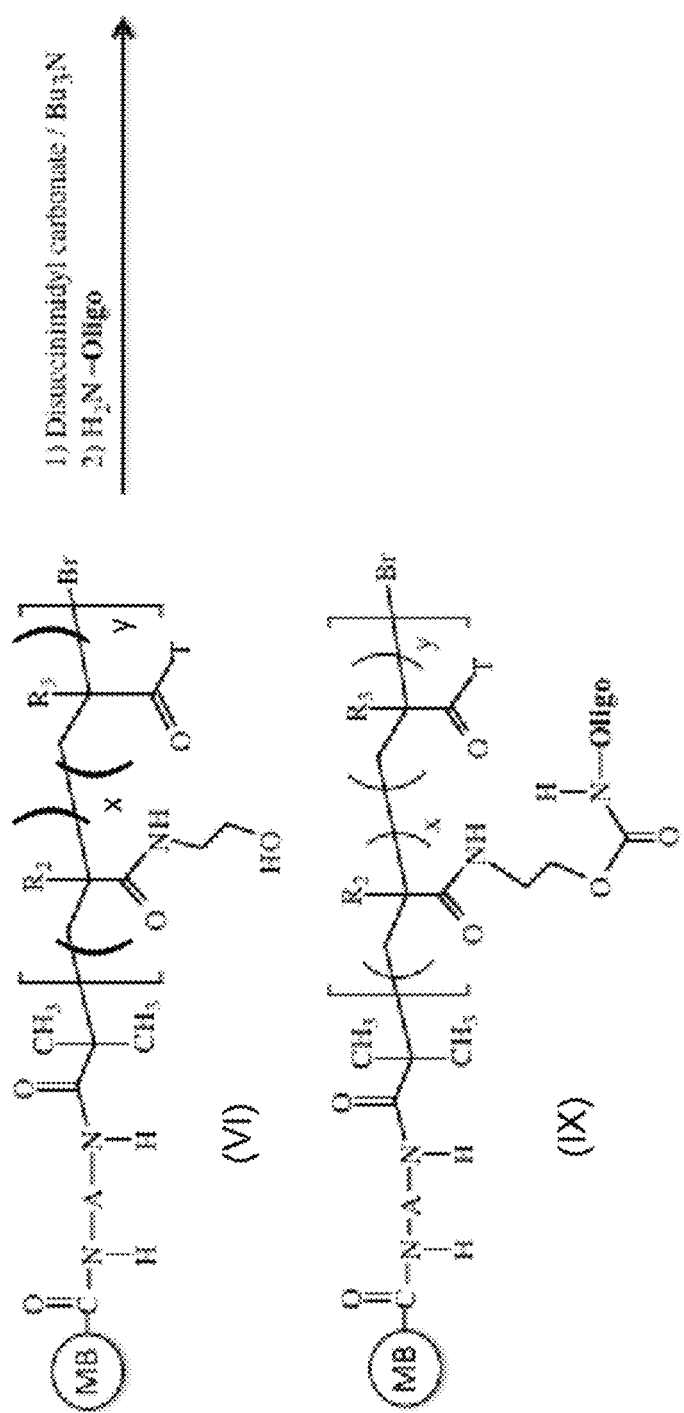
FIG. 19 shows an example preparation of beads comprising ATRP generated polymers attached to oligonucleotides.

FIG. 19 shows an example of attaching primers or other types of oligonucleotides to the ATRP-grafted beads (VI) described above and shown in FIG. 18, without first adding N-(5-Amino-1-carboxypentyl)iminodiacetic acid to (VI). As shown in FIG. 19, the terminal hydroxyl group of the 2-hydroxyethyl acrylamide groups of (VI) can be activated with DSC in the presence of $Bu_3N$. The activated hydroxyl groups can then react with an amine-bearing primer, other type of amine-bearing oligonucleotide or other amine-bearing biomolecule (e.g., amine-bearing proteins, amine-bearing peptides, amine-containing carbohydrates) to generate (IX)-beads coupled to primer or other type of oligonucleotide. As is discussed above, the x and y mole percentages described with respect to Example A in FIG. 16 are also applicable to (VI) and, thus, (IX) also.

While not shown in the examples of FIG. 18 and FIG. 19, a bead having polymer chains may be generated according to Example B shown in FIG. 16, where the $R_1$ group on the second monomers is 2-hydroxyethyl acrylamide. This can then react with N-(5-Amino-1-carboxypentyl)iminodiacetic acid in the presence of $Bu_3N$ to provide a plurality of carboxylic acid functional groups for every $R_1$ reactive group, analogous to VII shown in FIG. 18. The carboxylic acid functional groups can then be activated DSC in the presence of $Bu_3N$ and subsequently reacted with amine-bearing primers, other amine-bearing oligonucleotides or other amine-bearing biomolecules (e.g., amine-bearing proteins, amine-bearing peptides, amine-bearing carbohydrates) to couple the relevant amine-bearing species to the beads. Alternatively and analogous to the example shown in FIG. 19, the $R_1$ group on the second monomers may be activated with DSC in the presence of $Bu_3N$ and then reacted with amine-bearing primers, amine-bearing oligonucleotides or other amine-bearing biomolecule (e.g., amine-bearing proteins, amine-bearing carbohydrates, amine-bearing peptides) to couple the relevant species to the beads.

The primer or other oligonucleotide loading of beads using an ATRP strategy as described herein can vary depending, for example, the number of polymer molecules generated on a bead and/or the number of polymer reactive groups available of for reaction. In some cases, the number of primers or other oligonucleotides attached to a bead comprising an ATRP generated polymer may be at least about 2, at least about 5, at least about 10, at least about 50, at least about 100, at least about 500, at least about 1000, at least about 5000, at least about 10,000, at least about 25,000, at least about 50,000, at least about 60,000, at least about 70,000, at least about 80,000, at least about 90,000, at least about 100,000, at least about 125,000, at least about 150,000, at least about 200,000, at least about 250,000, at least about 300,000, at least about 350,000, at least about 400,000, at least about 450,000, at least about 500,000 at least about 1,000,000 or more.

In some cases, the number of primers or other oligonucleotides attached to a bead comprising an ATRP generated polymer may be at most about 1,000,000, at most about 500,000, at most about 450,000, at most about 400,000, at most about 350,000, at most about 300,000, at most about 250,000, at most about 200,000, at most about 150,000, at most about 125,000, at most about 100,000, at most about 90,000, at most about 80,000, at most about 70,000, at most about 60,000, at most about 50,000, at most about 25,000, at most about 10,000, at most about 5,000, at most about 1,000, at most about 500, at most about 100, at most about 50, at most about 10, at most about 5, or less.

In some cases, the molecular weight of polymer chains on a bead, including those beads shown in the examples of FIGS. 16-19 can range from 10 kiloDalton (KDa) to 3000 KDa, 50 KDa to 2500 KDa, 100 KDa to 1,500 KDa, or 500 KDa to 1,000 KDa. In some embodiments, the molecular weight of the grafting polymer can be about 10 KDa, 25 KDa, 50 KDa, 100 KDa, 150 KDa, 200 KDa, 250 KDa, 300 KDa, 350 KDa, 400 KDa, 450 KDa, 500 KDa, 550 KDa, 600 KDa, 650 KDa, 700 KDa, 750 KDa, 800 KDa, 850 KDa, 900 KDa, 950 KDa, 1000 KDa, 1050 KDa, 1100 KDa, 1150 KDa, 1200 KDa, 1250 KDa, 1300 KDa, 1350 KDa, 1400 KDa, 1450 KDa, 1500 KDa, 1550 KDa, 1600 KDa, 1650 KDa, 1700 KDa, 1750 KDa, 1800 KDa, 1850 KDa, 1900 KDa, 1950 KDa, 2000 KDa, 2050 KDa, 2100 KDa, 2150 KDa, 2200 KDa, 2250 KDa, 2300 KDa, 2350 KDa, 2400 KDa, 2450 KDa, 2500 KDa, 2550 KDa, 2600 KDa, 2650 KDa, 2700 KDa, 2750 KDa, 2800 KDa, 2850 KDa, 2900 KDa, 2950 KDa or 3000 KDa.

EXAMPLES

Example 1: Preparation of Tetrabutylammonium Salt of 15-Mers

A tetrabutylammonium salt of a 15-mer primer can be relatively soluble in non-aqueous solvents (e.g., N-methyl pyrrolidone (NMP), DMSO), in which a surface-grafted reactive polymer on a bead is swollen. Such solubility can result in enhanced conjugation of the 15-mer primer to the reactive polymer. This example describes the conversion a water-soluble sodium salt of a 15-mer oligo into one that is soluble in a non-aqueous solvent, such as NMP.

Prior to conversion, general handling guidelines of the 15-mer oligo can include warming up the oligo to ambient temperature prior to opening a container having the 15-mer oligo and handling the oligo in clean and dust-free environments to avoid cross contamination. Anhydrous amine-free NMP can be prepared by passing NMP through a neutral alumina column followed by storage under molecular sieves.

Instruments and materials useful in the preparation can include the following shown in Table 1:

TABLE 1

| Instruments & Materials | Supplier | Cat # CAS# |
|---|---|---|
| Dialysis cassettes: Slide-A-Lyzer®, MWCO 2000 | Thermo Scientific | 66212 N/A |
| Tetrabutylammonium chloride (TBAC) | Sigma Aldrich | 86852 1112-67-0 |
| Tetrabutylammonium hydroxide, 40% solution | Sigma Aldrich | 86854 2052-49-5 |
| Oligo TIB 15-mer, sodium salt, (MW 4674.1) 5'-AminoC6-dC-dC-T-dA-T-dC-dC-dC-dC-T-dG-T-dG-T-dG-3' | Oligo Factory | N/A N/A |
| Falcon tube, polypropylene, 15-mL | VWR | 21008-936 N/A |

An example protocol that was completed for the preparation of tetrabutylammonium salt of primer (15-mer) included:

(a) A dialysis cassette (e.g., Slide-A-Lyzer®, Thermo Scientific) was filled with 18MΩ water and re-hydrated in 100 mL of 18MΩ water for 2 hours;

(b) A 5 mM TBAC buffer was prepared by dissolving 1.390 g of tetrabutylammonium chloride in 1 L of 18 MΩ water and adjusting the pH to 7 by adding 40% tetrabutylammonium hydroxide (about 200 μL);

(c) In a 15 mL Falcon tube, 211.0 mg of a sodium salt primer (obtained from Oligo Factory, TIB 15-mer, MW 4674.1, 5'-aminoC6-dC-dC-T-dA-T-dC-dC-dC-dC-T-dG-T-dG-T-dG-3') was dissolved into 8 mL of the TBAC buffer;

(d) The primer solution was transferred into the dialysis cassette with syringe needles;

(e) The 15 mL tube was rinsed twice with 1 mL of the TBAC buffer and the rinses transferred into the dialysis cassette;

(f) Air bubbles inside the dialysis cassette were removed with a syringe needle;

(g) The primer solution was dialyzed in 1 L of the TBAC buffer with changes of fresh TBAC buffer 2 times per day for 2 days;

(h) Step (g) was repeated with 18 MΩ water;

(i) The dialyzed solution was distributed into sixteen 2-mL micro centrifuge tubes;

(j) The contents of the tubes were frozen at −20° C.;

(k) The contents were evaporated to dryness and constant weight in a Spin-Vap evaporator or a lyophilizer.

The dried primer was dissolved in anhydrous amine-free NMP in 1:10 or 1:5 w/v ratio prior to use.

Example 2: Preparation of Amino Beads

As described elsewhere herein, amino-bearing magnetic beads can be used for surface grafting a pre-fabricated reactive polymer or copolymer for subsequent conjugation of oligos. This example provides a protocol for generating amino-bearing magnetic beads. In this example, MyOne™ carboxylic-bearing beads (Thermo Scientific) are converted into amino beads using disuccinimidyl carbonate (DSC) and diaminopropane (e.g., 1, 3-diaminopropane). The example protocol described in this example can also be applicable to conversion of carboxylic-bearing beads (e.g., ProMag-HC from Bangs) to amino-bearing beads.

General material handling guidelines can include: handling disuccinimidyl carbonate under dry conditions as it can be hydroscopic and hydrolytically unstable and handling 1,3-diaminopropane in a fume hood as it is volatile when exposed to air. Anhydrous amine-free NMP can be prepared by passing NMP through a neutral alumina column followed by storage under molecular sieves.

Instruments and materials useful in the preparation can include the following shown in Table 2:

TABLE 2

| Instruments & Materials | Supplier | Cat # CAS# |
|---|---|---|
| MyOne™ Carboxylic beads 1μ size, 10 mg/mL, 10 B/mL | Thermo Scientific Life Technologies | 2016-10 N/A |
| N,N'-Disuccinimidyl carbonate (DSC) | Sigma Aldrich | 225827 74124-79-1 |
| Tributylamine | Sigma Aldrich | 90781 102-82-9 |
| 1,3-diaminopropane | Sigma Aldrich | D23602 109-76-2 |
| N-methyl pyrrolidone (NMP) | Sigma Aldrich | 328634 872-50-4 |
| Acetonitrile (AcN) | Sigma Aldrich | 271004 75-05-8 |
| Falcon tube, polypropylene, 15-mL | VWR | 21008-936 N/A |

An example protocol that was completed for the preparation of amino-bearing magnetic beads using DSC in anhydrous amine-free NMP as a solvent included:

(a) To a 15-mL Falcon tube, 2 mL of re-suspended MyOne™ carboxylic acid beads were added;

(b) The beads were washed with 5 mL of anhydrous amine-free NMP 4 times;

(c) A solution of 0.2620 g (1.0228 millimoles (mmol)) of DSC and 0.20 mL (0.8395 mmol) of tributylamine in 8 mL of anhydrous amine-free NMP was added and the resulting mixture tumbled for 18 hours at ambient temperature;

(d) The beads were washed 4 times with 5 mL of anhydrous amine-free NMP;

(e) The beads were re-suspended in 5 mL of anhydrous amine-free NMP and 1.50 mL (17.971 mmol) of 1,3-diamiopropane added;

(f) The resulting mixture was tumbled for 24 hours at ambient temperature;

(g) The beads were washed 4 times with 5 mL of anhydrous amine-free NMP; and (h) The beads were re-suspended in 5 mL of anhydrous amine-free NMP and stored in a refrigerator at 4° C.

An example protocol completed for the preparation of amino-bearing magnetic beads using DSC in acetonitrile (AcN) as a solvent included:

(a) To a 15-mL centrifugation tube, 2 mL of re-suspended MyOne™ carboxylic acid beads were added;

(b) Beads with 5 mL of anhydrous AcN 4 times were added;

(c) A solution of 0.2601 g (1.0153 mmol) of DSC and 0.20 mL (0.8395 mmol) of tributylamine in 8 mL of anhydrous AcN was added and the resulting mixture tumbled for 18 hours at ambient temperature;

(d) The beads were washed 4 times with 6 mL of anhydrous AcN;

(e) The beads were re-suspended in 10 mL of anhydrous AcN, and 1.50 mL (17.971 mmol) of 1,3-diamiopropane added, followed by tumbling for 23 hours at ambient temperature; and (f) The beads were washed 4 times with 5 mL of anhydrous AcN, re-suspended in 5 mL of anhydrous AcN, and stored in a refrigerator at 4° C.

Example 3: Preparation of 20% Active Grafting Polymer

As described elsewhere herein, a grafting polymer can work as a linkage that covalently attaches a primer onto the surface of a bead (e.g., magnetic bead). Copolymer prepared by polymerizing pentafluorophenyl acetate (PFPA), a reactive ester, with N,N-dimethyl acrylamide (DMA), a water-soluble monomer, in 20 to 80 molar ratio can space apart primers on the surfaces of a bead (e.g., magnetic bead) and can, thus, result in increased amplicon to primer ratio after amplification. This co-polymer (e.g., having 20 mol % reactive groups) is soluble in non-aqueous solvents such as N-methyl pyrrolidone (NMP) and acetonitrile (AcN). Such a co-polymer can be relatively hydrophilic and hygroscopic and, in such cases, should be stored at low temperature (e.g., at −20° C.) in a sealed container, and warmed to ambient temperature prior to use.

General handling guidelines for materials include: (a) purifying PFPA and DMA monomers by vacuum fractional distillation to remove inhibitors and other impurities, and store the purified monomers in a container and at −20° C.; (b) warming up the purified monomers to ambient temperature prior to opening the container; (c) handling the monomers and carrying out the polymerization in a ventilation hood; and (d) leaving protective gloves in the ventilation hood after handling monomers or any items contaminated with monomers. These contaminated items can be disposed as hazardous waste.

Instruments and materials useful in the preparation can include the following shown in Table 3:

TABLE 3

| Instruments & Materials | Company | Cat # | CAS# |
|---|---|---|---|
| Pentafluorophenyl acrylate (PFPA) | Monomer-Polymer & Dajac Labs | 9133 | N/A |
| N,N-Dimethyl acrylamide (DMA) | Sigma Aldrich | 274316 | 268-03-7 |
| Acetonitrile (AcN), anhydrous | Sigma Aldrich | 271004 | 75-05-8 |
| 2,2'-Azobis(2,4-dimethylvaleronitrile) (Vazo-52) | TCI | A0680 | 4419-11-8 |
| Tetrahydrofurane (THF), anhydrous | Sigma Aldrich | 401757 | 109-99-9 |
| Hexane | Sigma Aldrich | 270504 | 110-54-3 |
| Mineral oil | Sigma Aldrich | M3516 | 8042-47-5 |
| Recrystallization dish | ChemGlass | CG-8276-150 | N/A |
| Three-necked round bottom flask, 500 mL | ChemGlass | CG-1522-05 | N/A |
| Mechanical stir, digital | ChemGlass | CG-2079-01 | N/A |
| 2" TEFLON stirring blade | ChemGlass | CG-2080-02 | N/A |

TABLE 3-continued

| Instruments & Materials | Company | Cat # | CAS# |
|---|---|---|---|
| Stirring shaft | ChemGlass | CG-2079-01 | N/A |
| Adapter, 24/40 male to 14/20 female | ChemGlass | CG-1000-43 | N/A |
| Rubber Septum, 14/20 | ChemGlass | CG-3022-93 | N/A |
| Rubber septum, 24/40 | ChemGlass | CG-3022-98 | N/A |
| SS syringe needle, 20 gauge, 2" | VWR | 89078-054 | N/A |
| SS syringe needles, 18 gauge, 2" | VWR | 89078-056 | N/A |
| SS syringe needles, 18 gauge 12" | ChemGlass | CG-3075-41 | N/A |
| Erlenmeyer flask, 2 L | ChemGlass | CG-8510-2L | N/A |
| Cooling circulation bath | Scinics | CH-JR | N/A |
| Heater and stirrer | ChemGlass | CG-1994 | N/A |
| Mechanical stir | SCILOGEX | OS20-S LED | N/A |
| Flow meter | Col-Parmer | 03217-06 | N/A |
| Bubbler | ChemGlass | AF-0513-20 | N/A |

An example protocol completed for co-polymerization of PFPA and DMA included:

(a) A reaction vessel comprising a three-necked 500-mL round bottom flask equipped with a 2" TEFLON stir blade, a 24/40 to 14/20 ground glass adapter, a 14/20 water-cool condenser, rubber septum for 14/20 and 24/40 joints, one 12" 18-gauge SS syringe needle for nitrogen purging, and one 2" 18-gauge SS syringe needle for venting into a mineral oil bubbler was provided;

(b) The 500-mL three-necked round bottom flask was charged with 30 mL of anhydrous AcN, 8.004 g (80.741 mmol) of DMA (Sigma Aldrich, vacuum distilled), 4.801 g (20.163 mmol) of PFPA (Monomer-Polymer Dajac Labs, vacuum distilled), and 0.011 g (0.044 mmol) of 2,2'-azobis (2,4-dimethylvaleronitrile) (Vazo-52, TCI America);

(c) The reaction mixture was purged at ambient temperature by gentle bubbling of ultrapure nitrogen at ~60 mL/min for 30 minutes with constant stirring at 125 rpm;

(d) The reaction flask was immersed into an oil bath at 55° C. for 19 hours with ultrapure nitrogen bubbling at a flow rate of 25 mL/min and constant stirring at 120 rpm, the resulting reaction mixture was highly viscous;

(e) The solvent was removed under reduced pressure (Rota-Vap) at 60° C. water bath temperature for 60 minutes to give a solid mass of polymer;

(f) The polymer product was re-dissolved in 30 mL of anhydrous THF;

(g) 20 mL of n-hexane was added dropwise under constant stirring. The resulting solution was cloudy;

(h) To 800-mL of n-hexane in a 2-L glass Erlenmeyer flask, continuously flooded with dry nitrogen, the polymer in THF/hexane was added in a fine stream while stirring vigorously using a 2" TEFLON stirring blade;

(i) The precipitated polymer was stirred for an additional 5 minutes and discarding the supernatant;

(j) To the precipitated polymer, 500 mL of fresh n-hexane was added and stirred gently for 10 minutes;

(k) (i-j) were repeated once to generate a re-precipitated polymer; and (l). The precipitated polymer was transferred into a large mouth 500-mL glass bottle, and dried under vacuum at 60° C. for 24 hours to give 9.2 g of poly(PFPA-co-DMA).

Example 4: Grafting of 20%-Active Polymer and Conjugation of 15-Mers

A reactive grafting polymer (e.g., a 20%-reactive grafting polymer as prepared by methods described in Example 3) can be grafted to a bead and primers can be coupled to the grafted polymer. This example describes example methods for both polymer grafting and primer coupling to grafted polymer. A reactive grafting polymer can be hydroscopic and, in such cases, should be handled accordingly.

General handling guidelines for materials can include: (a) preparing a fresh capping solution for use on the same day; (b) using a new 100-mL bottle of anhydrous acetonitrile, AcN, for each reaction; (c) preparing anhydrous amine-free NMP by passing NMP through a neutral alumina column and storing it under molecular sieves.

Instruments and materials useful in the preparations can include the following shown in Table 4:

TABLE 4

| Instruments & Materials | Supplier | Cat # CAS# |
|---|---|---|
| N-methyl pyrrolidone (NMP) | Sigma Aldrich | 328634 872-50-4 |
| Acetonitrile (AcN) | Sigma Aldrich | 271004 75-05-8 |
| Triethylamine | Sigma Aldrich | T0886 121-44-8 |
| Ammonium hydroxide, 28% | Sigma Aldrich | 320145 1336-21-6 |
| Triton X-100 | Sigma Aldrich | 234729 9002-93-1 |
| Sodium azide | Sigma Aldrich | S8032 26628-22-8 |
| 1× TE buffer | Ambion | AM9858 N/A |
| Aminated magnetic beads prepared with DCS in NMP | N/A | N/A N/A |
| Aminated magnetic bead prepared with DSC in AcN | N/A | N/A N/A |
| 20%-Active grafting polymer | N/A | N/A N/A |
| Tetrabutylammonium salt of 15-Mer | N/A | N/A N/A |
| Orbital shaker (Thermomixer R) | Eppendorf | N/A N/A |
| 50-mL Falcon tube, polypropylene | VWR | 21008-940 N/A |

An example protocol that was completed for preparation of capping solution included:

(a) A 1.0 M ammonium hydroxide solution was prepared by adding 1.21 mL of 28% ammonium hydroxide into 10 mL of DI water, and then diluting it to 20 mL with DI water;

(b) The capping solution was prepared by adding 4 mL of 1.0 M ammonium hydroxide solution and 0.554 mL of trimethylamine (TEA) into 10 mL of DI water, and then diluting it with DI water to 40 mL;

An example protocol that was completed for grafting of aminated magnetic beads and conjugating a 15 mer primer in NMP included:

(a) An aliquot of 12 billion aminated beads in suspension, prepared with DSC in NMP as a solvent, was washed with 20 mL of anhydrous amino-free NMP 2 times in a 50-mL Falcon tube, and the beads re-suspended and sonicated in 5 mL of anhydrous amine-free NMP;

(b) 600.8 mg of 20%-reactive grafting polymer was dissolved in 12 mL of NMP;

(c) 24 µL of TEA was added into the polymer solution;

(d) The bead suspension was added into the polymer solution and tumbled for 20 hours at ambient temperature;

(e) The beads were washed 3 times with 10 mL of anhydrous amine-free NMP;

(f) The beads were re-suspended in 0.6 mL of anhydrous amine-free NMP, 600 µL of a solution containing 20% w/v 15-mer primer in anhydrous amine-free NMP added, and the mixture tumbled for 20 hours at ambient temperature;

(g) The beads were washed 3 times with 10 mL NMP, 1× with 10 mL of 50% aqueous NMP, and 1× with 10 mL of 18 MΩ water;

(h) 15 mL of capping solution was added containing 100 mM TEA and 100 mM ammonia, and shaken in an Thermomixer for 2 hours at 60° C.;

(i) The beads were washed 3 times with 10 mL of 18 MΩ water. Additional washing can be completed if the pH is higher than 7;

(j) To the beads, 12 mL of 1× TE buffer pH 8.0 containing 0.05% Triton-100 and 0.01% of sodium azide (pH 7) was added and the suspension was stored in a refrigerator at 4° C.;

An example protocol that was completed for grafting of aminated magnetic beads in AcN and conjugating 15 mer primer in NMP included:

(a) An aliquot of 12 billion aminated beads in suspension, prepared with DSC in AcN as a solvent, was washed with 20 mL of anhydrous AcN 2 times in a 50-mL Falcon tube, re-suspended and sonicated in 5 mL of anhydrous AcN;

(b) 612.4 mg of the 20%-reactive grafting polymer was dissolved in 12 mL of anhydrous AcN;

(c) 24 µL of TEA was added into the polymer solution;

(d) The bead suspension was added into the polymer solution and tumbled for 20 hours at ambient temperature;

(e) The beads were washed 3 times with 10 L of anhydrous AcN and 1× with 10 mL of 1:1 v/v anhydrous AcN, and 2× with 10 mL of anhydrous amine-free NMP;

(f) The beads were re-suspended in 0.6 mL of anhydrous amine-free NMP, 300 µL of a solution containing 20% w/v 15-mer primer in anhydrous amine-free NMP was added, and the mixture tumbled for 20 hours at ambient temperature;

(g) The beads were washed 3 times with 10 mL NMP, 1× with 10 mL of 50% aqueous NMP, and 1× with 10 mL of 18 MΩ water;

(h) 15 mL of capping solution containing 100 mM TEA and 100 mM ammonia was added and the mixture shaken in a Thermomixer for 2 hours at 60° C.;

(i) The beads were washed 3 times with 10 mL of 18 MΩ water. Additional washing can be completed if the pH is higher than 7; and (j) To the beads, 12 mL of 1× TE buffer containing 0.05% Triton-100 and 0.04% of sodium azide (pH 7) was added and the suspension is stored in a refrigerator at 4° C.

Example 5: Synthesis of PEGylated Beads Comprising Oligonucleotides

Figure 20A:
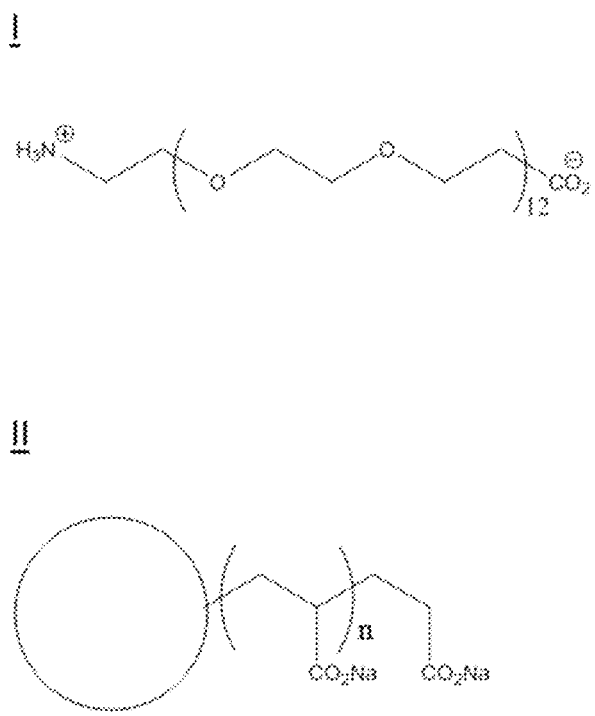
FIGS. 20A-20C schematically depict an example preparation of PEGylated oligonucleotide-bearing beads.

In this example, beads comprising dPEG chains linked to oligonucleotides are generated. As shown in FIG. 20A (panel I), a heterobifunctional dPEG comprising repeating ethylene glycol units and amine and carboxylic acid functional groups (e.g., amino-dPEG-12-acid) is provided. The size of the example dPEG shown in FIG. 20A (panel I) is 24, referring to the number of repeat units (—CH$_2$CH$_2$O—) in the dPEG chain. While a size 12 dPEG is shown, the methods described in this example are applicable to dPEG having any suitable size. Beads comprising surface carboxylic acid groups are also provided and are shown in FIG. 20A (panel II). The carboxylic acid groups may be coupled to the surface of the beads via a hydrocarbon chain. In some cases, the beads are MyOne beads that have carboxylic acid groups linked to bead surfaces via a hydrocarbon chain comprising an average of 50 repeat units. The beads can also be provided as a salt, such as, for example, a sodium salt as shown in FIG. 20A (panel II).

Figure 20B:
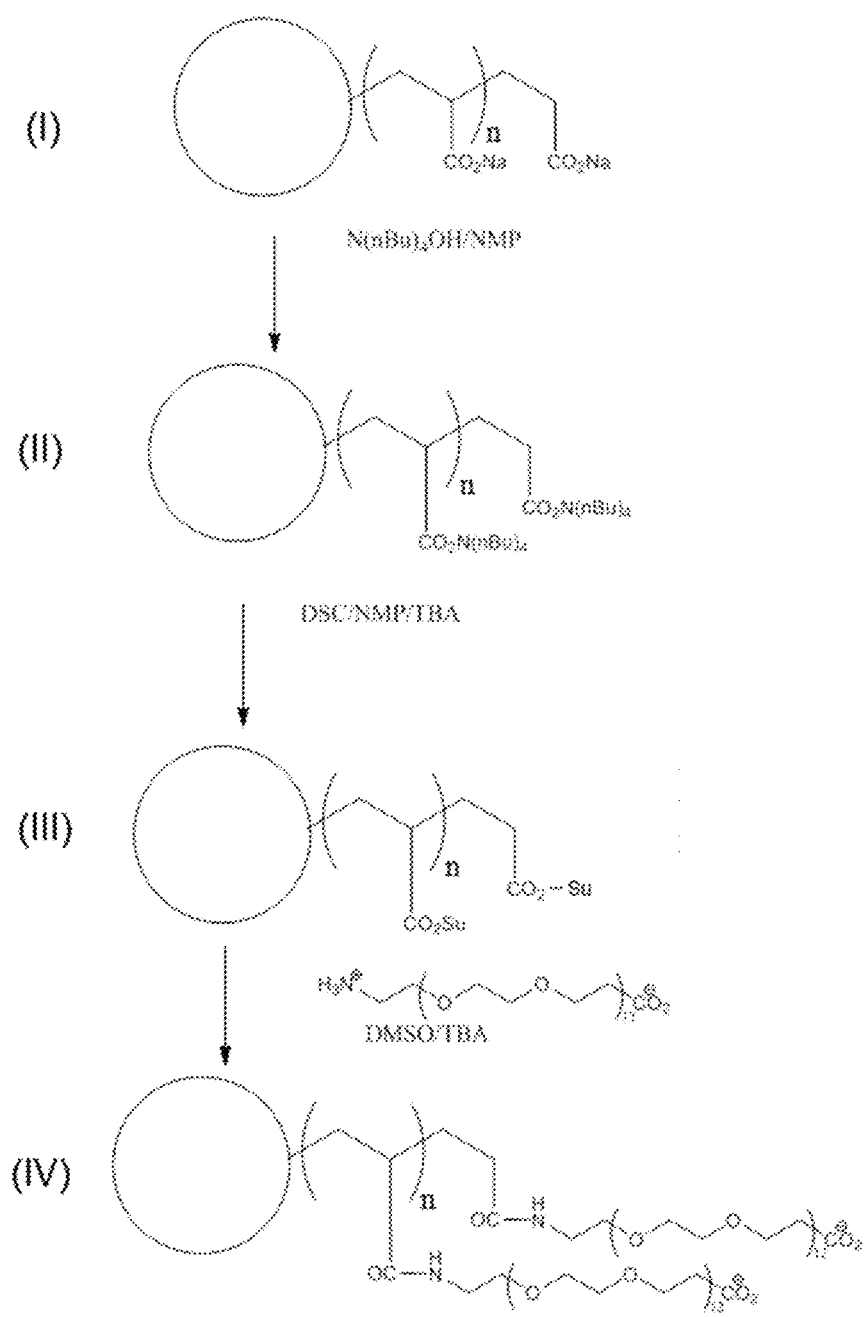

As shown in FIG. 20B, the provided beads (I) are provided as a sodium salt in an aqueous solution. (I) is first contacted with tetrabutylammonium hydroxide N(nBu)$_4$OH in the presence of N-Methyl-2-pyrrolidone (NMP) to ion exchange the beads (I) to the beads in the form of a tetrabutylammonium salt (II), followed by washing with NMP. Next, the carboxylic acid groups of the beads (II) are activated with DSC in the presence of NMP and TBA to generate beads (III) comprising amine-reactive succinimidyl reactive groups on bead surfaces. The beads (III) are then reacted with the amino-dPEG12-acid species shown in FIG. 20A (panel I) in the presence of dimethylsulfoxide (DMSO) and TBA to generate beads comprising dPEG chains (IV) having terminal carboxylic acid groups.

Figure 20C:
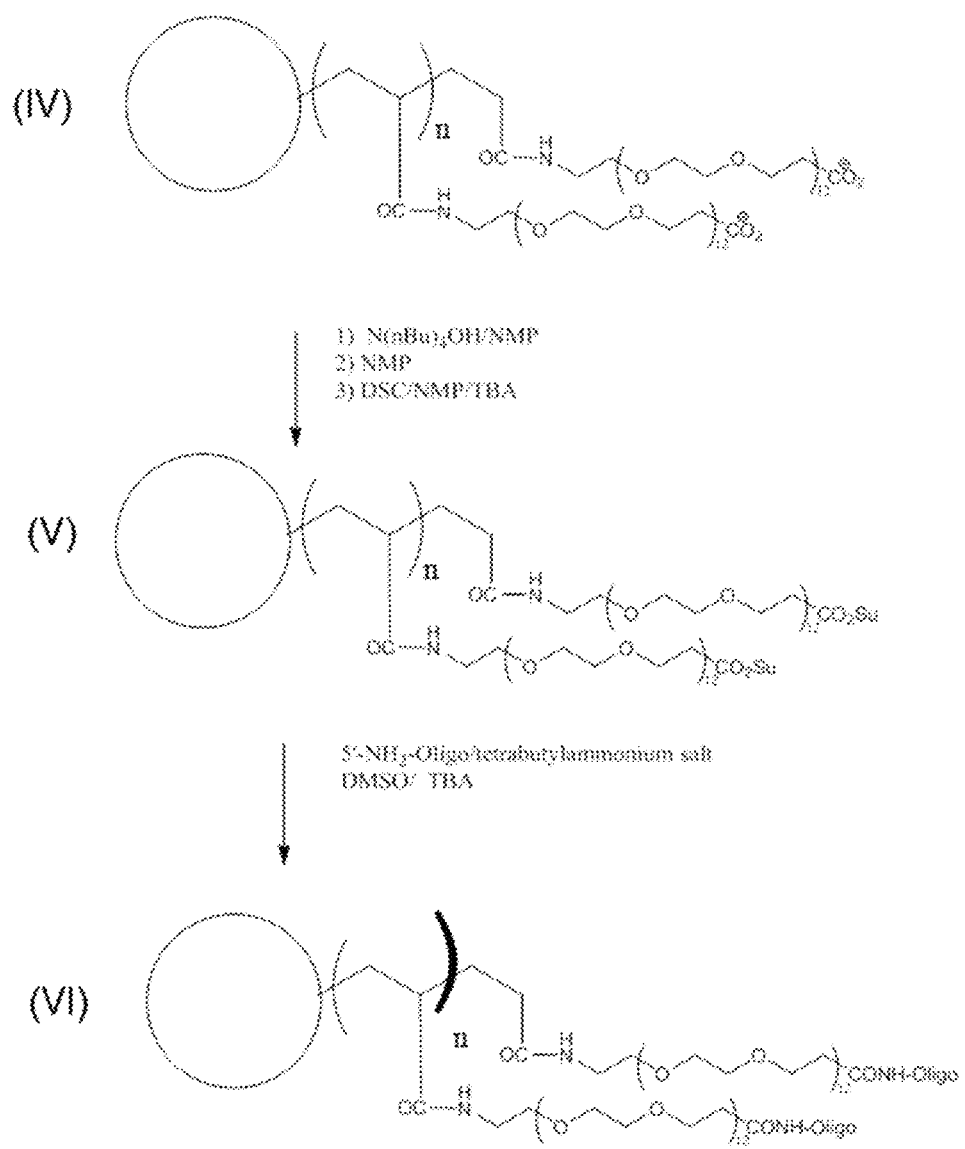

As shown in FIG. 20C, the beads (IV) are then contacted with the N(nBu)$_4$OH in the presence of NMP to convert the beads (IV) to a tetrabutylammonium salt form, followed by washing with NMP. The carboxylic acid groups of the dPEG chains are then activated with DSC in the presence of NMP and TBA to generate beads comprising dPEG chains with terminal succinimidyl groups (V). The beads (V) are then reacted with an amine-terminated oligonucleotide (e.g., 5'-NH$_2$-oligo) in the presence of tetrabutylammonium salt, DMSO, and TBA to generate beads coupled to the oligonucleotide (VI). In some cases, the oligonucleotides that are coupled to the beads are primers. In some cases the PEG in amino-dPEG12-acid can have a molecular weight (MW) of at least about 2000 Daltons (Da), at least about 3000 Da, at least about 3500 Da, at least about 4000 Da, at least about 4500 Da, at least about 5000 Da, at least about 5500 Da or more.

Example 6: Preparation of Amino Magnetic Beads 5 mL Dynal carboxylic acid beads (50 billion beads) were put in 15-mL polypropylene Falcon tube and washed once with 5 mL 1N HCl solution, once with 5 mL 10 mM HCl solution, twice with 5 mL distilled water and four times with 5 mL of anhydrous amine-free NMP. A solution of 0.512 g (2.00 mmol) of DSC and 0.50 mL (2.10 mmol) of tributylamine in 5 mL of anhydrous amine-free NMP was added and mixed at 750 rpm for 2 hours at 20° C. The beads were washed two times with 5 mL of anhydrous amine-free NMP. The beads were re-suspended in a solution of 5 mL of anhydrous amine-free NMP, 0.5 mL (6.00 mmol) of 1,3-diaminopropane and 0.50 mL (2.10 mmol) of tributylamine. The mixture was mixed at 750 rpm for 14 hours at 20° C. The beads were washed twice with 5 mL of anhydrous amine-free NMP, re-suspended in 5 mL of anhydrous amine-free NMP and stored in a refrigerator at 4° C.

Example 7: Preparation of Diluted Amino Magnetic Beads 5 mL Dynal carboxylic acid beads (50 billion beads) were put in 15-mL polypropylene Falcon tube and washed once with 5 mL 1N HCl solution, once with 5 mL 10 mM HCl solution, twice with 5 mL distilled water and four times with 5 mL of anhydrous amine-free NMP. A solution of 0.512 g (2.00 mmol) of DSC and 0.50 mL (2.10 mmol) of tributylamine in 5 mL of anhydrous amine-free NMP was added and mixed at 750 rpm for 2 hours at 20° C. The beads were washed two times with 5 mL of anhydrous amine-free NMP. The beads were re-suspended in a solution of 5 mL of anhydrous amine-free NMP, 0.25 mL (3.00 mmol) of 1,3-diaminopropane, 0.26 mL 2-methoxyethylamine (2.99 mmol) and 0.50 mL (2.10 mmol) of tributylamine. The mixture was mixed at 750 rpm for 14 hours at 20° C. The beads were washed twice with 5 mL of anhydrous amine-free NMP, re-suspended in 5 mL of anhydrous amine-free NMP and stored in a refrigerator at 4° C.

Example 8: Preparation of Initiator-Coated (BIB) Magnetic Beads 5 mL amino magnetic beads (50 billion beads, generated as described in Example 2) were put in a 15-mL polypropylene Falcon tube and washed twice with 5 mL of anhydrous dichloromethane. A solution of 0.5 mL (4.05 mmol) of α-bromo isobutyryl bromide and 0.50 mL (2.10 mmol) of tributylamine in 10 mL of anhydrous dichloromethane was added and mixed at 750 rpm for 2 hours at 20° C. The beads were washed two times with 10 mL of anhydrous dichloromethane and two times with 5 mL of anhydrous amine-free NMP. The beads were re-suspended in 5 mL of anhydrous amine-free NMP and stored in a refrigerator at 4° C.

Example 9: Preparation of ATRP-Grafted Magnetic Beads 0.25 mL initiator-coated BIB bead (2.5 billion beads, generated as described in Example 8) were washed 3 times with 0.5 mL methanol and re-suspended in 0.5 mL methanol. A monomer solution was prepared by dissolving 0.311 g hydroxyethyl acrylamide (HEAA) (2.70 mmol) and 0.812 g dimethyl acrylamide (DMA) (8.19 mmol) in 2.5 mL methanol. A copper-ligand solution was prepared by dissolving 4 mg of copper (II) bromide ($CuBr_2$) (0.02 mmol) and 25 mg tris(2-pyridylmethyl)amine (TPMA) (0.09 mmol) in 1 ml methanol. The bead suspension was combined with the monomer solution and 44 µL of the copper-ligand solution in a round bottom 4-neck flask and the mixture was deoxygenated for 30 min by bubbling ultra-pure nitrogen through the mixture. An activator solution was prepared by dissolving 25 mg ascorbic acid (0.14 mmol) in 1 mL distilled water. 0.46 mL of the activator solution was added to the degassed reaction mixture, which was degassed for another 5 min and allowed polymerize for an additional 90 min under inert atmosphere. The reaction mixture was transferred to a 15 mL Falcon tube where beads were separated from the solution. Beads were washed four times with 0.5 mL methanol and re-suspended in 0.5 mL methanol and stored in a refrigerator at 4° C.

Example 10: Preparation of Oligo Conjugated Magnetic Beads 0.1 mL ATRP-grafted magnetic beads were washed four times with 0.1 mL anhydrous amine-free NMP. A solution of 71 mg (0.28 mmol) DSC and 0.07 mL (0.29 mmol) tributylamine was prepared in 0.64 mL anhydrous amine-free NMP. 0.1 mL of the DSC solution was added to the ATRP-grafted magnetic beads and mixed at 1400 rpm for 2 hours at 20° C. The beads were washed two times with 0.1 mL of anhydrous amine-free NMP. Amine-modified oligo (30 mer) as a tetrabutylammonium salt in anhydrous amine-free NMP was prepared by dialysis of the sodium salt of the oligo against 5 mM tetrabutylammonium chloride (TBAC) (adjusted to pH 7) and subsequent dialysis against 18 MΩ water. The dialyzed oligo was freeze dried until constant weight and dissolved directly into anhydrous amine-free NMP to a 10% concentration w/v. The DSC-activated beads were charged with 0.015 mL of a 10% solution (w/v) of the amino-terminated oligo in anhydrous amine-free NMP and 0.0015 mL of tributylamine. The mixture was mixed at 1400 rpm for 14 hours at 60° C. The beads were washed with 0.2 mL of anhydrous amine-free NMP, followed by washes in 0.2 mL of water, 1N NaOH, water and bead storage buffer (1×TE (10 mM @ pH 8.0, 1 mM EDTA) containing 0.05% Triton X-100 and 0.01% sodium azide). The beads were re-suspended in 0.5 mL bead storage buffer and stored in a refrigerator at 4° C.

Example 11: Hybridization Assay of Oligo-Conjugated Magnetic Beads 0.001 mL of oligo-conjugated magnetic beads were mixed with 0.001 mL of 100 µM FAM-labeled complementary oligonucleotide and 0.018 mL annealing buffer (1×TE (10 mM Tris pH 8.0 1 mM EDTA) with 100 mM sodium chloride (NaCl)). The mixture was denatured and reannealed by heating to 95° C. for 2 min and slowly cooled down to room temperature. The beads were separated from the solution and washed twice with 0.2 mL TET buffer (1×TE with 0.01 Triton X-100), resuspended in 0.1 mL 1×TE buffer and analyzed by flow cytometry on a BD Accuri C6 flow cytometer.

Example 12: Preparation of Oligo-PEG Conjugated Magnetic Beads 2 billion amino beads suspended in acetonitrile, previously prepared using MyOne™ carboxylic beads from Thermo Scientific, are transferred to a 2-mL micro-centrifugation tube. The beads are washed 3 times with 1 mL of anhydrous dichloromethane (DCM). The amino bead pellet is charged to a solution of 19.5 mg of bis-dPEG21-PFP ester (Quanta Biodesign) in 1 mL of anhydrous DCM and 10 µL of tributylamine (TBA). The mixture is tumbled at ambient temperature for 3 hours. The beads are washed 3 times with 1 mL of anhydrous DCM, one time with 1 mL of 1:1 v/v mixture of anhydrous DCM and anhydrous DMSO, and two times with 1 mL of anhydrous DMSO. The beads are then suspended in 80 µL of anhydrous DMSO. The bead suspension is then charged with an aliquot of 10% 15-mer solution prepared by dissolving 13.4 mg of 15-mer in tetrabutylammonium salt of the 15-mer and 13.4 µL of TBA in 134 µL of anhydrous DMSO. The mixture is vortexed on a ThermoMixer at 20° C./1400 rpm for 20 hours. The beads are washed two times with 1 mL of DMSO, 1 mL of 50% aqueous DMSO and 1 mL of DI water. 1.5 mL of capping solution containing 100 mM of triethylamine, and 100 mM of ammonium hydroxide is added to the pellet of beads. The mixture is vortexed at 60° C./140 rpm for 2 hours. The beads are washed two times and DI water, one time with bead Storage Buffer prepared with 1× TE buffer containing 0.05% Triton-X100 and 0.04% of sodium azide. The beads are re-suspended in 1 mL of the Bead Storage buffer and store the beads at 4° C. refrigerator.

Systems and methods of the present disclosure may be combined with or modified by other systems and methods, such as those described in PCT Patent Application No. PCT/US2011/054769, PCT Patent Application No. PCT/US2012/039880, PCT Patent Application No. PCT/US2012/067645, PCT Patent Application No. PCT/US2014/027544, and PCT Patent Application No. PCT/US2014/069624, each of which is incorporated herein by reference in its entirety.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for preparation of a primer-conjugated bead, comprising:
   (a) coupling a plurality of polymer chains comprising a plurality of first reactive groups to an aminated bead to provide a plurality of second reactive groups coupled to the bead through a respective one of the polymer chains; and
   (b) covalently attaching amine- or hydroxy-terminated primers to the plurality of second reactive groups to form the primer-conjugated bead, wherein an individual polymer chain of the plurality of polymer chains comprises a repeat unit comprising a functional group that is different from functional groups of the plurality of first reactive groups and the plurality of second reactive groups, wherein the functional group is hydrophilic, and wherein the individual polymer chain comprises greater than or equal to 40 mole % (mol %) of the functional group,
   wherein a given polymer chain of the plurality of polymer chains comprises a carbon backbone of the formula:

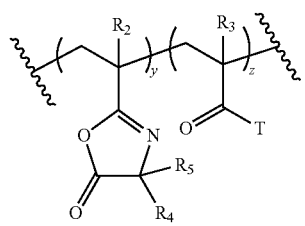

wherein 'T' is selected from the group consisting of $NH_2$, $NH(CH_3)$, $N(CH_3)_2$, $NH(CH_2)_tOH$, $(OCH_2CH_2)_vCH_3$, $(OCH_2CH_2)_vOH$, $(OCH_2CH_2)_vOCH_3$ and $OCH_3$, wherein 't' is 1 to 4, 'v' is 1 to 100;

wherein '$R_2$', '$R_3$', '$R_4$' and '$R_5$' are independently H or $CH_3$; and wherein 'y' and 'z' are mole percentages, wherein ('y'+'z')=100 mol %, and wherein 'y' is less than or equal to 60 mol % and 'z' is greater than or equal to 40 mol %.

2. A method for preparation of a primer-conjugated bead, comprising:
   (a) coupling a plurality of polymer chains comprising a plurality of first reactive groups to an aminated bead to provide a plurality of second reactive groups coupled to the bead through a respective one of the polymer chains, and
   (b) covalently attaching amine- or hydroxy-terminated primers to the plurality of second reactive groups to form the primer-conjugated bead, wherein an individual polymer chain of the plurality of polymer chains comprises a repeat unit comprising a functional group that is different from functional groups of the plurality of first reactive groups and the plurality of second reactive groups, wherein the functional group is hydrophilic, and wherein the individual polymer chain comprises greater than or equal to 40 mole % (mol %) of the functional group,
   wherein a given polymer chain of the plurality of polymer chains comprises a carbon backbone of the formula:

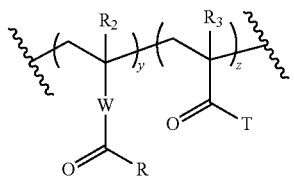

wherein 'X' is a halide;
wherein '$R_1$' is OH; $(OCH_2CH_2)_vOH$ with v=1 to 200; $NH(CH_2)_aOH$, with 'a'=1 to 6; $NH(CH_2CH_2O)_tCH_2CH_2OH$ with 't'=0 to 200;

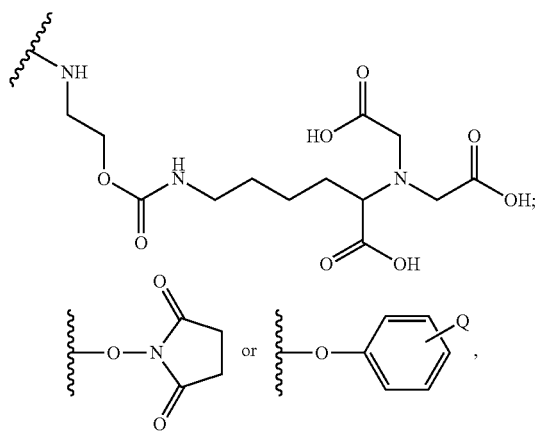

or $F_z$, with 'z'=1, 2, 3, 4 or 5;
wherein 'T' is selected from the group consisting of $NH_2$, $NH(CH_3)$, $N(CH_3)_2$, $N(CH_2CH_3)_2$, NHCH$_2$CH$_2$(OCH$_2$CH$_2$)$_b$OCH$_3$ and (OCH$_2$CH$_2$)$_d$OCH$_3$, wherein 'b'=0 to 200, 'd'=1 to 200;

wherein 'R$_2$' and 'R$_3$' are independently H or CH$_3$;

wherein 'x' and 'y' are mole percentages, wherein ('x'+'y')=100 mol % and 'x' ranges from 0.01 to 100 mol %, and wherein 'W' is a single bond or

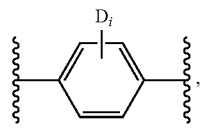

wherein 'D$_i$'=H or CH$_3$, and wherein 'i' is 1, 2, 3 or 4, independently.

3. A method for preparation of a primer-conjugated bead, comprising:
(a) coupling a plurality of polymer chains comprising a plurality of first reactive groups to an aminated bead to provide a plurality of second reactive groups coupled to the bead through a respective one of the polymer chains; and
(b) covalently attaching amine- or hydroxy-terminated primers to the plurality of second reactive groups to form the primer-conjugated bead, wherein an individual polymer chain of the plurality of polymer chains comprises a repeat unit comprising a functional group that is different from functional groups of the plurality of first reactive groups and the plurality of second reactive groups, wherein the functional group is hydrophilic, and wherein the individual polymer chain comprises greater than or equal to 40 mole % (mol %) of the functional group,
wherein a given polymer chain of the plurality of polymer chains comprises a carbon backbone of the formula:

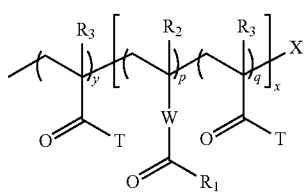

wherein 'X' is a halide;

wherein 'R$_1$' is OH; (OCH$_2$CH$_2$)$_v$OH with v=1 to 200; NH(CH$_2$)$_a$OH, with 'a'=1 to 6; NH(CH$_2$CH$_2$O)$_t$CH$_2$CH$_2$OH with 't'=0 to 200,

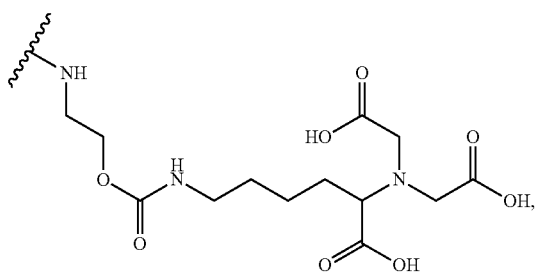

-continued

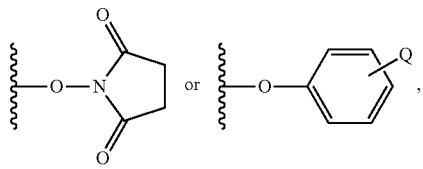

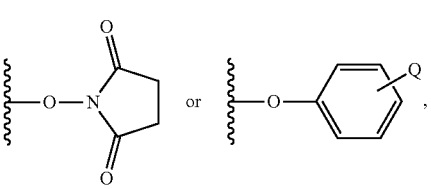

with 'Q'=NO$_2$ or F$_z$, wherein 'z' is 1, 2, 3, 4 or 5;

wherein 'T' is selected from the group consisting of NH$_2$, NH(CH$_3$), N(CH$_3$)$_2$, N(CH$_2$CH$_3$)$_2$, NHCH$_2$CH$_2$(OCH$_2$CH$_2$)$_b$OCH$_3$ and (OCH$_2$CH$_2$)$_d$OCH$_3$, wherein 'b'=0 to 200, 'd'=1 to 200;

wherein 'R$_2$' and 'R$_3$' are independently H or CH$_3$;

wherein 'y', 'p', 'q' and 'x' are mole percentages, wherein ('x'+'y')=100 mol %, ('p'+'q')=x, x ranges from 0.01 to 100 mol % and 'p' ranges from 0.01 to 100 mol %, and wherein 'W' is a single bond or

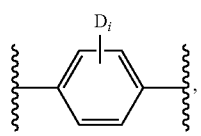

wherein 'D$_i$' is H or CH$_3$, and wherein 'i' is 1, 2, 3 or 4, independently.

4. A method for preparation of a primer-conjugated bead, comprising:
(a) coupling a plurality of polymer chains comprising a plurality of first reactive groups to an aminated bead to provide a plurality of second reactive groups coupled to the bead through a respective one of the polymer chains; and
(b) covalently attaching amine- or hydroxy-terminated primers to the plurality of second reactive groups to form the primer-conjugated bead, wherein an individual polymer chain of the plurality of polymer chains comprises a repeat unit comprising a functional group that is different from functional groups of the plurality of first reactive groups and the plurality of second reactive groups, wherein the functional group is hydrophilic, and wherein the individual polymer chain comprises greater than or equal to 40 mole % (mol %) of the functional group,
wherein a given polymer chain of the plurality of polymer chains comprises a carbon backbone of the formula:

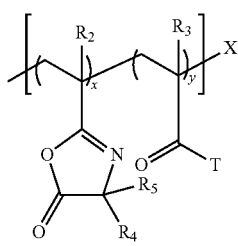

wherein 'X' is a halide;
wherein 'R$_2$', 'R$_3$', 'R$_4$' and 'R$_5$' are independently H or CH$_3$;
wherein 'T' is selected from the group consisting of NH$_2$, NH(CH$_3$), N(CH$_3$)$_2$, N(CH$_2$CH$_3$)$_2$, NHCH$_2$CH$_2$ (OCH$_2$CH$_2$)$_b$OCH$_3$ and (OCH$_2$CH$_2$)$_d$OCH$_3$, wherein 'b'=0 to 200, 'd'=1 to 200; and
wherein 'x' and 'y' are mole percentages, wherein ('x'+'y')=100 mol % and 'x' ranges from 0.01 to 100 mol %.

5. A method for preparation of a primer-conjugated bead, comprising:
(a) coupling a plurality of polymer chains comprising a plurality of first reactive groups to an aminated bead to provide a plurality of second reactive groups coupled to the bead through a respective one of the polymer chains; and
(b) covalently attaching amine- or hydroxy-terminated primers to the plurality of second reactive groups to form the primer-conjugated bead, wherein an individual polymer chain of the plurality of polymer chains comprises a repeat unit comprising a functional group that is different from functional groups of the plurality of first reactive groups and the plurality of second reactive groups, wherein the functional group is hydrophilic, and wherein the individual polymer chain comprises greater than or equal to 40 mole % (mol %) of the functional group,
wherein a given polymer chain of the plurality of polymer chains comprises a carbon backbone of the formula:

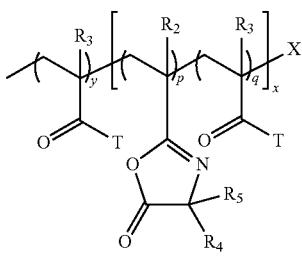

wherein 'X' is a halide;
wherein 'R$_2$', 'R$_3$', 'R$_4$' and 'R$_5$' are independently H or CH$_3$;
wherein 'T' is selected from the group consisting of NH$_2$, NH(CH$_3$), N(CH$_3$)$_2$, N(CH$_2$CH$_3$)$_2$, NHCH$_2$CH$_2$ (OCH$_2$CH$_2$)$_b$OCH$_3$ and (OCH$_2$CH$_2$)$_d$OCH$_3$, wherein 'b'=0 to 200, 'd'=1 to 200; and
wherein 'y', 'p', 'q' and 'x' are mole percentages, wherein ('x'+'y')=100 mol %, ('p'+'q')='x', 'x' ranges from 0.01 to 100 mol % and 'p' ranges from 0.01 to 100 mol %.

6. A method for coupling primers to a bead, comprising:
(a) providing a bead comprising amine groups linked to a surface of the bead;
(b) reacting at least a portion of the amine groups with polymer chains comprising a carbon backbone of the formula:

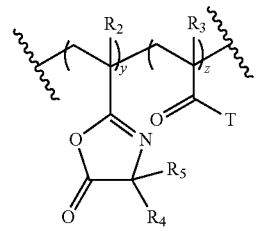

wherein 'T' is selected from the group consisting of NH$_2$, NH(CH$_3$), N(CH$_3$)$_2$, NH(CH$_2$)$_t$OH, (OCH$_2$CH$_2$)$_v$CH$_3$, (OCH$_2$CH$_2$)$_v$OH, (OCH$_2$CH$_2$)$_v$OCH$_3$ and OCH$_3$, wherein 't' is 1 to 4, 'v' is 1 to 100;
wherein 'R$_2$', 'R$_3$', 'R$_4$' and 'R$_5$' are independently H or CH$_3$; and
wherein 'y' and 'z' are mole percentages, wherein ('y'+'z')=100 mol %, wherein 'y' is less than or equal to 60 mol %, 'z' is greater than or equal to 40 mol %; and
(c) reacting the immobilized polymer chains with a primer comprising an amine group, providing immobilized primers coupled to at least a portion of the immobilized polymer chains.

7. The method of claim 1, wherein reactive groups of the plurality of first reactive groups and the plurality of second groups are the same.

8. The method of claim 1, wherein the bead is magnetic.

9. The method of claim 1, wherein, prior to (a), the polymer chains include reactive ester repeat units having a concentration of less than or equal to about 60 mol %.

10. The method of claim 1, wherein the plurality of polymer chains are coupled to the aminated bead by grafting.

11. The method of claim 2, wherein reactive groups of the plurality of first reactive groups and the plurality of second groups are the same.

12. The method of claim 2, wherein the bead is magnetic.

13. The method of claim 2, wherein, prior to (a), the polymer chains include reactive ester repeat units having a concentration of less than or equal to about 60 mol %.

14. The method of claim 2, wherein the plurality of polymer chains are coupled to the aminated bead by grafting.

15. The method of claim 3, wherein reactive groups of the plurality of first reactive groups and the plurality of second groups are the same.

16. The method of claim 3, wherein the bead is magnetic.

17. The method of claim 3, wherein, prior to (a), the polymer chains include reactive ester repeat units having a concentration of less than or equal to about 60 mol %.

18. The method of claim 3, wherein the plurality of polymer chains are coupled to the aminated bead by grafting.

19. The method of claim 4, wherein reactive groups of the plurality of first reactive groups and the plurality of second groups are the same.

20. The method of claim 4, wherein the bead is magnetic.

21. The method of claim 4, wherein, prior to (a), the polymer chains include reactive ester repeat units having a concentration of less than or equal to about 60 mol %.

22. The method of claim 4, wherein the plurality of polymer chains are coupled to the aminated bead by grafting.

23. The method of claim 5, wherein reactive groups of the plurality of first reactive groups and the plurality of second groups are the same.

24. The method of claim 5, wherein the bead is magnetic.

25. The method of claim 5, wherein, prior to (a), the polymer chains include reactive ester repeat units having a concentration of less than or equal to about 60 mol %.

26. The method of claim 5, wherein the plurality of polymer chains are coupled to the aminated bead by grafting.

* * * * *